(12) United States Patent
Halmuthur et al.

(10) Patent No.: US 8,609,858 B2
(45) Date of Patent: Dec. 17, 2013

(54) SPIRO DERIVATIVES OF PARTHENIN AS NOVEL ANTICANCER AGENTS

(75) Inventors: Mahabalarao Sampath Kumar Halmuthur, Jammu Tawi (IN); Ajit Kumar Saxena, Jammu Tawi (IN); Subhash Chandra Taneja, Jammu Tawi (IN); Shashank Kumar Singh, Jammu Tawi (IN); Vijay Kumar Sethi, Jammu Tawi (IN); Naveed Ahmed Qazi, Jammu Tawi (IN); Sanghapal Damodhar Sawant, Jammu Tawi (IN); Mahendhar Reddy Doma, Jammu Tawi (IN); Abid Hussain Banday, Jammu Tawi (IN); Monika Verma, Jammu Tawi (IN); Ghularn Nabi Qazi, Jammu Tawi (IN)

(73) Assignee: Council of Scientific & Industrial Research, New Delhi (IN)

( * ) Notice: Subject to any disclaimer, the term of this patent is extended or adjusted under 35 U.S.C. 154(b) by 10 days.

(21) Appl. No.: 12/921,061

(22) PCT Filed: Mar. 5, 2009

(86) PCT No.: PCT/IN2009/000153
§ 371 (c)(1),
(2), (4) Date: Apr. 29, 2011

(87) PCT Pub. No.: WO2009/110007
PCT Pub. Date: Sep. 11, 2009

(65) Prior Publication Data
US 2011/0201661 A1 Aug. 18, 2011

(30) Foreign Application Priority Data
Mar. 5, 2008 (IN) .............................. 527/DEL/2008

(51) Int. Cl.
*C07D 498/10* (2006.01)
*C07D 491/107* (2006.01)

(52) U.S. Cl.
USPC ............................ 548/240; 548/255; 548/958

(58) Field of Classification Search
None
See application file for complete search history.

(56) References Cited

U.S. PATENT DOCUMENTS 6,391,200 B2    5/2002  Pulek et al. ................. 210/497.1

OTHER PUBLICATIONS

Das et al. Indian Journal of Chemistry, vol. 44B, Oct. 2005, pp. 2149-2151.*
Kupchan et al. Journal of Medicinal Chemistry, vol. 14, No. 12, Dec. 1971, pp. 1147-1152.*

IUPAC. Compendium of Chemical Terminology, 2nd ed. (the "Gold Book"). Entries for "nitrile oxides," "nitrones," and "azides." Compiled by A. D. McNaught and A. Wilkinson. Blackwell Scientific Publications, Oxford (1997). <http://goldbook.iupac.org> (2006-) created by M. Nic, J. Jirat, B. Kosata; updates compiled by A. Jenkins.*
Das et al., "Baker's yeast treatment of some naturally occurring amides," *Tetrahedron Letters* 38(42): 7457-7458. Oct. 20, 1997.
Das et al., "Synthetic studies on natural products. Part 20: synthesis of novel spiro-2-isoxazolines derived from parthenin," *Indian J Chem* 44B: 2149-2151. Oct. 2005.
Das et al., "Two efficient methods for the conversion of camptothecin to mappicine ketone, an antiviral lead compound," *Tetrahedron letters* 39(5-6): 431-432. Jan. 29, 1998.
Datta and Saxena, "Pesticidal properties of parthenin (from *Parthenium hysterophorus*) and related compounds," *Pest Manag Sci* 57(1): 95-101. Jan. 2001.
Dhillon et al., "Chemical transformations of alpha-methylene-y-lactones of *Parthenium hysterophorus* Linn. and *Inula racemosa* Hook and ovicidal activity of the products against maize borer, *Chilo partellus* Swinhoe," *Indian J Chem* 33B: 1038-1042. 1994.
Dirsch et al., "Helenalin Triggers a CD95 Death Receptor-independent Apoptosis That Is Not Affected by Overexpression of Bcl-xL or Bcl-2," *Cancer Res* 61:5817-5823. Aug. 1, 2001.
Garcia-Piñeres et al., "Cysteine 38 in p65/NF-kappaB plays a crucial role in DNA binding inhibition by sesquiterpene lactones," *J Biol Chem* 276(43): 39713-39720. Oct. 26, 2001.
García-Piñeres et al., "Role of cysteine residues of p65/NF-kappaB on the inhibition by the sesquiterpene lactone parthenolide and N-ethyl maleimide, and on its transactivating potential," *Life Sci* 75(7): 841-856. Jul. 2, 2004.

(Continued)

*Primary Examiner* — Alicia L Otton
(74) *Attorney, Agent, or Firm* — Fulbright & Jaworski LLP

(57) ABSTRACT

The present invention relates to novel spiro derivatives of parthenin prepared by the dipolar cycloaddition of various dipoles viz., benzonitrile oxides, nitrones, azides, nitrile ylide diazoalkane, nitrile imide, ozone, azomethine imides, azomethine ylides etc. with exocyclic double bond of C ring (α-methylene-γ-butyrolactone). Representative compounds have been screened for their anticancer activity against different cancer cell lines. ICs0 value of these analogues varies between 4.3 μM to 93 μM. A mechanistic correlation of their anticancer activity has been described. The results of the cytotoxicity test of the compounds studies indicated that the α,β-unsaturated ketonic moiety in parthenin plays an important role in the maintenance of the high level of cytotoxicity.

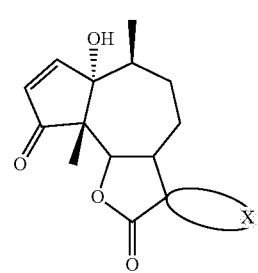

Spiro derivatives

2 Claims, 3 Drawing Sheets

(56) References Cited

OTHER PUBLICATIONS

Hamer and Macaluso, "Nitrones," *Chem Rev* 64(4): 473-495. Aug. 1964.

Hehner, "Tumor necrosis factor-alpha-induced cell killing and activation of transcription factor NF-kappaB are uncoupled in L929 cells," *J Biol Chem* 273(29): 18117-18121. Jul. 17, 1998.

Herz et al., "The Structures of Parthenin and Ambrosin," *J Am Chem Soc* 84(13):2601-2610. Jul. 1962.

Hooper et al., "Antimalarial activity of parthenin and its derivatives," *European J Med Chem* 25(9): 717-723. Nov./Dec. 1990.

Huisgen, "1,3-Dipolar Cycloadditions: Past and Future," *Angew Chem Int Ed* 2(10):565-632. 1963.

Krishan, "Rapid flow cytofluorometric analysis of mammalian cell cycle by propidium iodide staining," *J Cell Biology* 66:188-193, 1975.

Kumar et al., "Synthesis of Novel Spiroisoxazolines Through 1,3-Dipolar Cycloaddition of Nitrileoxides with alpha-Methyline Cyclic Ketones", *Synthetic Communications*, 29(5):877-884. 1999.

Baldwin et al., "Isonitrin A: Revision of the Structure and Total Synthesis in Racemic Form," *Synlett* 5:551-552. 1991.

Lee et al., "Antitumor agents. 3. Synthesis and cytotoxic activity of helenalin amine adducts and related derivatives," *J Med Chem* 15(6): 609-611. Jun. 1972.

Lyss et al., "The anti-inflammatory sesquiterpene lactone helenalin inhibits the transcription factor NF-kappaB by directly targeting p65," *J Biol Chem* 273(50: 33508-33516. Dec. 11, 1998.

Mazor et al., "Sesquiterpene lactones are potent inhibitors of interleukin 8 gene expression in cultured human respiratory epithelium," *Cytokine* 12(3): 239-245. Mar. 2000.

Monks et al., "Feasibility of a High-Flux Anticancer Drug Screen Using a Diverse Panel of Cultured Human Tumor Cell Lines," *J Natl Cancer Inst* 83(11): 757-766. 1991.

Padwa, "Intramolecular 1,3-Dipolar Cycloaddition Reactions," *Angew Chem Int Ed* 15(3): 123-136. Mar. 1976.

PCT International Preliminary Report on Patentability issued in International application No. PCT/IN2009/000153 dated May 26, 2010.

PCT International Search Report issued in International application No. PCT/IN2009/000153 dated Aug. 4, 2008.

PCT Written Opinion issued in International application No. PCT/IN2009/000153 dated Apr. 2007.

Ruesch and Mabry, "The isolation and structure of tetraneurin-A, a new pseudoguaianolide from *Parthenium alpinum* var. *tetraneuris* (compositae)," *Tetrahedron* 25(4): 805-811. 1969.

Schmidt, "Toxic activities of sesquiterpene lactones: structural and biochemical aspects," *Current Organic Chemistry* 3(6):577-608. 1999.

Skehan et al., "New Colorimetric Cytotoxicity Assay for Anticancer-Drug Screening," *J Natl Cancer Inst* 82(13): 1107-1112. 1990.

Wagner et al., "Development of a Structural Model for NF-κB Inhibition of Sesquiterpene Lactones Using Self-Organizing Neural Networks," *J Med Chem* 49(7): 2241-2252. 2006.

\* cited by examiner

Reaction of pathenin with a sulfhydryl group following a Michael addition.neckrosisnecrosis by DNA gel electrophorosis.

Figure 1

| Lane | | |
|---|---|---|
| 1 | -ve control | untreated cells |
| 2 | Camptothecin | 5µM |
| 3 | Compound 17 | 1µM |
| 4 | Compound 17 | 10µM |
| 5 | Compound 17 | 50µM |
| 6 | Compound 17 | 100uM |

Detection of Sub $G_1$ fraction (% apoptosis) in DNA cell cycle induced by "Compound-17" in MOLT-4 treated cells by flow cytometry. A control (untreated cells) B staurosporine 1μM, C, D, E, F cells treated with 1, 10, 50, 100 μM concentrations of parthinin analogue (Compound)

SPIRO DERIVATIVES OF PARTHENIN AS NOVEL ANTICANCER AGENTS

This application is a national phase application under 35 U.S.C. §371 of International Application No. PCT/IN2009/000153 filed 05 Mar. 2009, which claims priority to Indian Application No. 527/DEL/2008 filed 05 Mar. 2008. The entire text of each of the above-referenced disclosures is specifically incorporated herein by reference without disclaimer.

FIELD OF THE INVENTION

The present invention relates to novel derivatives of parthenin. The present invention particularly relates to several novel derivatives of parthenin including methods of their synthesis and their anticancer activity.

BACKGROUND OF THE INVENTION

Sesquiterpene lactones are the active constituents of a variety of medicinal plants used in traditional medicine. Parthenin the major sesquiterpenoid constituent of the weed, *Parthenium hysterophorus* L. (Compositae) exhibits significant medicinal and allelopathic activities.[1] Medicinally, this compound has been found to be of interest for its anticancer, antibacterial, antiamoebic and antimalerial properties. Various modifications of parthenin have recently been carried out to obtain more potent analogues with lower toxicity and better activity. In recent years, the anti-cancer property of various sesquiterpenes has attracted a great deal of interest and extensive research work has been carried out to characterize the anti-cancer activity, the molecular mechanisms, and the potential chemo-preventive and chemo-therapeutic application of sesquiterpenoids. Cytotoxicity, as many other biological activities of sesquiterpene lactones, is known to be mediated by the presence of potentially alkylant structure elements capable of reacting covalently with biological nucleophiles, thereby inhibiting a variety of cellular functions[2] which directs the cells into apoptosis.[3-6] Sesquiterpene lactones (SLs) have been considered interesting leads to a new class of anticancer agents in the past. The anti-inflammatory activity of SLs has been corroborated using various assays and several studies reveal that they exert their activity by inhibiting the transcription factor NF-kB.[7-10] Using helenalin and parthenolide as models, it is well established that DNA binding of NF-kB is prevented by alkylation of cysteine-38 in the p65/NF-kB subunit.[7-11] There are strong indications that this is a general mechanism for SLs, which possess, α,β-unsaturated carbonyl structures such as α-methylene-β-lactones or, α,β-unsaturated cyclopentenones. These functional groups are known to react with nucleophiles, especially with the sulfhydryl group of cysteine, in a Michael-type addition (FIG. 1). Despite the plethora of experimental studies found in literature on the cytotoxicity of particular sesquiterpene lactones against many cell lines, little is known on the effects of different alkylant structure elements and of other structural factors on cytotoxicity in terms of SAR (structure-activity relationship). This, however, would be an important step in the direction of rational lead optimization.

In parthenin (1) we have two such active sites; one is the α-methylene-γ-butyrolactone and the other one is the cyclopentenone. Even though several groups worldover, have been working on the structural modification of parthenin, [12-16] either out of curiosity or with a view to develop secondary leads, to best of our knowledge, none of these reports reveal a focused and rational approach to the modification of parthenin in order to develop a SHAL (small molecule high affinity ligand) with better anticancer activity. Thus, there are literature reports which consider that the major activity of sesquiterpenoids has been attributed to the presence of α-methylene-γ-butyrolactone while few reports claim the importance of both cyclopentenone and α-methylene-γ-butyrolactone ring,[17] whereas there has been neither any concrete SAR model proposed in literature for parthenin nor the mode of action of this molecule vis-à-vis the target protein. Even though, in literature, the importance of cyclopentenone ring as a potential alkylant structure in parthenin/SLs due to which the cytotoxicity has been attributed without any further rational effort to zero-in on the actual molecular target. The fact that 2-cyclopenten-1-one and its derivatives comprising the cyclopentenone nucleus has been established to be the inhibitors of the NF-kB factor, with anti-inflammatory, anti-proliferative, immune-suppressive, cytoprotective and antiviral activity,[18] prompted us to propose the mechanism of action of parthenin involving such a pathway through design & synthesis of various parthenin analogues in such a way that we could unequivocally establish the SAR vis-à-vis the target of interaction. Thus, despite numerous biological activities of parthenin, no concrete SAR (Structure activity relationship) model for this molecule has been established till date. The present study deals with the design, synthesis and cytotoxic evaluation of parthenin through systematic and rational approach for structural modification in order to determine the SAR of the molecule unequivocally and the improved structures synthesized by us were found to be novel ligands with increased drug-likeness.

OBJECTIVES OF THE INVENTION

The main objective of the present invention is to provide novel spiro derivatives of parthenin Another objective of the present invention is to provide a process of preparation of the novel spiro derivatives of parthenin.

One more objective of the invention is to provide the novel compounds which are more active than the parent compound.

SUMMARY OF THE INVENTION

The present invention relates to novel spiro derivatives of parthenin. The present invention particularly relates to several novel derivatives of parthenin including methods of their synthesis and their anticancer activity. The spiro derivatives of parthenin are prepared through 1,3-dipolar cycloaddition of various dipoles such as nitrile oxide, nitrones, azides, nitrile ylide, diazoalkane, nitrile imide, ozone, azomethine imides, azomethine ylides. The spiro derivatives are useful as anticancer agents.

BRIEF DESCRIPTION OF THE DRAWINGS

Scheme 1: Dipolar cycloaddition of various dipoles with the exocyclic double bond of parthenin.

Scheme 2: Synthesis of various spiro-derivatives of parthenin.

Scheme 3: Synthesis of spiro-isoxazoline derivative of parthenin.

Scheme 4: Synthesis of spiro-isoxazolidine derivative of parthenin.

Scheme 5: Synthesis of spiro-aziridine derivative of parthenin.

Scheme 6: Reduction of spiro derivative of parthenin.

Table 1. Synthesis of various spiroisoxazoline derivatives of parthenin.
Table 2. Synthesis of various spiroisoxazolidine derivatives of parthenin.
Table 3. Synthesis of various spiroaziridine derivatives of parthenin.
Table 4: $IC_{50}$ values of various derivatives of parthenin.
Table 5: Effect of Parthenin and its derivative Compound-17 on Ehrlich ascitic tumor (EAT) bearing mice.
Table 6: Effect of Parthenin and its derivative Compound-17 on Ehrlich ascitic carcinoma (EAC) bearing mice.

FIG. 1: Reaction of pathenin with a sulfhydryl group following a Michael addition.

Figure 2:

FIG. 2: Analysis of apoptosis and necrosis by DNA gel electrophoresis.

Figure 3:
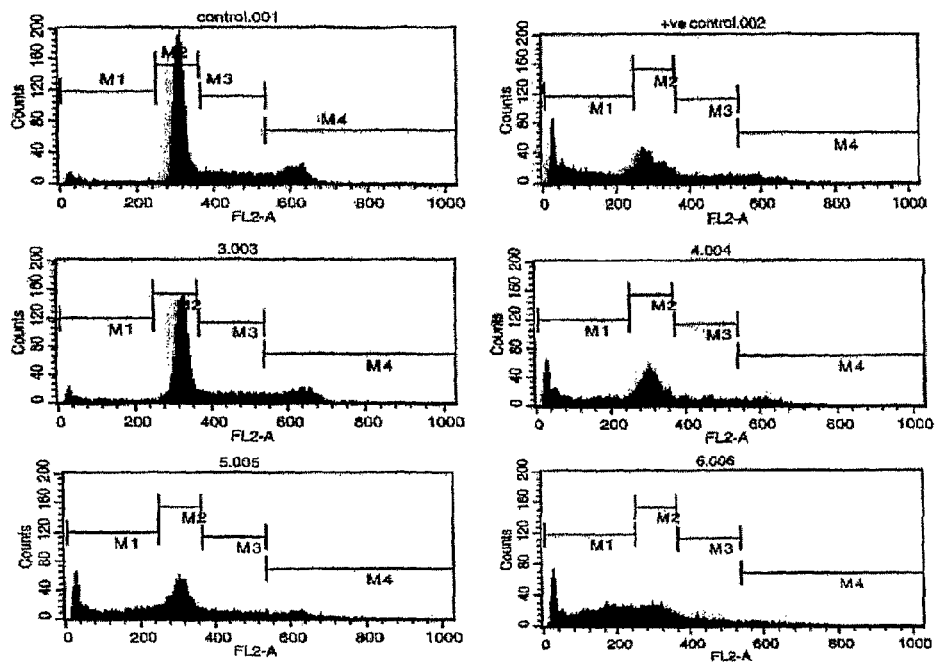

FIG. 3: Detection of Sub $G_1$ fraction (% apoptosis) in DNA cell cycle induced by "Compound 17" in MOLT-4 treated cells by flow cytometry. A control (untreated cells) B staurosporine 1 μM, C, D, E, F cells treated with 1, 10, 50, 100 μM concentrations of parthenin analogue (Compound 17) respectively.

DETAILED DESCRIPTION

Accordingly the present invention provides novel spiro-derivatives of parthenin of general structural formula 1

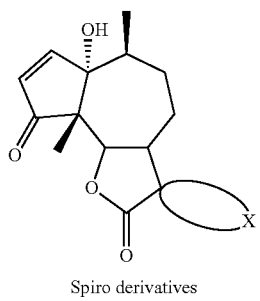

Formula 1

Spiro derivatives

Wherein, value of X is selected from a group consisting of —C=N—O—, —C—N—O—, —N—, —N—N—N—, —C=N—N—, —C—N—N—, —C—N—C—. The formula 1a, 1b, 1c and 1d, represent different spiro derivatives of parthenin which have been briefly described class wise below and are claimed in this invention including compound-17.

In an embodiment of the invention the spiro derivative is spiro-isoxazoline having general structural formula 1a;

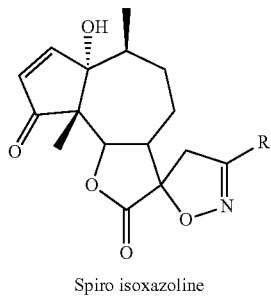

Formula 1a

Spiro isoxazoline derivative

Wherein, the substituent R is selected from a group consisting of hydrogen, alkyl substituents viz., methyl, ethyl, propyl and the higher homologues either linear or branched, including alicyclic such as cyclopentane, cyclohexane or higher membered rings, fused rings, aryl/heteroaryl substituted alkyl groups including benzylic or its higher homologues that might include unsaturated alkyl groups such as cinnamyl, crotyl, prenyl substituents; and R may also represent aryl substituent at the first position of isoxazoline ring in structure 1a, viz., substituted phenyl groups e.g., 4-$MeOC_6H_4$, 2-$NO_2C_6H_4$, 3-$NO_2C_6H_4$, 3-$HOC_6H_4$, 2-$HOC_6H_4$, 4-$HOC_6H_4$, 2,3-$(HO)_2C_6H_3$, 2,4-$(HO)_2C_6H_3$, 2,5-$(HO)_2C_6H_3$, 3,4-$(HO)_2C_6H_3$, 3,5-$(HO)_2C_6H_3$, 2,3-$(MeO)_2C_6H_3$, 2,4-$(MeO)_2C_6H_3$, 2,5-$(MeO)_2C_6H_3$, 2,6-$(EtO)_2C_6H_3$, 3,5-$(MeCH_2CH_2O)_2C_6H_3$, 2-HO-5-$MeOC_6H_3$, 3-HO-4-$MeOC_6H_3$, 2-HO-4-$MeOC_6H_3$, 2-HS-6-$MeOC_6H_3$, 2-MeO-4-$HOC_6H_3$, 2,3-$(Cl)_2C_6H_3$, 2,4-$(Cl)_2C_6H_3$, 2,5-$(Cl)_2C_6H_3$, 2,6-$(Cl)_2C_6H_3$, 4-$NMe_2$-$C_6H_4$, 4-$NO_2C_6H_4$, 2-$BrC_6H_4$, 3,5-$(Br)_2C_6H_3$, 2-Cl $C_6H_4$, 2-Br-3-$ClC_6H_3$, 2-Br-4-$ClC_6H_3$, 2-Br-6-$ClC_6H_3$, 2-Cl-4-$FC_6H_3$, 2-Cl-6-$FC_6H_3$, 3-Cl-2-$FC_6H_3$, 3-Cl-4-$FC_6H_3$, 4-Cl, 3-$FC_6H_3$, 2-Cl-6-$HOC_6H_3$, 2-Cl-4-$HOC_6H_3$, 2-Br-5-F $C_6H_3$, 3-Br-4-$FC_6H_3$, 4-Br-2-$FC_6H_3$, 5-Br-2-$FC_6H_3$, 2,3,5,6-$(F)4$ $C_6H_1$, 2,3,4,5,6-$(F)5C_6$, 3-Br-5-Cl-2-$HOC_6H_2$, 4-$AcNHC_6H_4$, 3-$AcNHC_6H_4$, 2-$AcNHC_6H_4$, 2,4,6-$(HO)3C_6H_2$, 2,4,6-$(MeO)_3C_6H_2$, 3,4-$(-OCH_2O-)C_6H_3$, 4-HO-3-$MeC_6H_3$, 3-$MeC_6H_4$, 2,4-$(Me)_2C_6H_4$, 2,4,6-$(Me)_3C_6H_2$, 2-$EtC_6H_4$, 4-Et-$C_6H_4$, 2-$EtOC_6H_4$, 3-$EtOC_6H_4$, 4-$EtOC_6H_4$, 4-$(CH_3)_2CHC_6H_4$, 2,4,6-$(EtO)_3C_6H_2$, 4-$HSC_6H_4$, 3-$MeSC_6H_4$, 3-$MeCO_2C_6H_4$, 2-$MeCO_2C_6H_4$, 4-$EtCO_2C_6H_4$, thienyl, furyl, indolyl, pyridyl, napthyl, etc.

In an embodiment of the invention, wherein the spiro derivative is spiro-isoxazolidine derivative having general structural formula 1b:

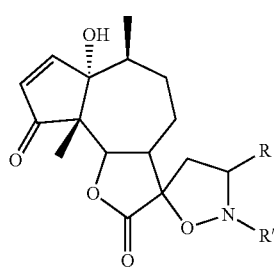

Formula 1b

Spiro isoxazolidine derivative

Wherein, the value of R/R' is selected from the group consisting of hydrogen, alkyl substituents viz., methyl, ethyl, propyl and the higher homologues either linear or branched, including alicyclic such as cyclopentane, cyclohexane or higher membered rings, fused rings, aryl/heteroaryl substituted alkyl groups including benzylic or its higher homologues including unsaturated groups such as prenyl, cinnamyl, crotyl group; and R/R' may be aryl groups at the first position of isoxazolidine ring in structure 1b. viz., Phenyl or substituted phenyl groups eg., $C_6H_5$, 4-$ClO_6H_4$, 4-$MeOC_6H_4$, 2-$NO_2C_6H_4$, 3-$NO_2C_6H_4$, 3-$HOC_6H_4$, 2-$HOC_6H_4$, 4-$HOC_6H_4$, 2,3-$(HO)_2C_6H_3$, 2,4-$(HO)_2C_6H_3$, 2,5-$(HO)_2C_6H_3$, 3,4-$(HO)_2C_6H_3$, 3,5-$(HO)_2C_6H_3$, 2,3-$(MeO)_2C_6H_3$, 2,4-$(MeO)_2C_6H_3$, 2,5-$(MeO)_2C_6H_3$, 3,4-$(MeO)_2C_6H_3$, 2,6-$(EtO)_2C_6H_3$, 3,5-$(MeCH_2CH_2O)_2C_6H_3$, 2-HO-5-$MeOC_6H_3$, 3-HO-4-$MeOC_6H_3$, 2-HO-4-MeO $C_6H_3$, 2-HS-6-MeO$C_6H_3$, 2-MeO-4-HO$C_6H_3$, 2,3-(Cl)$_2$ $C_6H_3$, 2,4-(Cl)$_2C_6H_3$, 2,5-(Cl)$_2C_6H_3$, 2,6-(Cl)$_2C_6H_3$, 3,4-(Cl)$_2C_6H_3$, 4-NMe$_2$-$C_6H_4$, 4-NO$_2C_6H_4$, 2-Br$C_6H_4$, 3,5-(Br)$_2C_6H_3$, 2-C$_1$-$C_6H_4$, 2-Br-3-Cl$C_6H_3$, 2-Br-4-Cl$C_6H_3$, 2-Br-6-Cl$C_6H_3$, 2-Cl-4-F$C_6H_3$, 2-Cl-6-F$C_6H_3$, 3-Cl-2-F$C_6H_3$, 3-Cl-4-F$C_6H_3$, 4-Cl, 3-F$C_6H_3$, 2-Cl-6-HO$C_6H_3$, 2-Cl-4-HO$C_6H_3$, 2-Br-5-F $C_6H_3$, 3-Br-4-F$C_6H_3$, 4-Br-2-F$C_6H_3$, 5-Br-2-F$C_6H_3$, 2,3,5,6-(F)4 $C_6H_1$, 2,3,4,5,6-(F)5$C_6$, 3-Br-5-Cl-2-HO$C_6H_2$, 4-AcNH$C_6H_4$, 3-AcNH$C_6H_4$, 2-AcNH$C_6H_4$, 2,4,6-(HO)3$C_6H_2$, 2,4,6-(MeO)$_3C_6H_2$, 3,4-(-OCH$_2$O—)$C_6H_3$, 4-HO-3-Me$C_6H_3$, 3-Me$C_6H_4$, 4-Me-$C_6H_4$, 2,4-(Me)$_2C_6H_4$, 2,4,6-(Me)$_3C_6H_2$, 2-Et$C_6H_4$, 4-Et-$C_6H_4$, 2-EtO$C_6H_4$, 3-EtO$C_6H_4$, 4-EtO$C_6H_4$, 4-(CH$_3$)$_2$CH$C_6H_4$, 2,4,6-(EtO)$_3C_6H_2$, 4-HS$C_6H_4$, 4-MeS$C_6H_4$, 3-MeS$C_6H_4$, 3-MeCO$_2C_6H_4$, 2-MeCO$_2C_6H_4$, 4-EtCO$_2C_6H_4$, thienyl, furyl, indolyl, pyridyl, napthyl, anthracenyl etc.

In yet another embodiment of the invention wherein spiro-triazoline derivative is having general structural formula 1c Formula 1c

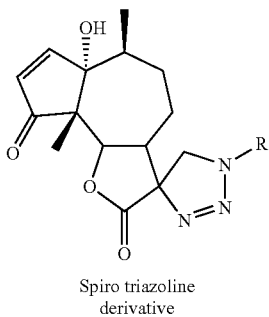

Spiro triazoline
derivative

Wherein, the value of R is selected from the group consisting of hydrogen, alkyl substituents viz., methyl, ethyl, propyl and the higher homologues either linear or branched, including alicyclic such as cyclopentane, cyclohexane or higher membered rings, fused rings, aryl/heteroaryl substituted alkyl groups including benzylic or its higher homologues that might include unsaturated alkyl groups like cinnamyl, crotyl, prenyl; and R may be aryl groups (Ar), at the first position of triazoline ring in structure 1c, viz., substituted phenyl groups e.g., 4-MeO$C_6H_4$, 2-NO$_2C_6H_4$, 3-NO$_2C_6H_4$, 3-HO$C_6H_4$, 2-HO$C_6H_4$, 4-HO$C_6H_4$, 2,3-(HO)$_2C_6H_3$, 2,4-(HO)$_2C_6H_3$, 2,5-(HO)$_2C_6H_3$, 3,4-(HO)$_2C_6H_3$, 3,5-(HO)$_2C_6H_3$, 2,3-(MeO)$_2C_6H_3$, 2,4-(MeO)$_2C_6H_3$, 2,5-(MeO)$_2C_6H_3$, 2,6-(EtO)$_2C_6H_3$, 3,5-(MeCH$_2$CH$_2$O)$_2C_6H_3$, 2-HO-5-MeO$C_6H_3$, 3-HO-4-MeO$C_6H_3$, 2-HO-4-MeO$C_6H_3$, 2-HS-6-MeO$C_6H_3$, 2-MeO-4-HO$C_6H_3$, 2,3-(Cl)$_2C_6H_3$, 2,4-(Cl)$_2C_6H_3$, 2,5-(Cl)$_2C_6H_3$, 2,6-(Cl)$_2C_6H_3$, 4-NMe$_2$-$C_6H_4$, 4-NO$_2C_6H_4$, 2-Br$C_6H_4$, 3,5-(Br)$_2C_6H_3$, 2-C$_1$-$C_6H_4$, 2-Br-3-Cl$C_6H_3$, 2-Br-4-Cl$C_6H_3$, 2-Br-6-Cl$C_6H_3$, 2-Cl-4-F$C_6H_3$, 2-Cl-6-F$C_6H_3$, 3-Cl-2-F$C_6H_3$, 8-Cl-4-F$C_6H_3$, 4-Cl, 3-F$C_6H_3$, 2-Cl-6-HO$C_6H_3$, 2-Cl-4-HO$C_6H_3$, 2-Br—S—F$C_6H_3$, 3-Br-4-F$C_6H_3$, 4-Br-2-F$C_6H_3$, 5-Br-2-F$C_6H_3$, 2,3,5,6-(F)4 $C_6H_1$, 2,3,4,5,6-(F)5$C_6$, 3-Br-5-Cl-2-HO$C_6H_2$, 4-AcNH$C_6H_4$, 3-AcNH$C_6H_4$, 2-AcNH$C_6H_4$, 2,4,6-(HO)$_3C_6H_2$, 2,4,6-(MeO)$_3C_6H_2$, 3,4-(-OCH$_2$O—)$C_6H_3$, 4-HO-3-Me$C_6H_3$, 3-Me$C_6H_4$, 2,4-(Me)$_2C_6H_4$, 2,4,6-(Me)$_3C_6H_2$, 2-Et$C_6H_4$, 4-Et-$C_6H_4$, 2-EtO$C_6H_4$, 3-EtO$C_6H_4$, 4-EtO$C_6H_4$, 4-(CH$_3$)$_2$CH$C_6H_4$, 2,4,6-(EtO)$_3C_6H_2$, 4-HS$C_6H_4$, 3-MeS$C_6H_4$, 3-MeCO$_2C_6H_4$, 2-MeCO$_2C_6H_4$, 4-EtCO$_2C_6H_4$, thienyl, furyl, indolyl, pyridyl, napthyl, anthracenyl etc.

In a further embodiment of the invention wherein spiro-aziridine derivative is having general structural formula 1d:

Formula 1d

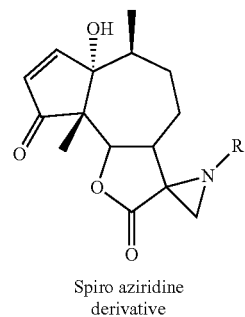

Spiro aziridine
derivative

Wherein, the substituent R is an aryl group, selected from the group consisting substituted phenyl groups e.g., 4-MeO$C_6H_4$, 2-NO$_2C_6H_4$, 3-NO$_2C_6H_4$, 3-HO$C_6H_4$, 2-HO$C_6H_4$, 4-HO$C_6H_4$, 2,3-(HO)$_2C_6H_3$, 2,4-(HO)$_2C_6H_3$, 2,5-(HO)$_2C_6H_3$, 3,4-(HO)$_2C_6H_3$, 3,5-(HO)$_2C_6H_3$, 2,3-(MeO)$_2C_6H_3$, 2,4-(MeO)$_2C_6H_3$, 2,5-(MeO)$_2C_6H_3$, 2,6-(EtO)$_2C_6H_3$, 3,5-(MeCH$_2$CH$_2$O)$_2C_6H_3$, 2-HO-5-MeO$C_6H_3$; 3-HO-4-MeO$C_6H_3$, 2-HO-4-MeO $C_6H_3$, 2-HS-6-MeO$C_6H_3$, 2-MeO-4-HO$C_6H_3$, 2,3-(Cl)$_2C_6H_3$, 2,4-(Cl)$_2C_6H_3$, 2,5-(Cl)$_2C_6H_3$, 2,6-(Cl)$_2C_6H_3$, 4-NMe2-$C_6H_4$, 4-NO$_2C_6H_4$, 2-Br$C_6H_4$, 3,5-(Br)$_2C_6H_3$, 2-Cl $C_6H_4$, 2-Br-3-Cl$C_6H_3$, 2-Br-4-Cl$C_6H_3$, 2-Br-6-Cl$C_6H_3$, 2-Cl-4-F$C_6H_3$, 2-Cl-6-F$C_6H_3$, 3-Cl-2-F$C_6H_3$, 3-Cl-4-F$C_6H_3$, 4-Cl, 3-F$C_6H_3$, 2-Cl-6-Ho$C_6H_3$, 2-Cl-4-HO$C_6H_3$, 2-Br-5-F $C_6H_3$, 3-Br-4-F$C_6H_3$, 4-Br-2-F$C_6H_3$, 5-Br-2-F$C_6H_3$, 2,3,5,6-(F)4 $C_6H_1$, 2,3,4,5,6-(F)5$C_6$, 3-Br-5-Cl-2-HO$C_6H_2$, 4-AcNH$C_6H_4$, 3-AcNH$C_6H_4$, 2-AcNH$C_6H_4$, 2,4,6-(HO)3$C_6H_2$, 2,4,6-(MeO)$_3C_6H_2$, 3,4-(-OCH$_2$O—)$C_6H_3$, 4-HO-3-Me$C_6H_3$, 3-Me$C_6H_4$, 2,4-(Me)$_2C_6H_4$, 2,4,6-(Me)$_3C_6H_2$, 2-Et$C_6H_4$, 4-Et-$C_6H_4$, 2-EtO$C_6H_4$, 3-EtO$C_6H_4$, 4-EtO$C_6H_4$, 4-(CH$_3$)$_2$CH$C_6H_4$, 2,4,6-(EtO)$_3C_6$-H$_2$, 4-HS$C_6H_4$, 3-MeS$C_6H_4$, 3-MeCO$_2C_6H_4$, 2-MeCO$_2C_6H_4$, 4-EtCO$_2C_6H_4$, thienyl, furyl, indolyl, pyridyl, napthyl, anthracenyl etc.

In a further embodiment of the invention wherein the representative compounds of formula 1 comprising all the spiro derivatives of parthenin that are covered under 1a, 1b, 1c and 1d.

Spiro-Isoxazoline Derivatives of Parthenin:

(4-methoxyphenyl)-spiro-isoxazolinyl parthenin, (2-nitrophenyl)-spiro-isoxazolinyl parthenin, (3-nitrophenyl)-spiro-isoxazolinyl parthenin, (3-hydroxyphenyl)-spiro-isoxazolinyl parthenin, (2-hydroxyphenyl)-spiro-isoxazolinyl parthenin, (4-hydroxyphenyl)-spiro-isoxazolinyl parthenin, (3-hydroxyphenyl)-spiro-isoxazolinyl parthenin, (2,3-dihydroxyphenyl)-spiro-isoxazolinyl parthenin, (2,4-dihydroxyphenyl)-spiro-isoxazolinyl parthenin, (2,5-dihydroxyphenyl)-spiro-isoxazolinyl parthenin, (3,4-dihydroxyphenyl)-spiro-isoxazolinyl parthenin, (3,5-dihydroxyphenyl)-spiro-isoxazolinyl parthenin, (2,3-dimethoxyphenyl)-spiro-isoxazolinyl parthenin, (2,3-dimethoxyphenyl)-spiro-isoxazolinyl parthenin, (2,4-dimethoxyphenyl)-spiro-isoxazolinyl parthenin, (2,5-dimethoxyphenyl)-spiro-isoxazolinyl parthenin, (2,6-diethoxyphenyl)-spiro-isoxazolinyl parthenin, (3,5-dipropoxyphenyl)-spiro-isoxazolinyl parthenin, (2-hydroxy-5-methoxyphenyl)-spiro-isoxazolinyl parthenin, (3-hydroxy-4-methoxyphenyl)-spiro-isoxazolinyl parthenin, (2-hydroxy- 4-methoxyphenyl)-spiro-isoxazolinyl parthenin, (2-Thianyl-6-methoxyphenyl)-spiro-isoxazolinyl parthenin, (2-methoxy-4-hydroxyphenyl)-spiro-isoxazolinyl parthenin, (2-,3-dichlorophenyl)-spiro-isoxazolinyl parthenin, (2-,4-dichlorophenyl)-spiro-isoxazolinyl parthenin, (2-,5-dichlorophenyl)-spiro-isoxazolinyl parthenin, (4-N,N'-dimethylphenyl)-spiro-isoxazolinyl parthenin, (4-nitrophenyl)-spiro-isoxazolinyl parthenin, (2-bromophenyl)-spiro-isoxazolinyl parthenin, (3,5-dibromophenyl)-spiro-isoxazolinyl parthenin, (2-chlorophenyl)-spiro-isoxazolinyl parthenin, (2-bromo-3-chlorophenyl)-spiro-isoxazolinyl parthenin, (2-bromo-4-chlorophenyl)-spiro-isoxazolinyl parthenin, (2-bromo-6-chlorophenyl)-spiro-isoxazolinyl parthenin, (2-chloro-4-fluorophenyl)-spiro-isoxazolinyl parthenin, (2-chloro-6-fluorophenyl)-spiro-isoxazolinyl parthenin, (3-chloro-2-fluorophenyl)-spiro-isoxazolinyl parthenin, (3-chloro-4-fluorophenyl)-spiro-isoxazolinyl parthenin, (4-chloro-3-fluorophenyl)-spiro-isoxazolinyl parthenin, (2-chloro-6-hydroxyphenyl)-spiro-isoxazolinyl parthenin, (2-chloro-4-hydroxyphenyl)-spiro-isoxazolinyl parthenin, (2-bromo-5-fluorophenyl)-spiro-isoxazolinyl parthenin, (3-bromo-4-fluorophenyl)-spiro-isoxazolinyl parthenin, (4-bromo-2-fluorophenyl)-spiro-isoxazolinyl parthenin, (5-bromo-5-fluorophenyl)-spiro-isoxazolinyl parthenin, (2,3,5,6-tetrafluorophenyl)-spiro-isoxazolinyl parthenin, (2,3,4,5,6-pentafluorophenyl)-spiro-isoxazolinyl parthenin, (3-bromo-5-chloro-2-hydroxyphenyl)-spiro-isoxazolinyl parthenin, (4-N-acetylphenyl)-spiro-isoxazolinyl parthenin, (3-N-acetylphenyl)-spiro-isoxazolinyl parthenin, (2-N-acetylphenyl)-spiro-isoxazolinyl parthenin, (2,4,6-trihydroxyphenyl)-spiro-isoxazolinyl parthenin, (2,4,6-trimethoxyphenyl)-spiro-isoxazolinyl parthenin, (3,4-methylenedioxyphenyl)-spiro-isoxazolinyl parthenin, (4-hydroxy-3-methylphenyl)-spiro-isoxazolinyl parthenin, (3-methylphenyl)-spiro-isoxazolinyl parthenin, (2,4-dimethylphenyl)-spiro-isoxazolinyl parthenin, (2,4,6-trimethylphenyl)-spiro-isoxazolinyl parthenin, (2-ethylphenyl)-spiro-isoxazolinyl parthenin, (4-ethylphenyl)-spiro-isoxazolinyl parthenin, (2-ethoxyphenyl)-spiro isoxazolinyl parthenin, (3-ethoxyphenyl)-spiro-isoxazolinyl parthenin, (4-ethoxyphenyl)-spiro isoxazolinyl parthenin, (4-isopropylphenyl)-spiro isoxazolinyl parthenin, (2,4,6-triethoxyphenyl)-spiro-isoxazolinyl parthenin, (4-thianylphenyl)-spiro isoxazolinyl parthenin, (3-thiomethylphenyl)-spiro-isoxazolinyl parthenin, methyl-3-(Isoxazolyl-5-parthenyl)-benzoate, methyl-2-(Isoxazolyl-5-parthenyl)-benzoate, ethyl-4-(Isoxazol-yl-5-parthenyl)-benzoate, thienyl-spiro-isoxazolinyl parthenin, furyl-spiro-isoxazolinyl parthenin, indolyl-spiro-isoxazolinyl parthenin, pyridyl-spir-isoxazolinyl parthenin, napthyl-spiro-isoxazolinyl parthenin, anthracenyl-spiro isoxazolinyl parthenin.

Spiro Isoxazolidine Derivatives of Parthenin:

N-(4-fluorophenyl)-C-(4-methoxyphenyl)-spiro-isoxazolidinyl parthenin, N-(4-fluorophenyl)-C-(2-nitrophenyl)-spiro-isoxazolidinyl parthenin, N-(4-fluorophenyl)-C-(3-nitrophenyl)-spiro-isoxazolidinyl parthenin, N-(4-fluorophenyl)-C-(3-hydroxyphenyl)-spiro-isoxazolidinyl parthenin, N-(2-fluorophenyl)-C-(2-hydroxyphenyl)-spiro-isoxazolidinyl parthenin, N-(2-fluorophenyl)-C-(4-hydroxyphenyl)-spiro-isoxazolidinyl parthenin, N-(2-fluorophenyl)-C-(2,3-hydroxyphenyl)-spiro-isoxazolidinyl parthenin, N-(2-fluorophenyl)-C-(2,3-hydroxyphenyl)-spiro-isoxazolidinyl parthenin, N-(2-chlorophenyl)-C-(2,5-hydroxyphenyl)-spiro-isoxazolidinyl parthenin, N-(2-fluorophenyl)-C-(3,4-hydroxyphenyl)-spiro-soxazolidinyl parthenin, N-(2-methylphenyl)-C-(3,5-hydroxyphenyl)-spiro-isoxazolidinyl parthenin, N-(2-methylphenyl)-C-(2,3-dimethoxyphenyl)-spiro-isoxazolidinyl parthenin, N-(2-methylphenyl)-C-(2,5-dimethoxyphenyl)-spiro isoxazolidinyl parthenin, N-(2-methylphenyl)-C-(2,4-dimethoxyphenyl)-spiro-isoxazolidinyl parthenin, N-(2-methoxyphenyl)-C-(2,5-dimethoxyphenyl)-spiro-isoxazolidinyl parthenin, N-(2-methoxyphenyl)-C-(2,6-diethoxyphenyl)-spiro-isoxazolidinyl parthenin, N-(2-nitrophenyl)-C-(3,5-dipropoxyphenyl)-spiro-isoxazolidinyl parthenin, N-(2-nitrophenyl)-C-(2-hydroxy-5-methoxyphenyl)-spiro-isoxazolinyl parthenin, N-(2-nitrophenyl)-C-(3-hydroxy-4-methoxyphenyl)-spiro-isoxazolidinyl parthenin, N-(2-bromophenyl)-C-(2-hydroxy-4-methoxyphenyl)-spiro-isoxazolidinyl parthenin, N-(2-bromophenyl)-C-(2-thianyl-6-methoxyphenyl)-spiro-isoxazolidinyl parthenin, N-(2-chlorophenyl)-C-(2-methoxy-4-hydroxyphenyl)-spiro-isoxazoldinyl parthenin, N-(2-chlorophenyl)-C-(2,3-dichlorophenyl)-spiro-isoxazolidinyl parthenin, N-(2-chlorophenyl)-C-(2,4-dichlorophenyl)-spiro-isoxazolidinyl parthenin, N-(2-chlorophenyl)-C-(2-,5-dichlorophenyl)-spiro-isoxazolidinyl parthenin, N-(4-hydroxyphenyl)-C-(4-N,N'-dimethylphenyl)-spiro-isoxazolidinyl parthenin, N-(4-hydroxyphenyl)-C-(4-nitrophenyl)-spiro-isoxazolidinyl parthenin, N-(4-hydroxyphenyl)-C-(2-bromophenyl)-spiro-isoxazolidinyl parthenin, N-(4-hydroxyphenyl)-C-(3,5-dibromophenyl)-spiro-isoxazolidinyl parthenin, N-(4-hydroxyphenyl)-C-(2-chlorophenyl)-spiro-isoxazolidinyl parthenin, N-(4-hydroxyphenyl)-C-(2-bromo-3-chlorophenyl)-spiro-isoxazolidinyl parthenin, N-(4-chloro-3-hydroxyphenyl)-C-(2-bromo-4-chlorophenyl)-spiro-isoxazolidinyl parthenin, N-(4-chloro-3-hydroxyphenyl)-C-(2-bromo-6-chlorophenyl)-spiro-isoxazolidinyl parthenin, N-(4-chloro-3-hydroxyphenyl)-C-(2-chloro-4-fluorophenyl)-spiro-isoxazolidinyl parthenin, N-(4-chloro-3-bromophenyl)-C-(2-chloro-6-fluorophenyl)-spiro-isoxazolidinyl parthenin, N-(4-chloro-3-hydroxyphenyl)-C-(3-chloro-2-fluorophenyl)-spiro-isoxazolidinyl parthenin, N-(4-chloro-3-hydroxyphenyl)-C-(3-chloro-4-fluorophenyl)-spiro-isoxazolidinyl parthenin, N-(2-nitrophenyl)-C-(4-chloro-3-fluorophenyl)-spiro-isoxazolidinyl parthenin, N-(2-nitrophenyl)-C-(2-chloro-6-hydroxyphenyl)-spiro-isoxazolidinyl parthenin, N-(2-nitrophenyl)-C-(2-chloro-4-hydroxyphenyl)-spiro-isoxazolidinyl parthenin, N-(2-nitrophenyl)-C-(2-bromo-5-fluorophenyl)-spiro-isoxazolidinyl parthenin, N-(2-nitrophenyl)-C-(3-bromo-4-fluorophenyl)-spiro-isoxazolidinyl parthenin, N-(2-methoxyphenyl)-C-(4-bromo-2-fluorophenyl)-spiro-isoxazolidinyl parthenin, N-(2-methoxyphenyl)-C-(5-bromo-5-fluorophenyl)-spiro-isoxazolidinyl parthenin, N-(2-methoxyphenyl)-C-(2,3,5,6-tetrafluorophenyl)-spiro-isoxazolidinyl parthenin, N-(2-methoxyphenyl)-C-(2,3,4,5,6-pentafluorophenyl)-spiro-isoxazolidinyl parthenin, N-(2-methoxyphenyl)-C-(3-bromo-5-chloro-2-hydroxyphenyl)-spiro-isoxazolidinyl parthenin, N-(2-methoxyphenyl)-C-(4-N-acetylphenyl)-spiro-isoxazolidinyl parthenin, N-(2-methoxyphenyl)-C-(3-N-acetylphenyl)-spiro-isoxazolidinyl parthenin, N-(2-methoxyphenyl)-C-(2-N-acetylphenyl)-spiro-isoxazolidinyl parthenin, N-(2-methoxyphenyl)-C-(2,4,6-trihydroxyphenyl)-spiro-isoxazolidinyl parthenin, N-(2-methoxyphenyl)-C-(2,4,6-trimethoxyphenyl)-spiro-isoxazolidinyl parthenin, N-(2-methoxyphenyl)-C-(3,4-methylenedioxyphenyl)-spiro-isoxazolidinyl, parthenin, N-(2-methoxyphenyl)-C-(4-hydroxy-3-methylphenyl)-spiro-isoxazolidinyl parthenin, N-(2-nitrophenyl)-C-(3-methylphenyl)-spiro-isoxazolidinyl parthenin, N-(2-nitrophenyl)-C-(2,4-dimethylphenyl)-spiro-isoxazolidinyl parthenin, N-(2-nitrophenyl)-C-(2,4,6-trimethylphenyl)-spiro-isoxazolidinyl parthenin, N-(2-nitrophenyl)-C-(2-ethylphenyl)-spiro-isoxazolidinyl parthenin, N-(2-nitrophenyl)-C-(4-ethylphenyl)-spiro-isoxazolidinyl parthenin, N-(2-nitrophenyl)-

C-(2-ethoxyphenyl)-spiro-isoxazolidinyl parthenin, N-(2-nitrophenyl)-C-(3-ethoxyphenyl)-spiro-isoxazolidinyl parthenin, N-(2-nitrophenyl)-C-(4-ethoxyphenyl)-spiro-isoxazolidinyl parthenin, N-(2-nitrophenyl)-C-(4-isopropylphenyl)-spiro-isoxazolidinyl parthenin, N-(2-nitrophenyl)-C-(2,4,6-methoxyphenyl)-spiro-isoxazolidinyl parthenin, N-(2-methoxyphenyl)-C-(4-thianylphenyl)-spiro-isoxazolidinyl parthenin, N-(2-methoxyphenyl)-C-(3-thiomethylphenyl)-spiro-isoxazolidinyl parthenin, N-(2-methoxyphenyl)-C-methyl-3-(Isoxazolidinyl-5-parthenyl)-benzoate, N-(2-methoxyphenyl)-C-methyl-2-(Isoxazolidinyl-5-parthenyl)-benzoate, N-(2-methoxyphenyl)-C-ethyl-4-(Isoxazolidinyl-5-parthenyl)-benzoate, N-(4-chloro-3-fluorophenyl)-C-(theiny)l-spiro-isoxazolidinyl parthenin, N-(4-chlorophenyl)-C-(furyl)-spiro-isoxazolidinyl parthenin, N-(4-chloro-3-fluorophenyl)-C-(indolyl)-spiro-isoxazolidinyl parthenin, N-(4-chloro-3-fluorophenyl)-C-(pyridyl)-spiro-isoxazolidinyl parthenin, N-(4-chlorophenyl)-C-(napthyl)-spiro-isoxazolidinyl parthenin, N-(4-chloro-3-fluorophenyl)-C-(anthracenyl)-spiro-isoxazolidinyl parthenin.

Spiro-Aziridine Derivatives of Parthenin:

(4-methoxyphenyl)-spiro-aziridinyl parthenin, (2-nitrophenyl)-spiro-aziridinyl parthenin, (3-nitrophenyl)-spiro-aziridinyl parthenin, (3-hydroxyphenyl)-spiro-aziridinyl parthenin, (2-hydroxyphenyl)-spiro-aziridinyl parthenin, (4-hydroxyphenyl)-spiro-aziridinyl parthenin, (3-hydroxyphenylspiro-aziridinyl parthenin, (2,3-dihydroxyphenyl)-spiro-aziridinyl parthenin, (2,4-dihydroxyphenyl)-spiro-aziridinyl parthenin, (2,5-dihydroxyphenyl)-spiro-aziridinyl parthenin, (3,4-dihydroxyphenyl)-spiro-aziridinyl parthenin, (3,5-dihydroxyphenyl)-spiro-aziridinyl parthenin; (2,3-dimethoxyphenyl)-spiro-aziridinyl parthenin, (2,3-dimethoxyphenyl)-spiro-aziridinyl parthenin, (2,4-dimethoxyphenyl)-spiro-aziridinyl parthenin, (2,5-dimethoxyphenyl)-spiro-aziridinyl parthenin, (2,6-diethoxyphenyl)-spiro-aziridinyl parthenin, (3,5-dipropoxyphenyl)-spiro-aziridinyl parthenin, (2-hydroxy-5-methoxyphenyl)-spiro-aziridinyl parthenin, (3-hydroxy-4-methoxyphenyl)-spiro-aziridinyl parthenin, (2-hydroxy-4-methoxyphenyl)-spiro-aziridinyl parthenin, (2-Thianyl-6-methoxyphenyl)-spiro-aziridinyl parthenin, (2-methoxy-4-hydroxyphenyl)-spiro-aziridinyl parthenin, (2-,3-dichlorophenyl)-spiro-aziridinyl parthenin, (2-,4-dichlorophenyl)-spiro-aziridinyl parthenin, (2-,5-dichlorophenyl)-spiro-aziridinyl parthenin, (4-N,N'-dimethylphenyl)-spiro-aziridinyl parthenin, (4-nitrophenyl)-spiro-aziridinyl parthenin, (2-bromophenyl)-spiro-aziridinyl parthenin, (3,5-dibromophenyl)-spiro-aziridinyl parthenin, (2-chlorophenyl)-spiro-aziridinyl parthenin, (2-bromo-3-chlorophenyl)-spiro-aziridinyl parthenin, (2-bromo-4-chlorophenyl)-spiro-aziridinyl parthenin, (2-bromo-6-chlorophenyl)-spiro-aziridinyl parthenin, (2-chloro-4-fluorophenyl)-spiro-aziridinyl parthenin, (2-chloro-6-fluorophenyl)-spiro-aziridinyl parthenin, (3-chloro-2-fluorophenyl)-spiro-aziridinyl parthenin, (3-chloro-4-fluorophenyl)-spiro-aziridinyl parthenin, (4-chloro-3-fluorophenyl)-spiro-aziridinyl parthenin, (2-chloro-6-hydroxyphenyl)-spiro-aziridinyl parthenin, (2-chloro-4-hydroxyphenyl)-spiro-aziridinyl parthenin, (2-bromo-5-fluorophenyl)-spiro-aziridinyl parthenin, (3-bromo-4-fluorophenyl)-spiro-aziridinyl parthenin, (4-bromo-2-fluorophenyl)-spiro-aziridinyl parthenin, (5-bromo-5-fluorophenyl)-spiro-aziridinyl parthenin, (2,3,5,6-tetrafluorophenyl)-spiro-aziridinyl parthenin, (2,3,4,5,6-pentafluorophenyl)-spiro-aziridinyl parthenin, (3-bromo-5-chloro-2-hydroxyphenyl)-spiro-aziridinyl parthenin, (4-N-acetylphenyl)-spiro-aziridinyl parthenin, (3-N-acetylphenyl)-spiro-aziridinyl parthenin, (2-N-acetylphenyl)-spiro-aziridinyl parthenin, (2,4,6-trihydroxyphenyl)-spiro-aziridinyl parthenin, (2,4,6-trimethoxyphenyl)-spiro-aziridinyl parthenin, (3,4-methylenedioxyphenyl)-spiro-aziridinyl parthenin, (4-hydroxy-3-methylphenyl)-spiro-aziridinyl parthenin, (3-methylphenyl)-spiro-aziridinyl parthenin, (2,4-dimethylphenyl)-spiro-aziridinyl parthenin, (2,4,6-trimethylphenyl)-spiro-aziridinyl parthenin, (2-ethylphenyl)-spiro-aziridinyl parthenin, (4-ethylphenyl)-spiro-aziridinyl parthenin, (2-ethoxyphenyl)-spiro-aziridinyl parthenin, (3-ethoxyphenyl)-spiro-aziridinyl parthenin, (4-ethoxyphenyl)-spiro-aziridinyl parthenin, (4-isopropylphenyl)-spiro-aziridinyl parthenin, (2,4,6-triethoxyphenyl)-spiro-aziridinyl parthenin, (4-thianylphenyl)-spiro-aziridinyl parthenin, (3-thiomethylphenyl)-spiro-aziridinyl parthenin, methyl-3-(aziridinyl-2-parthenyl)-benzoate, methyl-2-(aziridinyl-2-parthenyl)-benzoate, ethyl-4-(aziridinyl-2-parthenyl)-benzoate, thienyl-spiro-aziridinyl parthenin, furyl-spiro-aziridinyl parthenin, indolyl-spiro-aziridinyl parthenin, pyridyl-spiro-aziridinyl parthenin, napthyl-spiro-aziridinyl parthenin, anthracenyl-spiro-aziridinyl parthenin.

Spiro Triazoline Derivatives of Parthenin:

(4-methoxyphenyl)-spiro-1,2,3-triazolinyl parthenin, (2-nitrophenyl)-spiro-1,2,3-triazolinyl parthenin, (3-nitrophenyl)-spiro-1,2,3-triazolinyl parthenin, (3-hydroxyphenyl)-spiro-1,2,3-triazolinyl parthenin, (2-hydroxyphenyl)-spiro-1,2,3-triazolinyl parthenin, (4-hydroxyphenyl)-spiro-1,2,3-triazolinyl parthenin, (3-hydroxyphenyl)-spiro-1,2,3-triazolinyl parthenin, (2,3-dihydroxyphenyl)-spiro-1,2,3-triazolinyl parthenin, (2,4-dihydroxyphenyl)-spiro-1,2,3-triazolinyl parthenin, (2,5-dihydroxyphenyl)-spiro-1,2,3-triazolinyl parthenin, (3,4-dihydroxyphenyl)-spiro-1,2,3-triazolinyl parthenin, (3,5-dihydroxyphenyl)-spiro-1,2,3-triazolinyl parthenin, (2,3-dimethoxyphenyl)-spiro-1,2,3-triazolinyl parthenin, (2,3-dimethoxyphenyl)-spiro-1,2,3-thiazolinyl parthenin, (2,4-dimethoxyphenyl)-spiro-1,2,3-triazolinyl parthenin, (2,5-dimethoxyphenyl)-spiro-1,2,3-triazolinyl parthenin, (2,6-diethoxyphenyl)-spiro-1,2,3-triazolinyl parthenin, (3,5-diprop oxyphenyl)-spiro-1,2,3-triazolinyl parthenin, (2-hydroxy-5-methoxyphenyl)-spiro-1,2,3-triazolinyl parthenin, (3-hydroxy-4-methoxyphenyl)-spiro-1,2,3-triazolinyl parthenin, (2-hydroxy-4-methoxyphenyl)-spiro-1,2,3-triazolinyl parthenin, (2-Thianyl-6-methoxyphenyl)-spiro-1,2,3-triazolinyl parthenin, (2-methoxy-4-hydroxyphenyl)-spiro-1,2,3-triazolinyl parthenin, (2-,3-dichlorophenyl)-spiro-1,2,3-triazolinyl parthenin, (2-,4-dichlorophenyl)-spiro-1,2,3-triazolinyl parthenin, (2-,5-dichlorophenyl)-spiro-1,2,3-triazolinyl parthenin, dimethylphenyl)-spiro-1,2,3-triazolinyl parthenin, (4-nitrophenyl)-spiro-1,2,3-triazolinyl parthenin, (2-bromophenyl)-spiro-1,2,3-triazolinyl parthenin, (3,5-dibromophenyl)-spiro 1,2,3-triazolinyl parthenin, (2-chlorophenyl)-spiro-1,2,3-triazolinyl parthenin, (2-bromo-3-chlorophenyl)-spiro-1,2,3-thiazolinyl parthenin, (2-bromo-4-chlorophenyl)-spiro-1,2,3-thiazolinyl parthenin, (2-bromo-6-chlorophenyl)-spiro-1,2,3-triazolinyl parthenin, (2-chloro-4-fluorophenyl)-spiro-1,2,3-triazolinyl parthenin, (2-chloro-6-fluorophenyl)-spiro-1,2,3-triazolinyl parthenin, (3-chloro-2-fluorophenyl)-spiro-1,2,3-triazolinyl parthenin, (3-chloro-4-fluorophenyl)-spiro-1,2,3-triazolinyl parthenin, (4-chloro-3-fluorophenyl)-spiro-1,2,3-triazolinyl parthenin, (2-chloro-6-hydroxyphenyl)-spiro-1,2,3-triazolinyl parthenin, (2-chloro-4-hydroxyphenyl)-spiro-1,2,3-triazolinyl parthenin, (2-bromo-5-fluorophenyl)-spiro-triazolinyl parthenin, (3-bromo-4-fluorophenyl)-spiro-triazolinyl parthenin, (4-bromo-2-fluorophenyl)-spiro-1,2,3-triazolinyl parthenin, (5-bromo-5-fluorophenyl)-spiro-1,2,3-triazolinyl parthenin, (2,3,5,6-tetrafluorophenyl)-spiro-1,2,3-triazolinyl parthenin, (2,3,4,5,6-pentafluorophenyl)-spiro-1,2,3-triazolinyl parthenin, (3-bromo-5-chloro-2-hydroxyphenyl)-Spiro-1,2,3-triazolinyl parthenin, (4-N-acetylphenyl)-spiro-1,2,3-triazolinyl parthenin, (3-N-acetylphenyl)-spiro-1,2,3-triazolinyl parthenin, (2-N-acetylphenyl)-spiro-1,2,3-triazolinyl parthenin, (2,4,6-trihydroxyphenyl)-spiro-1,2,3-triazolinyl parthenin, (2,4,6-trimethoxyphenyl)-spiro-1,2,3-triazolinyl parthenin, (3,4-methylenedioxyphenyl)-spiro-1,2,3-triazolinyl parthenin, (4-hydroxy-3-methylphenyl)-spiro-1,2,3-triazolinyl parthenin, (3-methylphenyl)-spiro-1,2,3-triazolinyl parthenin, (2,4-dimethylphenyl)-spiro-1,2,3-triazolinyl parthenin, (2,4,6-trimethylphenyl)-spiro-1,2,3-triazolinyl parthenin, (2-ethylphenyl)-spiro-1,2,3-triazolinyl parthenin, (4-ethylphenyl)-spiro-1,2,3-triazolinyl parthenin, (2-ethoxyphenyl)-spiro-1,2,3-triazolinyl parthenin, (3-ethoxyphenyl)-spiro-1,2,3-triazolinyl parthenin, (4-ethoxyphenyl)-spiro-1,2,3-triazolinyl parthenin, (4-isopropylphenyl)-spiro-1,2,3-triazolinyl parthenin, (2,4,6-triethoxyphenyl)-spiro-1,2,3-triazolinyl parthenin, (4-thianylphenyl)-spiro-1,2,3-triazolinyl parthenin, (3-thiomethylphenyl)-spiro-1,2,3-triazolinyl parthenin, methyl-3-(1,2,3-triazolinyl-5-parthenyl)-benzoate, methyl-2-(1,2,3-triazolinyl-5-parthenyl)-benzoate, ethyl-4-(1,2,3-triazolinyl-5-parthenyl)-benzoate, thienyl-spiro-1,2,3-triazolinyl parthenin, furyl-spiro-1,2,3-triazolinyl parthenin, indolyl-spiro-1,2,3-triazolinyl parthenin, pyridyl-spiro-1,2,3-triazolinyl parthenin, napthyl-spiro-1,2,3-triazolinyl parthenin, anthracenyl-spiro-1,2,3-triazolinyl parthenin.

In an embodiment of the invention wherein the compound of formula 1 exhibit potential anticancer activity against human cancer cell lines selected from the group consisting of SW-620, prostrate, PC-3, DU-145 and acute lymphoblastic leukemia (MOLT-4).

In an embodiment of the invention wherein the compound is effective to inhibit the tumor growth at a dose ranging between 10-200 mg/Kg body weight.

In an embodiment of the invention wherein the compound of formula 1 has the significant cytotoxic potential and they induce concentration dependent apoptosis in cancer cells.

In an embodiment of the invention wherein the spiro derivatives of formula 1 showed comparable growth inhibition (≥80%) of human cancer cell lines at 100 M.

In an embodiment of the invention wherein cell cycle analysis indicates increased sub G1 population, G1 blockade and distinct laddering pattern in DNA fragmentation assay.

Accordingly the present invention provides a process for preparation of spiro-derivatives of parthenin of general Formula 1 comprises: reacting parthenin with a dipole compound selected form a group consisting of nitrile oxide, nitrones, azides, nitrile ylide, diazoalkane, nitrile imide, ozone, azomethine imides, azomethine ylides in an organic solvent at a temperature ranging between 0 to 25° C. for a period ranging between 2 to 25 hr, quenching the reaction with ammonium chloride followed by purification to obtain the corresponding spiro-derivative of formula 1.

In an embodiment of the invention wherein the organic solvent is selected for a group consisting of tetrahydrofuran, benzene, toluene, dichloromethane, dichloroethane, etc.

In an embodiment of the invention wherein the ratio of the parthenin and the dipole compound is ranging between 1.0 to 1.2:1.5 equivalent.

A pharmaceutical composition may be prepared comprising the compound of formula 1 optionally along with the pharmaceutically acceptable excipient, additive or diluent.

Even though several groups world over have been working on the structural modification of parthenin,[12-16] either out of curiosity or with a view to develop secondary leads, to best of our knowledge, none of these reports reveal a focused and rational approach to the modification of parthenin in order to develop a SHAL with better anticancer activity. Keeping in view the structural and pharmacological importance of this sesquiterpenoid lactone, a systematic approach is conceived by us for deciphering the SAR of this natural product, thereby transforming the primary lead molecules into better secondary leads.

To establish the role of exo/endocyclic double bonds towards the anticancer activity, a strategy to selectively react one of these double bonds has been devised. Out of few chemical transformational possibilities available to achieve the above goal, we chose to work on selective addition of dipole, i.e., nitrite oxide, nitrone and azide to exocyclic double bond (scheme1), which should also enhance the activity due to the introduction of basic nitrogen atom into the structural framework. Thus, keeping in view the Lipinski's rule together with the possibility to introduce nitrogen bearing (alkaloid type) structural moiety, better secondary leads could be possibly derived applying this strategy.

Both endo as well as the exocyclic double bond are active double bonds, but because of steric hindrance offered by the substitution at the cyclopentenone ring, nitrile oxide cycloadds selectively to the exocyclic double bond alone. In this patent, nitrite oxide, nitrone and azide cycloaddition to the exocyclic double bond of parthenin to generate a focused library of novel spiro-isoxazolines (2)/isoxazolidine (3) and spiro-aziridine (4) is presented (scheme 2). By screening the anticancer activity of these novel spiro derivatives we can easily establish the pharmacological importance of cyclopentenone ring over the α-methylene-γ-butyrolactone ring, thereby establishing the SAR of the molecule unequivocally.

Results:

Chemistry:

Synthesis of Spiroisoxazoline Derivatives of Parthenin via 1,3-Dipolar Cycloaddition of Nitrile Oxides to the Active Double Bond of Parthenin:

As discussed before the synthesis of spiroisoxazoline derivatives of parthenin exemplifies a modified facile method for the protection of the highly reactive α-methylene-γ-butyrolactone, a structural unit commonly found in many naturally occurring sesquiterpene lactones. All spiroisoxazoline derivatives (2) of parthenin (scheme-3/table-1) were prepared through 1,3-dipolar cycloaddition of various nitrile oxides (5) (both stable as well as in situ generated) to parthenin (1) according to the literature procedure.[19,20] Spiroisoxazoline derivatives of parthenin are formed in all the cases as sole products (>65%).

Synthesis of Spiroisoxazolidine Derivatives of Parthenin via 1,3-Dipolar Cycloaddition of Nitrone to the Exocyclic Double Bond of Parthenin:

Synthesis of spiroisoxazolidine derivatives of parthenin also exemplifies a modified facile method for the protection of the highly reactive α-methylene-γ-butyrolactone. All spiroisoxazolidine derivatives (3) of parthenin (scheme-4/table-2) were prepared through 1,3-dipolar cycloaddition of various nitrons (6) to parthenin (1) as per literature procedure.[21] Spiroisoxazolidine derivatives of parthenin are formed in all the cases as sole products (>75%).

Synthesis of Spiroaziridine Derivatives of Parthenin via 1,3-Dipolar Cycloaddition of Azide to the Exocyclic Double Bond of Parthenin:

Spiroaziridine derivatives of parthenin (4) (scheme-5/table-3) were prepared through 1,3-dipolar cycloaddition of various azides (7) to parthenin (1) as per literature precident.[19,20] Spiroaziridine derivatives of parthenin are formed in all the cases as sole products (>65%). The entire products synthesized were characterized by IR, $^1$H, $^{13}$C NMR/DEPT and mass spectroscopy.

We tested in all 43 different derivatives of parthenin for their possible anticancer activity against four cancer cell lines. Most of the spiro derivatives of parthenin were found to exhibit desirable anticancer activity. Among all the spiro-derivatives synthesized spiroisoxazoline derivatives of parthenin, Compound-17 exhibited optimal cytotoxicity. We therefore used the same compound for further evaluation.

Reduction of Spiroisoxazoline Derivative of Parthenin:

The spiroisoxazoline derivative of parthenin was selectively reduced by the standard procedure[12] employing 5% Pd/C (scheme 6). The product was confirmed in proton NMR by the disappearance of the signals corresponding to the olefinic protons of the cyclopentenone ring. The dihydro-parthenin derivative when screened for its anticancer activity was found to be inactive. This clearly reveals the importance of endocyclic double bond of parthenin towards its anticancer activity as possible site of alkylation with biological nucleophiles.

Biological Activity:

As discussed above cytotoxicity is known to be mediated by the presence of potentially alkylant structure elements capable of reacting covalently with biological nucleophiles, thereby inhibiting a variety of cellular functions, which directs the cells into apoptosis.[2,3] Here in this patent we presented the synthesis and anticancer activity of these spiro derivatives of parthenin against different cancer cell lines. We tested in all 43 different derivatives of parthenin for their possible anticancer activity against three cancer cell lines. Amongst of which most of the spiro derivatives were having comparable activity and few were having even better activity than parent compound. In the whole series of 43 spiro derivatives Compound-17 was having the maximum activity in almost all three cancer cell lines. We therefore used this compound for further evaluation and the results are summarized below.

Results Pertaining Evaluation of Anticancer Activities of Representative Spiro-Derivatives of Parthenin In vitro Cytotoxicity Screening in Human Tumor Cell Lines:

Cells at sub confluent stage were harvested from the flask by treatment with trypsin (0.5% in PBS containing 0.02% EDTA) for determination of cytotoxicity. Cells with viability of more than 98%, as determined by trypan blue, were used for assay. The cell suspensions of required cell density were prepared in complete growth medium with gentamycin (50 μg/ml) for determination of cytotoxicity. The cells (100 μl/well) were inoculated in 96 well tissue culture plates. The cells were allowed to grow for 24 hrs temperature of 37° C. and in a humidified atmosphere of 5% $CO_2$ in air. Stock solution of (20 mM) of test material was prepared in DMSO. The stock solution was serially diluted with complete growth medium containing 50 μg/ml of gentamycin to obtain three working test solutions of 1., 2, 5, 10, 50 and 100 μM. In vitro cytotoxicity ($IC_{50}$ value) against human cancer cell lines was determined using sulphodamine B dye.[5,6] The results are summarized in table 4.

Most of the spiro derivatives showed comparable growth inhibition (80%) of human cancer cell lines at 100 μM and few were having even better activity than parent compound (Parthenin). Among the series of parthenin analogues "Compound-17" seems to be most promising as it showed 70% or greater growth inhibition of human cancer cell lines even at 5 μM concentration against all the cell lines used in the present study. The maximum cell growth inhibition (85%) was observed at 5 μM against DU-145 cell line of prostate, followed by 72% and 71% with SW-620 and Hep-2 of colon and liver cancer cell lines respectively.

$IC_{50}$ values of "Compound-17" (Table 4) for cell lines namely SW-620, DU-145 and PC-3, were 4.3, 4.6 and 4.9 μM respectively. It, was most active against SW-620, which was followed by DU-145 and PC-3. This may be due to different molecular characteristic of the cells.

So from the in vitro cytotoxicity data and its $IC_{50}$ value it is revealed that among all the spiroisoxazoline derivatives "Compound-17" is the most active compound, so this compound was taken for further mechanistic studies.

Mechanism of Action:

Analysis of Apoptosis and Necrosis:

DNA Gel Electrophoresis:

DNA fragmentation was determined by electrophoresis of extracted genomic DNA from acute lymphoblastic leukemia Cells (MOLT-4). Briefly, exponentially growing cells ($3\times10^6$ cells/ml) in 6 well plates were treated with "Compound-17" (1, 10, 50 and 100 μM) for 24 hrs. Cells were harvested, washed with PBS, pellets were dissolved in lysis buffer (10 mM EDTA, 50 mM Tris Buffer, pH 8.0, 0.5% w/v SDS and proteinase K 0.5 mg/ml) and incubated at 50° C. for 1 hr. lysate was further incubated with RNase A (0.5 mg/ml) at 50° C. for 1 hr. Finally, the DNA obtained was heated rapidly to 70° C., supplemented with loading dye and immediately resolved on to 1.5% agarose gel at 50 V for 2-3 hrs (FIG. 2).

DNA Cell Cycle Analysis:

Effect of "Compound-17" on DNA content by cell cycle phase distribution was assessed using human leukemia MOLT-4. The MOLT-4 cells ($1\times10^6$ cells/ml) in RPMI-1640 medium were incubated with "Compound-17" (1, 10, 50 and 100 μM) for 24 hrs. The cells were then washed twice with ice-cold PBS, harvested, fixed with ice-cold PBS in 70% ethanol, and stored at −20° C. for 30 min. After fixation, the cells were incubated with RNase A (0.1 mg/ml) at 37° C. for 30 min, stained with propidium iodide (50 μg/ml) for 30 min on ice in dark, and then measured for DNA content using BD-LSR Flow cytometer (Becton Dickinson, USA) equipped with electronic doublet discrimination capability using blue (488 nm) excitation from argon laser. Data were collected in list mode on 10,000 events for FL2-A vs. FL2-W and analyzed (FIG. 3).[3d]

Chemicals and Reagents:

RPMI-1640, Dulbecco's Minimum Essential Medium (DMEM), glutamine, staurosporine, trypsin, gentamycin, penicillin, 5-Fluorouracil, propidium iodide (PI), agarose, ethidium bromide, sodium dodecyl sulphate (SDS) were purchased from Sigma Aldrich, U.S.A. Proteinase-K and DNase free RNase A were purchased from Bangalore Genei, India.

Cell Culture:

The human Cancer Cell lines were obtained either from National Center for Cell Science, Pune, India or National Cancer Institute, Frederick, U.S.A. The human cancer cell colon: SW-620, prostrate, PC-3, DU-145 and acute lymphoblastic leukemia (MOLT-4) were grown and maintained in RPMI-1640 medium, pH 7.4, HEP-2. The media were supplemented with FCS (10%), penicillin (100 Units/ml), streptomycin (100 μg/ml) and glutamine (2 mM) and cells were grown in $CO_2$ incubator (Hera cell, Heraeus, USA) at 37° C. with 90% humidity and 5% $CO_2$.

Results and Discussion:

The DNA Cell cycle studies (FIG. 3) indicated concentration dependent increase in MOLT-4 cells Sub $G_1$ population. The Sub $G_1$ population cells were 6.58%, 33.09%, 33.2% and 55% when "Compound-17" concentration was 1, 10 and, 50 100 μM respectively. The dose dependent increase in MOLT-4 cells Sub $G_1$ cell population with "Compound-17" cells indicates that "Compound-17" induces apoptosis. Compound-17 has also shown complete blockage of $G_1$ phase of cell cycle at 100 µM concentration. DNA fragmentation is the net result of apoptosis, which is observed at the late stage. In the present study it was also studied and the characteristics DNA ladder was observed at 10, 50 & 100 µM of "Compound-17".

In vivo Anticancer Activity

Animal Care and Housing

Non-inbred swiss albino mice from an in-house colony were used in the present study. The breeding and experimental animals were housed in standard size polycarbonate cages providing internationally recommended space for each animal. Animals were fed balanced mice feed supplied by MIs Ashirwad Industries, Chandigarh (India) and autoclaved water was available ad libitum. Animals were cared as per the guide for the care and use of laboratory animals (1996), ILAR, Washington D.C. They were housed in controlled conditions of temperature (23±2° C.), humidity (50-60%) and 12:12 hrs of light: dark cycle. The study and the number of animals used were approved by the institutional animal ethics committee, IIIM, Jammu, India. The study was conducted as per the protocols of National Cancer Institute (NCI), USA (Geran et al., 1972).

Anti Tumor Activity of Parthenin and its Derivative Compound-17 on Ehrlich Ascites Tumor (EAT).

Parthenin and its derivative Compound-17 were evaluated against solid Ehrlich Ascites Tumor (EAT) models at different doses. A standard procedure for experiment was as followed:

Animals of the same sex weighing 20±3 g were injected $1 \times 10^7$ cells collected from the peritoneal cavity of non-inbred swiss mice, bearing 8-10 days old tumor cells, into the right thigh, intramuscularly (on Day 1). On next day animals were randomized and divided into test groups (7 animals in each test group) and one tumor control group (10 animals). Test groups were treated with different doses of Parthenin (10 mg/kg, 25 mg/kg and 50 mg/kg) and its derivative Compound-17 (10 mg/kg, 25 mg/kg and 50 mg/kg, 100 mg/kg and 200 mg/kg) suspension in 1% gum acacia in, their respective group intraperitonealy for nine consecutive days. Another test group was administered 5-FU @ 22 mg/kg i.p and served as positive control. The tumor contra group was similarly administered normal saline (0.2 ml i.p). The percent tumor growth-inhibition was measured on day 13 with respect to their tumor weight (Geran et al., 1972): Shortest and longest diameters of the tumor mass were measured with the help of vernier caliper and tumor weight (mg) was calculated by using following formula Tumor weight (mg)=Length (mm)×(Width (mm)²/2

The average tumor weight for each group was calculated and the percent tumor growth inhibition in treated groups was calculated as follows:

% Tumor Growth Inhibition=100×(Average tumor weight of control group−Average tumor weight of test group)/Average tumor weight of control group Anti Tumor Activity of Parthenin and its Derivative Compound-17 on Ehrlich Ascites Carcinoma (EAC)

Ehrlich Ascites Carcinoma (EAC) was propagated by transplanting $1 \times 10^7$ cells from an animal bearing 8-10 days old Ehrlich Ascites Carcinoma, into the peritoneal cavity of non-inbred swiss mice. For testing, mice of the same sex weighing 20 ±3 g bearing ascites tumor were selected. $1 \times 10^7$ cells obtained from an animal bearing 8-10 days old ascites tumor were injected into peritoneal cavity of all animals used for testing (0 Day). On next day animals were randomized and divided into test groups (7 animals in each test group) and one tumor control group (10 animals). Test groups were treated with different doses of Parthenin (10 mg/kg, 25 mg/kg and 50 mg/kg) and its derivative Compound-17 (10 mg/kg, 25 mg/kg and 50 mg/kg, 100 mg/kg and 200 mg/kg) suspension in 1% gum acacia in their respective group intraperitonealy for nine consecutive days. Another test group was administered 5 FU @ 20 mg/kg i.p and served as positive control. The tumor control group was similarly administered normal saline (0.2 ml i.p). The percent tumor growth inhibition were measured on day 12 with respect to volume of ascitic fluid and the number of tumor cells in the ascitic fluid of peritoneal cavity (Geran et al., 1972; Singh et al., 2007).

The percent tumor growth inhibition was calculated as follow.

% growth inhibition=100×(Average no. of cells in control group−Average no. of cells in test group)/Average no. of cells in control group Results:

Solid tumor bearing mice treated with different doses of Parthenin and its derivative Compound-17 exhibited dose dependent tumor growth inhibition against EAT tumor model. A highly significant (p<0.01) tumor growth inhibition up to 35.11% was observed in EAT bearing mice treated with Parthenin derivative Compound-17 at 100 mg/kg i.p. dose whereas 200 mg/kg i.p. dose induced mortality of all the test animals by fourth day of the treatment. A high level of toxicity without significant antitumor activity was recorded in Parthenin treated groups as it caused mortality of all the animals by second and third day of treatment at 25 and 50 mg/kg i.p. doses respectively (Table 5).

In case of EAC bearing mice same pattern of dose dependent tumor growth inhibition and toxicity was exhibited by both Parthenin and its derivative Compound-17. At 100 mg/kg, i.p. dose of Compound-17 exhibited highly significant (p<0.01) tumor growth inhibition upto 60.50% and its higher dose 200 mg/kg i.p. induced mortality of all the test animals by fourth day of the treatment. In this experiment also Parthenin induced mortality of all the test animals by $2^{nd}$ and $3^{rd}$ day of the parthenin treatment at 25 and 50 mg/kg i.p. doses respectively exhibiting high level of toxicity to the treated animals without any significant antitumor activity (Table 6).

Conclusion:

The present set of data lead us to conclude that the parthenin analogues prepared has the significant cytotoxic potential and they induce concentration dependent apoptosis in cancer cells. Although the mechanism of action of the lead compounds has not been totally established, studies are now underway to determine the exact mechanism of action and to utilize it in an effort to modify our compound to obtain more potent compounds.

From all the discussion we may conclude the SAR of parthenin as:

Spiro derivative of parthenin prepared in this study were screened for their cytotoxicity against three different cancer cell lines. Comparison of the $IC_{50}$ value for the cytotoxicity of the compounds listed in table 2 disclosed the SAR: of the molecule, that the □,□-unsaturated ketonic moiety in parthenin shows remarkable effect on cytotoxicity since reduction of this α,β-unsaturated ketonic moiety results in almost total loss of cytotoxicity. Modification of the α-methylene-γ-butyrolactone by dipolar cycloaddition reaction of nitrile oxide, nitrone and azide on exocyclic double bond of Parthenin yields compounds, which are having appreciable activity as compared to parent molecule (I). Few spiro derivatives of Parthenin have been found to have better activity than parent compound. Thus, the exocyclic double bond has been advantageously utilized to incorporate the lipophilic moieties or nitrogen heterocycle on to the framework to enhance the cytotoxicity of the parent molecule.

Experimental Section

Following examples are given by way of illustration and should not construed the scope of the invention.

General: Melting points were recorded on Buchi Melting point apparatus D-545; IR spectra (KBr discs) were recorded on Balker Vector 22 instrument. NMR spectra were recorded on Bruker DPX200 instrument in $CDCl_3$ with TMS as internal standard for protons and solvent signals as internal standard for carbon spectra. Chemical shift values were mentioned in δ (ppm) and coupling constants are given in Hz. Mass spectra were recorded on RIMS (Shimadzu) and ESI-esquire3000 Bruker Daltonics instrument. The progress of all reactions was monitored by TLC on 2×5 cm pre-coated silica gel 60 F254 plates of thickness of 0.25 mm (Merck). The chromatograms were visualized under UV 254-366 nm and iodine. THF was distilled over benzophenone ketyl-sodium. Metals used for the reactions were purchased from Aldrich.

Synthesis of Spiroisoxazoline Derivative of Parthenin

Compound-1: To a solution of 4-Methoxy-benzonitrile N-oxide (1.5 mmol) in THF (10 ml) stirred over a period of 10 min, maintaining the temperature between 0-5° C., parthenin (1 mmol) was added and the reaction mixture was stirred at same temperature for 20 min followed by stirring at ambient temperature for 2 h. The solvent was evaporated in vaccuo and the crude was subjected for column chromatography. The pure product was characterized on the basis of $^1$HNMR, $^{13}$CNMR, and mass spectrometry.

A colorless solid, M.p. 232.1° C.; $[\alpha]_{13}^{25}$ −14.1; IR(KBr, cm$^{-1}$): 1606, 1724, 1776, 2869, 2942, 3404. $^1$H NMR (CDCl$_3$): δ 1.13 (d, 3H, J=7.6 Hz), 1.36 (s, 3H), 1.40-4.77 (m, 4H), 1.79-2.39 (m, 2H), 3.14-3.20 (q, 1H), 3.35-3.44 (d, 1H, J=16.9 Hz), 3.59-3.67 (d, 1H; J=16.9 Hz), 3.84 (s, 3H), 5.22 (d, 1H, J=5.5 Hz), 6.23 (d, 1H, J=5.8 Hz), 6.9 (d, 2H, J=8.8 Hz), 7.51 (d, 1H, J=5.8 Hz), 7.61 (d, 2H, J=8.8 Hz); $^{13}$C NMR (125 MHz, CDCl$_3$): δ18.0, 20.2, 21.8, 31.6, 36.9, 40.0, 55.5, 59.0, 80.6, 84.1, 90.1, 90.5, 114.5, 121.1, 128.7, 131.1, 132.3, 151.3, 156.8, 161.8, 165.1, 174.4, 212.4; ESIMS: 434 (M+Na), Elemental analysis calcd. for $C_{23}H_{25}NO_6$ C=67.14, H=6.12, N=3.40. Found. C=67.09, H=6.02, N=3.32%.

Compound 2: To a solution of 4-Chloro-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 30 min followed by stirring at ambient temperature for 2.5 h. The solvent was evaporated in vaccuo and the crude was subjected for column chromatography. The pure product was characterized on the basis of $^1$HNMR, $^{13}$CNMR, and mass spectrometry. A light yellow colored solid, M.p. 138.2° C.; $[\alpha]_D^{25}$ −13; IR (KBr, cm$^{-1}$): 1598, 1722, 1776, 2874, 2928, 3441. $^1$H NMR (CDCl$_3$): 5.12 (d, 3H, J=7.6 Hz), 1.34 (s, 3H), 1.51-1.91 (m, 4H), 2.21-2.43 (m, 2H), 3.15-3.24 (q, 1H), 3.34-3.43 (d, 1H, J=17 Hz), 354-3.63 (d, 1H, J=17 Hz), 5.38 (d, 1H, J=5.4 Hz), 6.21 (d, 1H, J=5.9 Hz), 7.30 (d, 2H, J8.6), 7.51 (d, 1H, J=5.9 Hz), 7.61 (d, 1H, J=8.6 Hz); $^{13}$C NMR (125 MHz, CDCl$_3$): δ 18.0, 20.0, 21.4, 31.3, 36.2, 39.9, 48.9, 58.9, 77.6, 79.9, 84.5, 90.4, 127.0, 128.0, 129.0, 131.9, 136.6, 155.5, 163.7, 171.3, 210.8; ESIMS: 434.5 (M+Na), Elemental analysis calcd. for $C_{22}H_{22}ClNO_5$ C=63.53, H=5.33, N=3.37. Found. C=63.47, H=5.30, N=3.31%.

Compound 3: To a solution of 2-Bromo-benzonitrile N-oxide (1.3 mmol) in THF (10 ml) stirred over a period of 15 min, maintaining the temperature between 0-5° C., parthenin (1 mmol) was added and the reaction mixture was stirred at same temperature for 25 min followed by stirring at ambient temperature for 2 h. The solvent was evaporated in vaccuo and the crude was subjected for column chromatography. The pure product was characterized on the basis of $^1$HNMR, $^{13}$CNMR, and mass spectrometry. A light brown colored solid, M.p. 210.4° C.; $[\alpha]_D^{25}$ −20.5; IR (KBr, cm$^{-1}$): 1597, 1721, 1759, 2856, 2924, 3490. $^1$H NMR (CDCl$_3$): δ.12 (d, 3H, J=7.9 Hz), 1.34 (s, 3H), 1.58-2.03 (m, 4H), 2.06-2.75 (m, 2H), 3.17-3.20 (q, 1H), 3.41-3.51 (d, 1H, J=17 Hz), 3.59-3.70 (d, 1H, J=17 Hz), 5.21 (d, 1H, J=5.5 Hz), 6.23 (d, 1H, J=5.9 Hz), 7.21-7.39 (m, 2H), 7.51-7.63 (m, 3H); $^{13}$C NMR (125 MHz, CDCl$_3$): δ 17.6, 18.8, 29.3, 30.3, 46.5, 56.3, 66.7, 77.1, 78.9, 81.4, 88.4, 88.7, 119.1, 127.8, 128.3, 130.0, 131.9, 133.6, 152.5, 163.8, 171.2, 209.4; ESIMS: 483 (M+Na), Elemental analysis calcd. for $C_{22}H_2BrNO_5$ C=57.40, H=4.78; N=17.36. Found. C=57.34, H=4.78, N=17.30%.

Compound 4: To a solution of 4-Dimethylamino-benzonitrile N-oxide (1.3 mmol) in THF (10 ml) stirred over a period of 15 min, maintaining the temperature between 0-5° C., parthenin (1 mmol) was added and the reaction mixture was stirred at same temperature for 25 min followed by stirring at ambient temperature for 3 h. The solvent was evaporated in vaccuo and the crude was subjected for column chromatography. The pure product was characterized on the basis of $^1$HNMR, $^{13}$CNMR, and mass spectrometry. A colorless solid, M.p. 295.6° C.; $[\alpha]_D^{25}$ −32.8; IR (KBr, cm$^{-1}$): 1539, 1599, 1717, 1778, 2872, 2957, 3413. $^1$H NMR (Acetone): δ 1.16 (d, 3H, J=7.7 Hz), 1.31 (s, 3H), 1.72-2.04 (m, 4H), 2.06-2.48 (m, 2H), 2.89 (s, 6H) 3.18-3.25 (q, 1H), 3.50-3.59 (d, 1H, J=17.3 Hz), 3.72-3.81 (d, 1H, J=17.3 Hz), 5.12 (d, 1H, J=5.6 Hz), 6.18 (d, 1H, J=5.9 Hz), 7.19 (d, 1H, J=8.5 Hz), 7.62-7.73 (m, 5H); $^{13}$C NMR (125 MHz, DMSO-d$_6$): δ 18.1, 19.9, 21.1, 22.5, 26.8, 31.6, 38.7, 40.3, 49.0, 58.5, 80.2, 83.7, 90.5, 129.3, 133.6, 135.9, 142.3, 152.2, 166.0, 173.8, 211.6; ESIMS: 437 (M+Na), Elemental analysis calcd. for $C_{24}H_{25}N_2O_5$ C=67.93, H=6.65, N=6.60. Found. C=67.88, H=6.62, N=6.51%.

Compound 5: To a solution of 4-Hydroxy-benzonitrile N-oxide (1.5 mmol) in DCM (10 ml) stirred over a period of 15 min, maintaining the temperature between 0-5° C., parthenin (1 mmol) was added and the reaction mixture was stirred at same temperature for 25 min followed by stirring at ambient temperature for 2.5 h. The solvent was evaporated in vaccuo and the crude was subjected for column chromatography. The pure product was characterized on the basis of $^1$HNMR, $^{13}$CNMR, and mass spectrometry. A light brown colored solid, M.p. 129.2° C.; $[\alpha]_D^{25}$ −30.8; IR (KBr, cm$^1$): 1561, 1599, 1719, 1775, 2927, 2961, 3435. $^1$H NMR (CDCl$_3$): 8.15 (d, 3H, J=7.6 Hz), 1.43 (s, 3H), 1.61-2.10 (m, 4H), 2.17-2.43 (m, 2H), 3.19-3.29 (q, 1H), 3.36-3.46 (d, 1H, J=17.5 Hz), 3.67-3.76 (d, 1H, J=17.5 Hz), 5.10 (d, 1H, J=5.5 Hz), 6.12 (d, 1H, J=5.8 Hz), 6.91 (d, 1H, J=5.8 Hz), 7.35 (d, 2H, J=6 Hz), 7.47-7.51 (d, 2H, J=6 Hz); $^{13}$C NMR (125 MHz, CDCl$_3$): δ 17.5, 19.8, 20.2, 27.3, 31.0, 38.1, 40.0, 47.2, 57.9, 80.2, 83.1, 91.1, 126.8, 129.7, 131.6, 131.9, 133.5, 153.6, 170.8, 173.3, 211.1; ESIMS: 397, Elemental analysis calcd. for $C_{22}H_{23}NO_6$ C=66.49, H=5.83, N=3.52. Found. C=66.52, H=5.76, N=3.48%.

Compound 6: To a solution of 2-Nitro-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 20 min followed by stirring at ambient temperature for 3 h. The solvent was evaporated in vaccuo and the crude was subjected for column chromatography. The pure product was characterized on the basis of $^1$HNMR, $^{13}$CNMR, and mass spectrometry. A yellow colored solid, M.p. 265.0° C.; $[\alpha]_D^{25}$ −22.4; IR (KBr, cm$^{-1}$): 1561, 1590, 1721, 1779, 2922, 2961, 3440. $^1$H NMR (Acetone): δ 1.15 (d, 3H, J=7.6 Hz), 1.33 (s, 3H), 1.57-2.10 (m, 4H), 2.14-2.40 (m, 2H), 3.15-3.26 (q, 1H), 3.38-3.45 (d, 1H, J=17.4 Hz), 3.57-3.66 (d, 1H, J=17.4 Hz), 5.11 (d, 1H, J=5.5 Hz), 6.02 (d, 1H, J=5.9 Hz), 7.70 (d, 1H, J=5.9 Hz), 7.78-7.85 (m, 3H), 8.07 (d, 1H, J=7.2 Hz); $^{13}$C NMR (125 MHz, CDCl$_3$): δ 17.5, 19.3, 20.2, 30.5, 37.4, 39.9, 48.4, 57.9, 77.3, 79.0, 83.1, 90.5, 122.1, 123.2, 124.2, 130.0, 131.5, 132.9, 165.5, 172.7, 211.1; ESIMS: 426, Elemental analysis calcd. for $C_{22}H_{22}N_2O_7$ C=61.97, H=5.20, N=6.57. Found. C=61.90, H=5.23, N=6.51%.

Compound 7: To a solution of 3,5-Dihydroxy-benzonitrile N-oxide (1.5 mmol) in DCM (10 ml) stirred over a period of 15 min; maintaining the temperature between 0-5° C., parthenin (1 mmol) was added and the reaction mixture was stirred at same temperature for 20 min followed by stirring at ambient temperature for 1.5 h. The solvent was evaporated in vaccuo and the crude was subjected for column chromatography. The pure product was characterized on the basis of $^1$HNMR, $^{13}$CNMR, and mass spectrometry. A brownish colored solid, M.p. 135.0° C.; $[\alpha]_D^{25}$ +10.9; IR (KBr, cm$^{-1}$): 1516, 1601, 1722, 1778, 2931, 3436. $^1$H NMR (CDCl$_3$): δ 1.13 (d, 3H, J=7.7 Hz), 1.35 (s, 3H), 1.36-1.92 (m, 4H), 2.37-2.41 (m, 2H), 3.06-3.17 (q, 1H), 3.34-3.43 (d, 1H, J=16.9 Hz), 3.48 (s, 3H), 3.55-3.63 (d, 1H, J=16.9 Hz), 5.21 (d, 1H; J=5.5 Hz), 6.21 (d, 1H; J=5.8 Hz), 7.35 (d, 2H, J=8.5 Hz), 7.52-7.59 (m, 3H); $^{13}$C NMR (125 MHz, CDCl$_3$): δ 18.0, 20.0, 21.4, 21.6, 31.3, 36.2, 40.0, 49.0, 58.9, 79.8, 84.6, 90.4, 127.1, 128.1, 129.0, 132.0, 136.6, 154.9, 163.5, 173.2, 210.5; ESIMS: 427, Elemental analysis calcd. for $C_{23}H_{25}NO_7$ C=64.62, H=5.89, N=3.27. Found. C=64.56, H=5.87, N=3.21%.

Compound 8: To a solution of 3,4-Dimethoxy-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 20 min followed by stirring at ambient temperature for 2.5 h. The solvent was evaporated in vaccuo and the crude was subjected for column chromatography. The pure product was characterized on the basis of $^1$HNMR, $^{13}$CNMR, and mass spectrometry. A light brown colored solid, M.p. 151.0° C.; $[\alpha]_D^{25}$ −10.9; Ir (KBr, cm$^{-1}$): 1570, 1602, 1718, 1760 2886, 2943, 3494. $^1$H NMR (CDCl$_3$): δ 1.15 (d, 3H, J=7.6 Hz), 1.38 (s, 3H), 1.66-2.04 (m, 4H), 2.17-2.38 (m, 2H), 3.12-3.21 (q, 1H), 3.36-3.45 (d, 1H, J=16.8 Hz), 3.61-3.69 (d, 1H, J=16.8 Hz), 3.92 (s, 6H), 5.25 (d, 1H, J=5.6 Hz), 6.28 (d, 1H, J=5.9 Hz), 6.80 (m, 1H), 7.01 (m, 1H), 7.37 (m, 1H), 7.51 (d, 1H, J=5.9 Hz); $^{13}$C NMR (125 MHz, CDCl$_3$): δ 17.8, 19.5, 20.1, 21.2, 313, 38.6, 40.5, 49.2, 57.5, 58.5, 80.3, 83.5, 92.7, 127.5, 128.5, 131.1, 131.8, 134.6, 153.5, 164.4, 171.6, 211.3; ESIMS: 432, Elemental analysis calcd. for $C_{24}H_{27}NO_7$ C=65.89, H=5.29, N=3.20. Found. C=65.80, H=5.23, N=3.12%.

Compound 9: To a solution of 4-Hydroxy-3-methoxy-benzonitrile N-oxide (1.5 mmol) in THF (10 ml) stirred over a period of 15 min, maintaining the temperature between 0-5° C., parthenin (1 mmol) was added and the reaction mixture was stirred at same temperature for 20 min followed by stirring at ambient temperature for 3 h. The solvent was evaporated in vaccuo and the crude was subjected for column chromatography. The pure product was characterized on the basis of $^1$HNMR, $^{13}$CNMR, and mass spectrometry. A colorless solid; IR(KBr, cm$^{-1}$): 1561, 1590, 1721, 1779, 2922, 2961, 3440. $^1$H NMR (CDCl$_3$): δ 1.14 (d, 3H, J=7.6 Hz), 1.38 (s, 3H), 1.57-2.05 (m, 4H), 2.07-2.40 (m, 2H), 3.24-3.32 (q, 1H), 3.36-3.45 (d, 1H, J=17 Hz), 3.67-3.76 (d, 1H, J=17 Hz), 5.31 (d, 1H, J=5.5 Hz), 6.31 (d, 1H, J=5.6 Hz), 7.35 (d, 1H, J=5.6 Hz), 7.52-7.59 (m, 3H); $^{13}$C NMR (125 MHz, CDCl$_3$): δ 18.0, 20.0, 21.4, 21.6, 31.3, 36.2, 40.0, 49.0, 58.9, 77.8, 79.8, 84.6, 90.4, 127.1, 128.1, 132.0, 134.5, 136.6, 154.9, 163.5, 173.2, 210.5; ESIMS: 413 Elemental analysis calcd. for $C_{22}H_{23}NO_7$ C=63.91, H=5.60, N=3.38. Found. C=63.85, H=5.61, N=3.30%.

Compound 10: To a solution of 1H-Indole-2-carbonitrile N-oxide (1.5 mmol) in THF (10 ml) stirred over a period of 15 min, maintaining the temperature between 0-5° C., parthenin (1 mmol) was added and the reaction mixture was stirred at same temperature for 15 min followed by stirring at ambient temperature for 1.5 h. The solvent was evaporated in vaccuo and the crude was subjected for column chromatography. The pure product was characterized on the basis of $^1$HNMR, $^{13}$CNMR, and mass spectrometry. A yellowish colored solid; IR(KBr, cm$^{-1}$): 1561, 1594, 170.19, 1775, 2921, 2970, 3449. $^1$H NMR (CDCl$_3$): δ 1.13 (d, 3H, J=7.6 Hz), 1.37 (s, 3H), 1.51-2.01 (m, 4H), 2.03-2.40 (m, 2H), 3.23-3.31 (q, 1H), 3.37-3.46 (d, 1H, J=17.2 Hz), 3.66-3.77 (d, 1H, J=17.2 Hz), 5.27 (d, 1H, Hz), 6.02 (d, 1H, J=5.9 Hz), 6.79-6.83 (m, 2H), 6.95 (d, 1H, J=8 Hz), 7.06 (d, 1H, J=8 Hz), 7.31 (s, 1H), 7.26 (d, 1H, J=5.9 Hz); $^{13}$C NMR (125 MHz, CDCl$_3$); δ 17.8, 19.7, 21.0, 21.2, 30.3, 38.5, 41.5, 50.2, 58.4, 80.1, 83.7, 90.7, 127.5, 128.2, 131.5, 131.9, 134.2, 136.0, 136.9, 153.5, 164.3, 172.6, 175.2, 211.0; ESIMS: 420, Elemental analysis calcd. for $C_{24}H_{24}N_2O_5$ C=68.56, H=5.75, N=6.66. Found. C=68.60, H=5.66, N=6.58%.

Compound 11: To a solution of 3-Nitro-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 25 min followed by stirring at ambient temperature for 1.5 h. The solvent was evaporated in vaccuo and the crude was subjected for column chromatography. The pure product was characterized on the basis of $^1$HNMR, $^{13}$CNMR, and mass spectrometry. A yellowish colored solid; IR(KBr, cm$^{-1}$): 1570, 1591, 1725, 1778, 2919, 2966, 3445. $^1$H NMR (CDCl$_3$): δ 1.16 (d, 3H, J=7.7 Hz), 1.30 (s, 3H), 1.76-2.04 (m, 4H), 2.17-2.41 (m, 2H), 3.14-3.24 (q, 1H), 3.44-3.53 (d, 1H, J=16.9 Hz), 3.65-3.74 (d, 1H, J=16.9 Hz), 5.27 (d, 1H, J=5.5 Hz), 6.29 (d, 1H, J=5.9 Hz), 7.53 (d, 1H, J=5.9 Hz), 7.58-7.66 (m, 1H), 8.12 (d, 1H, J=7.8 Hz), 8.30 (d, 1H, J=8.1), 8.44 (s, 1H); $^{13}$C NMR (125 MHz, CDCl$_3$): δ 17.6, 19.3, 20.2, 26.1, 31.4, 38.4, 40.4, 50.2, 60.5, 81.3, 86.0, 92.4, 126.2, 127.0, 131.2, 131.7, 133.3, 133.7, 156.1, 164.3, 171.6, 211.2; ESIMS: 426, Elemental analysis calcd. for $C_{22}H_{22}N_2O_7$ C=61.91, H=5.20, N=6.57. Found. C=61.89, H=5.13, N=6.47%.

Compound 12: To a solution of thiophene-2-carbonitrile N-oxide (1.2 mmol) in THF (10 ml) stirred over a period of 10 min, maintaining the temperature between 0-5° C., parthenin (1 mmol) was added and the reaction mixture was stirred at same temperature for 20 min followed by stirring at ambient temperature for 2 h. The solvent was evaporated in vaccuo and the crude was subjected for column chromatography. The pure product was characterized on the basis of $^1$HNMR, $^{13}$CNMR, and mass spectrometry. A colorless solid; IR(KBr, cm$^{-1}$): 1559, 1580, 1732, 1780, 2932, 2966, 3460. $^1$H NMR (CDCl$_3$): δ 1.17 (d, 3H, J=7.6 Hz), 1.36 (s, 3H), 1.50-2.27 (m, 4H), 2.36-2.43 (m, 2H), 3.23-3.33 (q, 1H), 3.41-3.50 (d, 1H, J=17 Hz), 3.57-3.65 (d, 1H, J=17 Hz), 5.25 (d, 1H, J=5.5 Hz), 6.31 (d, 1H, J=5.8 Hz), 6.89-7.09 (m, 2H), 7.42 (m, 1H), 7.51

(d, 1H, J=5.8 Hz); $^{13}$C NMR (125 MHz, CDCl$_3$): δ 18.2, 19.6, 20.0, 21.5, 37.5, 41.5, 49.1, 58.4, 81.0, 83.7, 91.6, 128.2, 130.8, 131.5, 134.9, 135.6, 153.4, 165.3, 174.6, 211.3; ESIMS: 387, Elemental analysis calcd. for C$_{20}$H$_{21}$NO$_5$S C=62.00, H=5.46, N=3.62. Found. C=61.95, H=5.40, N=3.60%.

Compound 13: To a solution of 2-Methyl-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 30 min followed by stirring at ambient temperature for 2 h. The solvent was evaporated in vaccuo and the crude was subjected for column chromatography. The pure product was characterized on the basis of $^1$HNMR, $^{13}$CNMR, and mass spectrometry. A light brown colored solid, M.p. 277° C.; IR(KBr, cm$^{-1}$): 1561, 1590, 1721, 1779, 2922, 2961, 3440. $^1$H NMR (CDCl$_3$): δ 1.14 (d, 3H, J=7.7 Hz), 1.37 (s, 3H), 1.41-2.04 (m, 4H), 2.27-2.36 (m, 2H), 2.38 (s, 3H), 3.12-3.21 (q, 1H), 3.37-3.46 (d, 1H, J=16.8 Hz), 3.62-3.70 (d, 1H, J=16.8 Hz), 5.24 (d, 1H, J=5.5 Hz), 6.21 (d, 1H, j=5.9 Hz), 7.31 (d, 1H, J=5.9), 7.41 (s, 1H), 7.48-7.53 (m, 3H); $^{13}$C NMR (125 MHz, CD$_3$OD): δ 16.9, 19.2, 20.0, 21.1, 22.8, 31.2, 35.9, 39.8, 40.5, 49.2, 58.7, 80.2, 83.7, 90.1, 127.1, 128.4, 130.8, 131.5, 138.5, 153.2065.3, 171.6, 211.1; ESIMS: 411, Elemental analysis calcd. for C$_{23}$H$_{25}$NO$_5$ C=69.86, H=6.37, N=3.54. Found. C=69.80, H=6.32, N=3.50%.

Compound-14: To a solution of 3-Methyl-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 35 min followed by stirring at ambient temperature for 2 h. The solvent was evaporated in vaccuo and the crude was subjected for column chromatography. The pure product was characterized on the basis of $^1$HNMR, $^{13}$CNMR, and mass spectrometry. A colorless solid, M.p. 183° C.; [α]$_D^{25}$ −68; IR(KBr, cm$^{-1}$): 1561, 1590, 1721, 1779, 2922, 2961, 3440. $^1$H NMR (CDCl$_3$): δ 1.13 (d, 3H, J=7.7 Hz), 1.36 (s, 3H), 1.78-2.42 (m, 4H), 2.43-2.53 (m, 2H), 2.54 (s, 3H), 2.55-2.89 (q, 1H), 3.42-3.50 (d, 1H, J=16.9 Hz), 3.64-3.72 (d, 1H, J=16.9 Hz), 522 (d, 1H, J=5.5 Hz), 6.23 (d, 1H, J=5.7 Hz), 7.26-7.47 (m, 3H), 7.37 (d, 1H, J=53 Hz); $^{13}$C NMR (125 MHz, CDCl$_3$): δ 18.0, 20.0, 21.5, 22.8, 31.4, 38.9, 40.1, 49.0, 59.0, 79.6, 84.7, 89.0, 125.8, 127.7, 128.8, 129.8, 131.6, 132.3, 138.3, 157.1, 163.1, 173.3, 210.1; ESIMS: 411, Elemental analysis calcd. for C$_{23}$H$_{25}$NO$_5$ C=69.86, H=6.37, N=3.54. Found. C=69.81, H=6.27, N=3.48%.

Compound 15: To a solution of 4-Fluoro-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 25 min followed by stirring at ambient temperature for 2.5 h. The solvent was evaporated in vaccuo and the crude was subjected for column chromatography. The pure product was characterized on the basis of $^1$HNMR, $^{13}$CNMR, and mass spectrometry. A colorless solid, M.p. 193° C.; [α]$_D^{25}$ −54°; IR (KBr, cm$^{-1}$): 1513, 1602, 1717, 1776, 2876, 2965, 3434. $^1$H NMR (CDCl$_3$): δ 1.13 (d, 3H, J=7.6 Hz), 1.36 (s, 3H), 1.59-2.04 (m, 4H), 2.28-2.40 (m, 2H), 3.18-3.21 (q, 1H), 3.36-3.44 (d, 1H, J=16.9 Hz), 3.57-3.66 (d, 1H, J=16.9 Hz), 5.22 (d, 1H, J=5.5 Hz), 6.20 (d, 1H, J=5.9 Hz), 7.04-7.13 (m, 2H), 7.52 (d, 1H, J=5.9 Hz), 7.62-7.69 (m, 2H); $^{13}$C NMR (125 MHz, CDCl$_3$): δ 18.0, 20.0, 21.4, 31.4, 31.5, 34.2, 36.4, 40.5, 49.1, 59.0, 79.6, 84.7, 90.2, 115.9, 116.0, 128.8, 128.9, 132.4, 137.3, 155.2, 163.0, 210.5; ESIMS: 399, Elemental analysis calcd. for C$_{22}$H$_{22}$FNO$_5$ C=66.16, H=5.55, N=3.51. Found. C=66.10, H=5.51, N=3.44%.

Compound 16: To a solution of 4-Cyano-benzonitrile N-oxide (1.2 mmol) in THF (10 ml) stirred over a period of 10 min, maintaining the temperature between 0-5° C., parthenin (1 mmol) was added and the reaction mixture was stirred at same temperature for 25 min followed by stirring at ambient temperature for 2.5 h. The solvent was evaporated in vaccuo and the crude was subjected for column chromatography. The pure product was characterized on the basis of $^1$HNMR, $^{13}$CNMR, and mass spectrometry. A yellowish colored solid, M.p. 147° C.; IR(KBr, cm$^{-1}$): 1631, 1720, 1776, 2875, 2927, 3461. $^1$H NMR (CDCl$_3$): δ 1.14 (d, 3H, J=7.6 Hz), 1.37 (s, 3H), 1.40-2.04 (m, 4H), 2.17-2.41 (m, 2H), 3.16-3.24 (q, 1H), 3.38-3.46 (d, 1H, J=16.9 Hz), 3.60-3.68 (d, 1H, J=16.9 Hz), 5.24 (d, 1H, J=5.5 Hz), 6.26 (d, 1H, J=5.9 Hz), 7.53 (d, 1H, J=5.9 Hz), 7.68-7.85 (m, 4H); $^{13}$C NMR (125 MHz, CDCl$_3$): δ 16.9, 18.0, 20.0, 20.3, 21.4, 31.3, 31.8, 35.8, 40.0, 49.9, 58.9, 79.9, 80.4, 84.6, 91.1, 113.9, 118.1, 127.5, 128.6, 132.82132.1, 132.9, 155.1, 163.4, 172.9, 210.4; ESIMS: 406, Elemental analysis calcd. for C$_{23}$H$_{22}$N$_2$O$_5$ C=67.97, H=5.46, N=6.89. Found. C=67.91, H=5.40, N=6.85%.

Compound-17: To a solution of anthracene nitrile oxide (1.2 mmol) in THF (10 ml) stirred over a period of 10 min, maintaining the temperature between 0-5° C., parthenin (1 mmol) was added and the reaction mixture was stirred at same temperature for 20 min followed by stirring at ambient temperature for 2 h. The solvent was evaporated in vaccuo and the crude was subjected for column chromatography. The pure product was characterized on the basis of $^1$HNMR, $^{13}$CNMR, and mass spectrometry.

A colorless solid, M.p. 162° C.; IR(KBr, cm$^{-1}$): 1593, 1626, 1722, 1774, 2870, 2926, 3442. $^1$H NMR (CDCl$_3$): δ 1.12 (d, 3H, J=7.6 Hz), 1.39 (s, 3H), 1.46-1.80 (m, 4H), 2.17-2.41 (m, 2H), 3.37-3.39 (q, 1H), 3.44-3.53 (d, 1H, J=17.8 Hz), 3.73-3.82 (d, 1H, J=17.8 Hz), 5.36 (d, 1H, J=5.5 Hz), 6.20 (d, 1H, J=5.7 Hz), 7.36-7.61 (m, 5H), 8.02 (d, 2H, J=8 Hz), 8.15 (d, 2H, J=8 Hz), 8.54 (s, 1H) $^{13}$C NMR (125 MHz, CDCl$_3$): δ 18.3, 20.4, 22.1, 31.0, 40.4, 41.2, 49.2, 60.2, 71.2, 78.1, 83.4, 86.8, 90.1, 124.0, 126.9; 127.5, 128.4, 129.6, 130.1, 130.4, 131.5, 132.3, 154.2, 163.6, 164.3, 168.6, 212.0; ESIMS: 481, Elemental analysis calcd. for C$_{30}$H$_{27}$NO$_5$ C=74.83%, H=5.65%, N=2.91%. Found. C=74.80%; H=5.60%, N=2.89%.

Synthesis of Spiroisoxazolidine Derivatives of Parthenin:

Compound 18: To a solution of Parthenin (1 equivalent) in dry benzene, was added N-[4-chlorophenyl]-α-phenyl nitrone (1.5 equivalent). The reaction mixture was refluxed for 8 hours. The solvent was evaporated in vaccuo and the crude was subjected to column chromatography. The pure product was characterized on the basis of $^1$H/$^{13}$C-NMR, and mass spectrometry: Pale yellow color solid, M.p. 183° C.; [α]D25 +70.58; I.R (KBr, cm$^{-1}$): 3450, 2963, 2910.2, 1751.5, 1594, 1366.8, 1220.1, 1070.9. $^1$H NMR (CDCl3): δ 7.5-7.15 (m, 7H), 6.96-6.83 (m, 3H), 6.27 (d, J=5.84 Hz, 1H), 5.26 (d, J=5.38 Hz 1H), 5.18 (1, J=8.07 Hz 1H), 3.25-3.1 (m, 1H), 3.05-2.9 (m, 1H), 2.47-1.6 (m, 6H), 1.18 (s, 3H), 1.11 (d, J=7.73 Hz, 3H); $^{13}$C NMR (125 MHz, CDCl3): δ 18.41, 20.47, 22.00, 30.11, 40.53, 43.20, 49.73, 60.00, 70.33, 79.92, 85.00, 87.00, 115.31, 118, 122.90, 128.40, 129.25, 132.49, 140.00, 152.00, 164.01, 175.00, 211.00; ESIMS: 494.1 (M+1). Elemental analysis calcd. for C$_{28}$H$_{28}$ClNO$_5$ C=68.08%, H=5.71%, N=2.84%. Found. C=68.12%, H=5.60%, N=2.89%.

Compound 19: To a solution of Parthenin (1 equivalent) in dry benzene, was added N-[2-methylphenyl]-α-phenyl nitrone (1.5 equivalent). The reaction mixture was refluxed for 6 hours. The solvent was evaporated in vaccuo and the crude was subjected to column chromatography. The pure product was characterized on the basis of $^1H/^{13}C$-NMR, and mass spectrometry: Pale yellow color solid, M.p. 181° C.; $[\alpha]_D^{25}$ +44.66; I.R (KBr, cm$^{-1}$):3450, 2952.5, 2920.8, 2857.4, 1749.3, 1599.7, 1456.6, 1377.2, 802.2. 1H NMR (CDCl$_3$): δ 7.74-7.71 (m, 1H), 7.50 (d, J=5.89 Hz, 1H), 7.27-7.10 (m, 5H), 6.94-6.81 (m, 3H), 6.27 (d, J=5.9 Hz, 1H), 5.28 (m, 2H), 3.25-3.15 (m, 1H), 3.04-2.95 (m, 1H), 2.7-1.6 (m, 6H), 2.43 (s, 3H), 1.26 (s, 3H), 1.1 (d, J=4.15 Hz, 3H). $^{13}$C NMR (125 MHz, CDCl$_3$): δ 17.93, 19.36, 21.67, 31.40, 40.01, 41.10, 49.25, 58.984, 67.57, 79.50, 84.61, 86.42, 114.25, 117.01, 121.836, 125.98, 126.75, 128.40, 128.73, 130.70, 131.83, 134.60, 151.43, 163.79074.36, 210.96; ESIMS: 474.1 (M+1). Elemental analysis calcd. for $C_{29}H_{31}NO_5$ C=73.55%, H=6.60%, N=2.96%. Found. C=73.60%, H=5.58%, N=2.92%.

Compound 20: To a solution of Parthenin (1 equivalent) in dry benzene, was added N-[4-bromophenyl]-α-phenyl nitrone (1.5 equivalent). The reaction mixture was refluxed for 8 hours. The solvent was evaporated in vaccuo and the crude was subjected to column chromatography. The pure product was characterized on the basis of $^1H/^{13}C$-NMR, and mass spectrometry: Pale yellow color solid, M.p. 185° C.; [α]D25 +91.07; I.R (KBr, cm-1): 3451.68, 2962107, 2925.92, 1774:56, 1754.00, 1722.69, 1596:79, 1488.03, 1011.38, 800.35, 754.89, 713.22. 1H NMR (CDCl3): δ 7.56, 7.39 (m, 5H), 7.28-7.18 (m, 2H), 6.86-6.69 (m, 3H), 6.24 (d, 1H), 5.28 (d, 1H), 5.17 (t, 1H), 3.23-3.12 (m, 1H), 3.0-2.87 (m, 1H), 2.54-1.6 (m, 6H), 1.40 (s, 3H), 1.14 (d, 3H); $^{13}$C NMR. (125 MHz, CDCl3): δ 17.93, 20.09, 21.63, 31.40, 40.04, 42.68, 49.16, 58.97, 69.88, 79.49, 85.16, 86.57, 114.80, 117.66, 122.41, 128.27, 128.43, 131.96, 139.98, 151.04, 164.76, 174.09, 210.74; ESIMS: 540.1 (M+1). Elemental analysis calcd. for $C_{28}H_{28}BrNO_5$ C=62.46%, H=5.24%, N=2.60%. Found. C=62.40%, H=5.26%, N=2.94%.

Compound 21: To a solution of Parthenin (1 equivalent) in dry benzene, was added N-[4-methylphenyl]-α-phenyl nitrone (1.5 equivalent). The reaction mixture was refluxed for 6 hours. The solvent was evaporated in vaccuo and the crude was subjected to column chromatography. The pure product was characterized on the basis of $^1H/^{13}C$-NMR, and mass spectrometry: Brown color solid, M.p. 114° C.; [α]D25 +47.44; I.R (KBr, cm$^{-1}$): 3427.55.68, 3019.21, 2960.26, 2924.93, 1772.74, 1722.05, 1597.57, 1514.07, 1020.43, 756.53; 1H NMR (CDCl3): s 7.47-6.86 (m, 10H), 6.2 (d, J=5.83 Hz, 1H), 5.25 (m, 2H), 3.25-3.12 (m, 1H), 3.0-2.875 (m, 1H), 2.6-1.61 (m, 6H), 2.36 (s, 3H), 1.3 (s, 3H), 1.15 (d, J=3.19 Hz, 3H); $^{13}$C NMR (125 MHz, CDCl3): δ 18.40, 20.01, 21.07, 31.55, 40.04, 43.00, 49.35, 58.98, 70.40, 79.43, 84.57, 86.30, 114.97, 117.53, 122.19; 127.02, 128.29, 129.30, 131.88, 137.51, 151.33, 163.66, 174.36, 210.88. ESIMS: 474.3 (M+1). Elemental analysis calcd. for $C_{29}H_{31}NO_5$ C=73.55%, H=6.60%, N=2.96%. Found. C=73.60%, H=6.58%, N=2.90%.

Compound-22: To a solution of Parthenin (1 equivalent) in dry benzene, was added N-[4-hydroxy-3-nitrophenyl]-α-phenyl nitrone (1.5 equivalent). The reaction mixture was refluxed for 7 hours. The solvent was evaporated in vaccuo and the crude was subjected to column chromatography. The pure product was characterized on the basis of $^1H/^{13}C$-NMR, and mass spectrometry: Yellow color solid, M.p. 167° C.; [α]D25 +74.10; I.R (KBr, cm$^{-1}$): 3571.94, 3512.12, 3377.61, 3059.29, 2945.72, 1757.40, 1703.12, 1539.97, 1486.22, 1339.63, 1240.80, 976.92, 758.45, 696.82. 1H NMR (CDCl3): δ 8.25-6.8 (m, 9H), 6.26 (d, J=5.84 Hz, 1H), 5.25-5.1 (m, 2H), 3.2-3.1 (m, 1H), 3.0-2.85 (m, 1H), 2.5-1.5 (m, 6H), 1.3 (s, 3H), 1.25 (d, J=7.67 Hz, 3H). $^{13}$C NMR 125 MHz, CDCl3): δ 17.97, 19.98, 21.66, 31.67, 40.08, 42.55; 49.171, 58.97, 69.19, 7.9:51, 84.65, 86.58, 115.02; 117.86, 120.75, 122.80, 28.57, 128.87, 131.99, 133:44, 135.95, 150.68, 154.587, 163:47, 174.06, 210.66. ESIMS: 5.19 (M−1). Elemental analysis calcd. for $C_{28}H_{28}N_2O_5$ C=64.61%, H=5.42%, N=5.38%. Found. C=64.58%, H=5.44%, N=5.42%.

Compound 23: To a solution of Parthenin (1 equivalent) in dry benzene; was added N-phenyl-α-phenyl nitrone (1.5 equivalent). The reaction mixture was refluxed for 8 hours. The solvent was evaporated in vaccuo and the crude was subjected to column chromatography. The pure product was characterized on the basis of $^1H/^{13}C$-NMR, and mass spectrometry: Pale yellow color solid, M.p. 170° C.; $[\alpha]_D^{25}$ +116.47. I.R (KBr, cm$^{-1}$): 3410.10, 301268, 2923.80, 1753.32, 1726.45, 1596.79, 1487.14, 1201.64, 974.48, 753.76, 717.70. $^1$H NMR (CDCl$_3$): δ 7.54-7.15 (m, 8H), 7.15-6.87 (m, 3H), 6.18 (d, J=5.86 Hz, 1H), 5.29-5.19 (m, 2H), 3.25-3.15 (m, 2H), 2.96-2.88 (m, 2H), 2.6-1.68 (m, 4H), 1.33 (s, 3H), 1.08 (d, J=3.97 Hz, 3H); $^{13}$C NMR (125 MHz, CDCl$_3$): δ 17.92, 19.98, 21.64, 31.54, 39.95, 41.91, 49.13, 58.94, 70.94, 70.48, 79.10, 84.49, 86.46, 114.72, 117.54, 122.10, 126.49, 127.75, 128.69, 131.67, 140.91, 151.38, 164.00, 174.22, 211.33. ESIMS: 460.2 (M+1); Elemental analysis calcd. for $C_{28}H_{29}NO_5$ C=73.18%, H=6.36%, N=3.05%. Found. C=73.20%, H=6.32%, N=3.09%.

Compound 24: To a solution of Parthenin (1 equivalent) in dry benzene, was added N-[4-fluorophenyl]-α-phenyl nitrone (1.5 equivalent). The reaction mixture was refluxed for 6 hours. The solvent was evaporated in vaccuo and the crude was subjected to column chromatography. The pure product was characterized on the basis of $^1H/^{13}C$-NMR, and mass spectrometry: Pale yellow color solid, M.p. 154° C.; $[\alpha]_D^{25}$ +38.35; I.R (KBr, cm$^{-1}$): 3437.14, 2962.44, 2923.96, 1753.52, 1722.45, 1597.89, 1509.65, 1261.62, 1088.42, 1024.40, 801.63. 1H NMR (CDCl$_3$): δ 7.52-7.45 (m, 3H), 7.28-6.85 (m, 7H), 6.20 (d, J=5.87 Hz 1H), 5.26 (d, J=5.58 Hz, H), J=7.15 Hz, 1H), 3.25-3.12 (m, 1H), 1H), 2.80-1.6 (m, 6H), 1.34 (s, 3H), 1.12 (d, J=3.55 Hz, 3H); $^{13}$C NMR (125 MHz, CDCl$_3$): 18.06, 20.22, 22.70, 29.36, 40.14, 42.88, 49.40, 59.06, 70.00, 79.50, 84.70, 86.47, 115.07, 122.52, 128.24, 128.80, 132.08, 151.14, 163.58, 174.10, 210.75. ESIMS: 478.2 (M+1); Elemental analysis calcd. for $C_{28}H_{28}FNO_5$ C=70.43%, H=5.91%, N=2.93%. Found., C=73.40%, H=5.96%, N=2.90%.

Compound 25: TO a solution of Parthenin (1 equivalent) in dry benzene, was added N-[3-bromo-4-methoxyphenyl]-α-phenyl nitrone (1.5 equivalent). The reaction mixture was refluxed for 6 hours. The solvent was evaporated in vaccuo and the crude was subjected to column chromatography. The pure product was characterized on the basis of $^1H/^{13}C$-NMR, and mass spectrometry: Pale yellow color solid, M.p. 96° C.; $[\alpha]_D^{25}$ +84.44; I.R (KBr, cm$^{-1}$): 3442.92, 2924.86, 1774.12, 1721.68, 1596.72, 1493.09, 1258.31, 1019.69; 715.99. $^1$H NMR (CDCl$_3$): δ 7.73 (d, J=1.88 Hz, 1H), 7.46-6.84 (m, 9H), 6.17 (d, J=5.84 Hz, 1H), 5.24 (d, J=5.56 Hz, 1H), 5.09 (t, 1H), 3.89 (s, 3H), 3.25-3.125 (m, 1H), 2.92-2.82 (m, 2H), 2.47-1.6 (m, 5H), 1.25 (s, 3H), 1.07 (d, J=7.38 Hz, 3H); $^{13}$C NMR (125 MHz, CDCl$_3$): δ 17.99, 20.18, 21.68, 31.77, 40.06, 42.92, 49.16, 56.37, 59.01, 69.68, 79.66, 84.59, 86.53, 112.24, 115.03, 117.72, 122.51, 126.99, 128.48, 131.29, 131.82, 134.31, 151.16, 155.52, 163.93, 174.22, 211.22. ESIMS:

570.2 (M+1). Elemental analysis calcd. for $C_{29}H_{30}BrNO_6$ C=61.27%, H=5.32%, N=2.46%. Found. C=61.30%, H=5.29%, N=2.50%.

Compound 26: To a solution of Parthenin (1 equivalent) in dry benzene, was added N-[4-cyanophenyl]-α-phenyl nitrone (1.5 equivalent). The reaction mixture was refluxed for 7 hours. The solvent was evaporated in vaccuo and the crude was subjected to column chromatography. The pure product was characterized on the basis of $^1H/^{13}C$-NMR, and mass spectrometry: Colorless solid, M.p. 116° C.; $[\alpha]_D^{25}$ +86.90; I.R (KBr, cm$^{-1}$): 3444.38, 2961.88, 2926.46, 2227.78, 1775.62, 1722.78, 1597.46, 1261.25, 1195.57, 102023, 802.05, 757.01, 561.81. 1H NMR (CDCl$_3$): δ 7.71-7.6 (m, 4H), 7.47 (d, J=5.89 Hz, 1H), 7.3-7.12 (m, 2H), 7.0-6.8 (m, 3H), 6.19 (d, J=5.86 Hz, 1H), 5.28-5.19 (m, 2H), 3.25-3.15 (m, 1H), 3.1-2.95 (m, 1H), 2.5-1.6 (m, 6H), 1.25 (s, 3H), 1.1 (d, J=7.54 Hz 311); $^{13}$C NMR (125 MHz, CDCl$_3$): δ 17.89, 19.95, 21.72, 31.52, 39.95, 41.89, 49.00, 58.92, 69.72, 79.60, 84.49, 86.54, 114.35, 118.55, 122.41, 127.27, 128.87, 132.80, 146.68, 150.86, 163.72, 174.123, 210.79. ESIMS: 485.2 (M+1). Elemental analysis calcd. for $C_{29}H_{28}N_2O_5$ C=71.88%, H=5.82%, N=5.78%. Found. C=71.90%, H=5.76%, N=5.82%.

Compound 27: To a solution of Parthenin (1 equivalent) in dry benzene, was added N-[5-bromo-2-methoxyphenyl]-α-phenyl nitrone (1.5 equivalent). The reaction mixture was refluxed for 8 hours. The solvent was evaporated in vaccuo and the crude was subjected to column chromatography. The pure product was characterized on the basis of $^1H/^{13}C$-NMR, and mass spectrometry: Colorless solid, M.p. 197° C.; $[\alpha]_D^{25}$ +100. I.R(KBr, cm$^{-1}$): 3417.42, 2925.64, 2854.68, 1773.88, 1719.72, 1597:14, 1489.39, 1259.35, 1022.69, 812.91, 749.97. $^1$H NMR (CDCl$_3$): δ 7.8 (d, J=2.39 Hz, 1H), 7.49 (d, J=5.89 Hz, 1H), 7.47-7.19 (m, 3H), 6.96-6.79 (m, 4H), 6.26 (d, J=5.89 Hz, 1H), 5.48 (t, J=7.47 Hz, 1H), 5.29 (d, J=5.62 Hz, 1H), 3.88 (s, 3H), 3.19-3.09 (m, 2H), 2.36-1.55 (m, 5H), 1.34 (S, 3H), 1.10 (d, J=7.7 Hz, 3H). $^{13}$C NMR (125 MHz, CDCl$_3$): δ 18.00, 20.0, 21.8, 31.45, 40.16, 49.27, 55.68, 64.81, 79.22, 84.79, 86.71, 112.14, 113.75, 121.68, 128.0, 129.55, 129.92, 131.20, 131.94, 132.25, 151.41, 155.33, 163.28, 174.06, 210.43. ESIMS: 485.2 (M+1). Elemental analysis calcd. for $C_{29}H_{30}BrNO_6$ C=61.27%, H=5.32%, N=2.46%. Found. C=61.30%, H=5.29%, N=2.50%.

Compound 28: To a solution of Parthenin (1 equivalent) in dry benzene, was added N-[2,3-dimethoxyphenyl]-α-phenyl nitrone (1.5 equivalent). The reaction mixture was refluxed for 9 hours. The solvent was evaporated in vaccuo and the crude Was subjected to column chromatography. The pure product was characterized on the basis of $^1H/^{13}C$-NMR, and mass spectrometry: Dark brown color solid, M.p. 99° C.; $[\alpha]_D^{25}$ +41.66; I.R (KBr, cm$^{-1}$): 3543.63, 2992.41, 2962.29, 1764.13, 1724.86, 1597.03, 1508.69, 1207.95, 1031.35, 730.51. 1H NMR (CDCl$_3$): δ 7.55-7.4 (m, 2H), 7.28-7.10 (m, 3H), 6.94-6.86 (m, 2H), 6.5-6.47 (m, 2H), 6.21 (d, J=5.86 Hz, 1H), 5.4 (t, 1H), 5.26 (d, J=5.72 Hz, 1H), 3.86 (s, 3H), 3.8 (s, 3H), 3.125-3.06 (m, 2H), 2.6-1.6 (m, 6H), 1.32 (s, 3H), 1.1 (4, J=4.5 Hz, 3H). $^{13}$C NMR (125 MHz, CDCl$_3$): δ 18.09, 20.05, 21.85, 31.50, 40.18, 49.49, 55.54, 59.11, 61.68, 63.73, 65.08, 79.26, 84.74, 86.63, 104.43, 98.54, 114.18, 116.96, 122.00, 128.73, 129.20, 132.11, 151.67, 149.52, 157.33, 160.37, 163.55, 210.96. ESIMS: 525.8 (M+1). Elemental analysis calcd. for $C_{30}H_{33}NO_7$ C=69.35%, H=6.40%, N=2.70%. Found. C=69.38%, H=6.35%, N=2.75%.

Compound 29: To a solution of Parthenin (1 equivalent) in dry benzene, was added N-[3,4,5-trimethoxyphenyl]-α-phenyl nitrone (1.5 equivalent). The reaction mixture was refluxed for 8 hours. The solvent was evaporated in vaccuo and the crude was subjected to column chromatography. The pure product was characterized on the basis of $^1H/^{13}C$-NMR, and mass spectrometry: Pale yellow color solid, M.p. 119° C.; $[\alpha]_D^{25}$ +63.12; I.R (KBr, cm$^{-1}$): 3418.37, 2935.05, 1755.90, 1724.09, 1594.97, 1463.01, 1348.85, 1236.61, 1127.88, 755.42, 696.77. 1H NMR (CDCl$_3$): δ 7.49 (d, J=5.9 Hz, 1H), 7.26-7.17 (m, 4H), 7.0-6.87 (m, 2H), 6.75 (s, 1H), 6.27 (d, J=5.9 Hz, 1H), 5.25 (d, J=5.59 Hz, 1H), 5.13 (t, J=6.79 Hz, 1H), 3.86 (s, 9H), 3.2-3.1 (m, 1H), 3.0-2.8 (m, 1H), 2.62-1.55 (s, 6H), 1.12 (d, J=7.7 Hz, 3H); $^{13}$C $^{13}$C NMR (125 MHz, CDCl$_3$):18.66, 20.92, 22.12, 32.02, 40.70, 43.35, 50.51, 56.09, 59.40, 60.73, 71.29, 79.21, 83.76, 85.95, 103.50, 114.74, 122.07, 128.18, 133.29, 153.56, 164.00, 174.614, 210.00. ESIMS: 571.8 (M). Elemental analysis calcd. for $C_3H_{35}NO_8$ C=67.75%, H=6.42%, N=2.55%. Found. C=67.70%, H=6.39%, N=2.58%.

Compound 30: To a solution of Parthenin (1 equivalent) in dry benzene, was added N-[3,5-dimethyl-4-hydroxyphenyl]-α-phenyl nitrone (1.5 equivalent). The reaction mixture was refluxed for 6 hours. The solvent was evaporated in vaccuo and the crude was subjected to column chromatography. The pure product was characterized on the basis of $^1H/^{13}C$-NMR, and mass spectrometry: Pale yellow color solid, M.p. 108° C.; $[\alpha]_D^{25}$ +65.33; I.R (KBr, 3438.94, 2923.67, 2851.63, 1594.66, 1384.49, 1352.07, 1020.03, 669.20. 1H NMR (CDCl$_3$): δ 7.45 (d, J=5.9 Hz, 1H), 7.26-7.10 (m, 4H), 6.93 (m, 3H), 6.22 (d J=5.88 Hz, 1H), 5.24 (d, J=5.63 Hz, 1H), 5.03 (t, J=2.55 Hz, 1H), 3.12-3.22 (m, 1H), 2.87-2.75 (m, 1H), 2.5-1.5 (m, 6H), 2.4 (s, 6H), 1.28 (s, 3H), 1.1 (d, J=7.57 Hz, 3H). $^{13}$C NMR (200 MHz, CDCl$_3$): 16.24, 18.60, 21.24, 21.97, 30.74, 32, 42.14, 46.99, 51.21, 60, 72.71, 78.46, 84.05, 85.45, 115.08; 117, 120.89, 122.56, 126.71, 128.71, 132, 151.33, 151.68, 161.63, 173.52, 210. ESIMS: 525.8 (M+1). Elemental analysis calcd. for $C_{30}H_{33}NO_6$ C=71.55%, H=6.61%, N=2.78%. Found. C=71.58%, H=6.63%, N=2.81%.

Compound 31: To a solution of Parthenin (1 equivalent) in dry benzene, was added N-[3-chlorophenyl]-α-phenyl nitrone (1.5 equivalent). The reaction mixture was refluxed for 7 hours. The solvent was evaporated in vaccuo and the crude was subjected to column chromatography. The pure product was characterized on the basis of $^1H/^{13}C$-NMR, and mass spectrometry: Pale yellow color solid, M.p. 180° C.; $[\alpha]_D^{25}$ +159.39; I.R (KBr, cm$^{-1}$): 3455.41, 3007.02, 2926.19, 1745.20, 1725.74, 1597.96, 1348.89, 976.86, 752.60. $^1$H NMR (CDCl$_3$): δ 7.55 (s, 1H), 7.48 (d, J=5.88 Hz, 1H), 7.35-7.16 (m, 5H), 6.96-6.84 (m, 3H); 6.26 (d, J=5.9 Hz, 1H, 5.26 (d, J=5.62 Hz, 1H), 5:16 (t, J=7.05 Hz, 1H), 3.24-3.12 (m, 1H), 3.05-2.9 (m, 1H), 2.55-1.5 (m, 6H), 1.37 (s, 3H), 1.125 (d, J=7.57 Hz, 3H); $^{13}$C NMR (125 MHz, CDCl$_3$): δ 18.06, 20.11, 21.78, 31.55, 40.27, 42.85, 49.36, 59.00, 69.96, 79.49, 85.50, 87.00, 114.75, 122.48, 124.86, 126.63, 128.13, 128.93, 135.00, 163.42, 211.00; ESIMS: 494.1 (M+1); Elemental analysis calcd. for $C_{28}H_{28}ClNO_5$ C=68.08%, H=5.71%, N=2.84%. Found. C=68.11%, H=5.73%, N=2.81%.

Compound 32: To a solution of Parthenin (1 equivalent) in dry benzene, was added N-[2-nitrophenyl]-α-phenyl nitrone (1.5 equivalent). The reaction mixture was refluxed for 8 hours. The solvent was evaporated in vaccuo and the crude was subjected to column chromatography. The pure product was characterized on the basis of $^1H/^{13}C$-NMR, and mass spectrometry: Reddish yellow color solid, M.p. 158° C.; $[\alpha]_D^{25}$ +25.60; I.R (KBr, cm$^{-1}$): 3432.85, 2926.43, 2871.52, 1776.85, 1721.31, 1597.29, 1524.75, 1348.79, 976.09, 756.99, 696.25; $^1$H NMR (CDCl$_3$): δ 8.02-7.92 (m, 2H), 7.6-7.53 (t, J=7.24 Hz, 1H), 7.40 (d, J=5.81 Hz, 1H), 7.17-

7.03 (m, 3H), 6.86-6.69 (m, 3H), 6.19 (d, J=5.84 Hz, 1H), 5.74 (t, J=7.52 Hz, 1H), 5.19 (d, J=5.57 Hz, 1H), 3.3-3.2 (m, 1H), 3.05-2.9 (m, 1H), 2.37-1.5 (m, 6H), 1.28 (s, 3H), 1.01 (d, J=7.71 Hz, 3H); $^{13}$C NMR (125 MHz, CDCl$_3$): δ 18.03, 20.06, 21.95, 31.51, 40.25, 49.29, 59.00, 66.91, 79.26, 85.00, 87.00, 89.5, 113.46, 117.00, 123.00, 125.01, 128.71, 129.07, 132.36, 134.21, 138.00, 148.00, 151.00, 163.35, 212.11. ESIMS: 527.1 (M+23); Elemental analysis calcd. for C$_{29}$H$_{29}$NO$_7$ C=69.18%, H=5.80%, N=2.78%. Found: C=69.21%, H=5.77%, N=2.82%.

Compound 33: To a solution of Parthenin (1 equivalent) in dry benzene, was added N-[2-methoxyphenyl]-α-phenyl nitrone (1.5 equivalent). The reaction mixture was refluxed for 8.5 hours. The solvent was evaporated in vaccuo and the crude was subjected to column chromatography. The pure product was characterized on the basis of $^{1}$H/$^{13}$C-NM and mass spectrometry: Brown color solid M.p. 111° C.; [α]$_D^{25}$ +73.61. I.R (KBr, cm$^{-1}$): 3410.10, 2923.80, 2871.27, 1753.32, 1726.45, 1596.79, 1487.14, 1201.64, 974.48, 753.76, 717.70. $^{1}$H NMR (CDCl$_3$): δ 7.56-7.45 (m, 3H), 7.31-7.19 (m, 2H), 7.0-6.92 (m, 5H), 6.30 (d, J=5.85 Hz, 1H), 5.3 (d, J=5.72 Hz, 1H), 5.2 (t, 1H), 3.87 (s, 3H), 3.3-3.2 (m, 1H), 3.05-2.9 (m, 1H), 2.62-1.6 (m, 6H), 1.4 (s, 3H), 1.2 (d, J=2.84 Hz, 3H); $^{13}$C NMR (125 MHz, CDCl$_3$): δ 18.07, 20.13, 21.69, 31.58, 34.83, 40.22, 43.00, 49.57, 55.40, 59.5, 70.40, 79.51, 114.41, 115.40, 117.80, 122.49; 427:92; 129.14, 133.00, 132.12; 152.00, 160.00, 163.615; 172.00, 211.00, 85.5, 87.00. ESIMS: 512.1 (M+23); Elemental analysis calcd. for C$_{29}$H$_{31}$NO$_6$ C=71.15%, H=6.38%, N=2.86%. Found. C=71.18%, H=6.42%, N=2.79%.

Synthesis of Spiroaziridine Derivatives of Parthenin:

Compound 34: To a solution of Parthenin (1 equivalent) in dry Toluene (10 ml), was added Azido-benzene (2 equivalent) maintaining the temperature between 100-105° C. and the reaction mixture was stirred at this temperature for 15 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^{1}$H NMR, $^{13}$CNMR, DEPT and mass spectrometry: colourless solid.M.p. 245-247° C., [α]$_D^{25}$. -16, IR (KBr, cm$^{-1}$): 3439, 2961, 2925, 1779, 1751, 1721, 1590 and 1562. $^{1}$H NMR (CDCl$_3$, 200 MHz):d 1.14 (d, 3H, J=7.6 Hz), 1.38 (s, 3H), 1.57-2.05 (m, 4H), 2.07-2.40 (m, 2H), 4.85 (d, 1H, J=7.55 Hz), 6.15 (d, 1H, J=5.3 Hz), 6.61 (d, 2H, J=7.8 Hz), 6.95-7.10 (m, 1H), 7.14 (d, 2H, J=7.8 Hz), 7.48 (d, 1H, J=5.3) $^{13}$C NMR (CDCl$_3$, 200 MHz):d 17.0, 20.5, 22.4, 25.6, 29.3, 45.2, 60.2, 77.8, 80.0, 84.6, 90.4, 116.1, 119.1, 124.0, 130.5, 138.6, 159.9, 171.5, 176.2, 210.5; ESI-MS: 376 (M+23). Elemental analysis calcd. for C$_{21}$H$_{23}$NO$_4$ C=71.37%, H=6.56%, N=3.96%. Found. C=70.3%, H=7.1% and N=3.9%

Compound 35: To a solution of Parthenin (1 equivalent) in dry Toluene (10 ml), was added 1-Azido-3-chloro-benzene (2 equivalent) maintaining the temperature between 100-105° C. and the reaction mixture was stirred at this temperature for 16 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^{1}$H NMR, $^{13}$CNMR, DEPT and mass spectrometry: [α]$_D^{25}$: -8, IR (KBr, cm$^{-1}$) 3443, 2961, 2918, 1789, 1751, 1726, 1590 and 1568. $^{1}$HNMR (CDCl$_3$, 200 MHz): d 1.13 (d, 3H, J=7.5 Hz), 1.36 (s, 3H), 1.55-2.10 (m, 4H), 2.07-2.36 (m, 2H), 4.79 (d, 1H, J=7.71 Hz), 6.16 (d, 1H, J=5.7 Hz), 6.52 (d, 1H, J=7.0 Hz), 6.71 (m, 2H), 7.10 (d, 1H, J=7.0 Hz), 7.48 (d, 1H, J=5.7) $^{13}$C NMR (CDCl$_3$, 200 MHz):d 19.0, 21.5, 22.4, 26.6, 29.3, 46.2, 57.2, 75.8, 80.0, 83.6, 90.4, 119.1, 122.1, 124.0, 130.5, 140.6, 159.9, 178.5, 185.2, 208.5; ESI-MS: 410 (M+23). Elemental analysis calcd. for C$_{21}$H$_{22}$ClNO$_4$ C=65.03%, H=5.72%, N=3.61%. Found. C=67.03%, H=5.01% and Compound 36: To a solution of Parthenin (1 equivalent) in dry Toluene (10 ml), was added 1-Azido-4-methoxy-benzene (2 equivalent) maintaining the temperature between 100-105° C. and the reaction mixture was stirred at this temperature for 12 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^{1}$H NMR, $^{13}$CNMR, DEPT and mass spectrometry: M.p. 245-247° C., [α]$_D^{25}$. -16, IR (KBr, cm$^{-1}$): 3443, 2961, 2918, 1789, 1751, 1726, 1590 and 1568. $^{1}$H NMR (CDCl$_3$, 200 MHz): d 1.17 (d, 3H, J=7.7 Hz), 1.38 (s, 3H), 1.50-2.11 (m, 4H), 2.10-2.37 (m, 2H), 3.77 (s, 3H), 5.29 (d, 1H, J=7.1 Hz), 6.25 (d, 1H, J=5.9 Hz), 6.79 (s, 4H), 7.41 (d, 1H, J=5.9) $^{13}$C NMR (CDCl$_3$, 200 MHz): d 17.3, 19.8, 23.6, 29.7, 35.1, 41.0, 59.1, 77.3, 79.3, 84.5, 114.5, 120.5, 122.1, 132.0, 155.8, 163.6, 210.5 ESI-MS: 406 (M+23). Elemental analysis calcd. for C$_{22}$H$_{25}$NO$_5$. C=68.91%, H=6.57%, N=3.65%. Found: C=67.03%, H=7.01% and N=3.34%.

Compound 37: To a solution of Parthenin (1 equivalent) in dry Toluene (10 ml), was added 1-Azido-2-methoxy-benzene (2 equivalent) maintaining the temperature between 100-105° C. and the reaction mixture was stirred at this temperature for 12 hours. The solvent was evaporated in vaccuo and the crude product was subjected for, column chromatography (silica gel, 100-200 mesh, elution; n-hexane/EtOAc gradient) to afford pure product. The pure product was characterized on the basis of I.R, $^{1}$H NMR, $^{13}$CNMR, DEPT and mass spectrometry. Brownish syrupy liquid. [α]$_D^{25}$. -4, IR (KBr, cm$^{-1}$): 3436, 2923, 2853, 1746, 1725, 1711, 1590 and 1558. $^{1}$H NMR CDCl$_3$, 200 MHz): d 1.15 (d, 3H, J=7.6 Hz), 1.34 (s, 3H), 1.49-2.12 (m, 4H), 2.09-2.39 (m, 2H), 3.84 (s, 3H), 5.33 (d, 1H, J=7.33 Hz), 6.23 (d, 1H, J=5.8 Hz), 6.9-7.1 (m, 4H), 7.49 (d, 1H, J=5.8) $^{13}$C NMR (CDCl$_3$, 200 MHz): d 16.8, 20.8, 25.6, 28.7, 36.1, 44.0, 57.1, 76.3, 76.3, 85.5, 119.5, 122.5, 152.1, 132.0, 156.8, 167.6, 21.0.6; ESIMS: 406 (M+23). Elemental analysis calcd. for C$_{22}$H$_{25}$NO$_5$ C=68.91%, H=6.57%, N=3.65%. Found: C=69.03%; H=6.01% and N=3.84%.

Compound 38: To a solution of Parthenin (1 equivalent) in dry Toluene (10 ml), was added 1-Azido-3-methyl-benzene (2 equivalent) maintaining the temperature between 100-105° C. and the reaction mixture was stirred at this temperature for 10 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^{1}$HNMR, $^{13}$CNMR, DEPT and mass spectrometry: Syrupy brown liquid. [α]$_D^{25}$. -16, IR (KB; cm$^{-1}$): 3439, 2961, 2925, 1779, 1751, 1721, 1590 and 1562. $^{1}$H NMR (CDCl$_3$, 200 MHz): d 1.12 (d, 3H, J=7.6 Hz), 1.37 (s, 3H), 1.53-2.08 (m, 4H), 2:07-2.39 (m, 2H), 2.21 (s, 3H), 5.29 (d, 1H, J=7.2 Hz), 6.26 (d, 1H, J=5.6 Hz), 6.75 (d, 2H, J=8.2 Hz), 7.06 (d, 2H, J=8.2), 7.48 (d, 1H, J=5.6). $^{13}$C NMR (CDCl$_3$, 200 MHz): d 18.3, 20.8, 24.6, 30.7, 35, 1, 3.0, 55.1, 79.3, 81.3, 84.5, 113.5, 120.5, 124.1, 132.0, 157.8, 168.6, 183.1; ESIMS: 390 (M+23). Elemental analysis calcd. for C$_{22}$H$_{25}$NO$_4$ C=71.91%, H=6.87%, N=3.81%. Found: C=69.93%, H=7.01% and N=4.34%

Compound 39: To a solution of Parthenin (1 equivalent) in dry Toluene (10 ml), was added 1-Azido-2-nitro-benzene (2 equivalent) maintaining the temperature between 100-105° C. and the reaction mixture was stirred at this temperature for 8 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^1$H NMR, $^{13}$CNMR, DEPT and mass spectrometry: Colorless solid.M.p. 222-224° C. $[\alpha]_D^{25}$. −6, IR (KBr, cm$^{-1}$): 3439, 2961, 2925, 1779, 1751, 1721, 1590 and 1562. $^1$H NMR (CDCl$_3$, 200 MHz): d 1.10 (d, 3H, J=7.5 Hz), 1.39 (s, 3H), 1.53-2.08 (m, 4H); 2.07-2.39 (m, 2H), 4.73 (d, 1H, J=7.2 Hz), 6.04 (d, 1H, J=5.7 Hz), 7.30 (d, 2H, J=6.3 Hz), 7.49 (d, 1H, J=5.7), 7.48 (d, 1H, J=5.7), 7.83 (m, 1H). $^{13}$C NMR (CDCl$_3$, 200 MHz) δ 17.3, 20.8, 23.6, 30.7, 36.1, 43.0, 54.1, 79.3, 81.3, 84.5, 113.5, 120.5, 126.2, 132.0, 157.8, 178.6, 183.1, 210.3; ESI-MS: 421 (M+23). Elemental analysis calcd. for C$_{21}$H$_{23}$N$_2$O$_6$ C=63.31%, H=5.57%, N=7.03%. Found: C=64.93%, H=6.01, N=6.34%.

Compound 40: To a solution of Parthenin (1 equivalent) in dry benzene (1.0 ml), was added 1-Azido-3-nitro-benzene (2 equivalent) maintaining the temperature between 75-80° C. and the reaction mixture was stirred at this temperature for 15 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^1$H NMR, $^{13}$CNMR, DEPT and mass spectrometry: yellow solid.M.p: 241-242° C. $[\alpha]_D^{25}$. −14, IR (KBr, cm$^{-1}$): 3439, 2961, 2925, 1779, 1751, 1721, 1590 and 1562. $^1$H NMR (CDCl$_3$, 200 MHz): d 1.13 (d, 3H, J=7.6 Hz), 1.38 (s, 3H), 1.57-2.05 (m, 4H), 2.08-2.37 (m, 2H), 4.86 (d, 1H, J=6.7 Hz), 6.21 (d, 41, J=5.9 Hz), 7.38 (d, 2H, J=7.8 Hz), 7.62 (m, 2H), 7.89 (d, 1H, J=5.9). $^{13}$C NMR (CDCl$_3$, 200 MHz) δ 18.0, 20.5, 21.4, 25.6, 29.3, 48.2, 60.2, 78.8, 80.0, 84.6, 90.4, 100.7, 116.1, 119.1, 124.0, 130.5, 138.6, 159.9, 171.5, 178.2, 210.8; EST-MS: 421 (M+23). Elemental analysis calcd. for C$_{21}$H$_{22}$N$_2$O$_6$ C=63.31%, H=5.57%, N=7.03%. Found: C=64.3%, H=4.98.1% and N=7.39

Compound 41: To a solution of Parthenin (1 equivalent) in dry Toluene (10 ml), was added 3-Azido-benzoic acid methyl ester (2 equivalent) maintaining the temperature between 100-105° C. and the reaction mixture was stirred at this temperature for 15 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^1$H NMR, $^{13}$CNMR, DEPT and mass spectrometry: colorless solid, M.p. 251-253° C. $[\alpha]_D^{25}$ −10. IR (KBr, cm$^{-1}$): 3453, 2951, 2924, 1779, 1751, 1746, 1590 and 1578. $^1$H NMR (CDCl$_3$, 200 MHz): d 1.18 (d, 3H, J=7.5 Hz), 1.39 (s, 3H), 1.45-2.10 (m, 4H), 2.12-2.36 (m, 2H), 4.80 (d, 1H, J=7.5 Hz), 6.14 (d, 1H, J=5.5 Hz), 6.82 (d, 1H, J=7.9 Hz), 7.20-743 (m, 3H), 7.49 (s, 1H, J=5.5 Hz) $^{13}$C NMR (CDCl$_3$, 200 MHz) δ 19.0, 22.5, 22.4, 28.6, 29.3, 36.7, 46.2, 57.2, 75.8, 85.0, 89.6, 90.4, 119.1, 122.1, 124.0, 130.5, 140.6, 159.9, 171.5, 178.2, 210.8. ESI-MS: 434 (M+23). Elemental analysis calcd. for C$_{23}$H$_{25}$NO$_5$ C=67.14%, H=6.12%, N=3.40%. Found: C=66.03%, H=7.67% and N=4.19%

Compound 42: To a solution of Parthenin (1 equivalent) in dry benzene (10 ml), was added 1-Azido-4-methyl-benzene (2 equivalent) maintaining the temperature between 70-80° C. and the reaction mixture was stirred at this temperature for 16 hours. The solvent was evaporated in vaccuo and the crude product was subjected for column chromatography (silica, gel, 100-200 mesh, elution; n-hexane/EtOAc gradient) to afford pure product. The pure product was characterized on the basis of I.R, $^1$H NMR, $^{13}$CNMR, DEPT and mass spectrometry.

Whitish solid.M.p: 241-242° C. $[\alpha]_D^{25}$. −12. IR (KBr, cm$^{-1}$): 3493, 2979, 2926, 1869, 1371, 1756, 1589, 1573 and 1235. $^1$H NMR (CDCl$_3$, 200 MHz): d 1.13 (d, 3H, J=7.6 Hz), 1.36 (s, 3H), 1.53-2.08 (m, 4H), 2.07-2.39 (m, 2H), 2.19 (s, 3H), 5.32 (d, 1H, J=7.3 Hz), 6.28 (d, 1H, J=5.5 Hz), 6.78 (d, 1H, J=8.35 Hz); 7.06 (d, 2H, J=8.35 Hz), 7.49 (d, 1H, J=5.5). $^{13}$C NMR (CDCl$_3$, 200 MHz) δ 18:5, 20.8, 26.6, 33.7, 35.1, 43.0, 55.1, 76.3; 89.3, 85.5, 113.5., 125.5, 129.1, 132.0, 158.8, 167.6, 185.1, 211.0, ESI-MS: 390 (M+23). Elemental analysis calcd. for C$_{22}$H$_{25}$NO$_4$ C=71.91%, H=6.87%, N=3.81%. Found: C=70.93%, H=7.21% and N=4.34%.

Compound 43: To a solution of Parthenin (1 equivalent) in dry Toluene (10 ml), was added 1-Azido-2-methyl-benzene (2 equivalent) maintaining the temperature between 100-105° C. and the reaction mixture was stirred at this temperature for 22 hours. The solvent was evaporated in vaccuo and the crude product was subjected for column chromatography (silica gel, 100-200 mesh, elution; n-hexane/EtOAc gradient) to afford pure product. The pure product was characterized on the basis of I.R, $^1$H NMR, $^{13}$CNMR, DEPT and mass spectrometry: Greyish syrupy liquid. $[\alpha]_D^{25}$. −6. IR (KBr, cm$^{-1}$): 3432, 2989, 2916, 1869, 1311, 1756, 1539, 1573 and 1245. $^1$H NMR (CDCl$_3$, 200 MHz): d 1.12 (d, 3H, J=7.6 Hz), 1.37 (s, 3H), 1.52-2.10 (m, 4H), 2.10-2.39 (m, 2H), 234 (s, 3H), 4.79 (d, 1H, J=7.7 Hz), 6. 15 (d, 1H, J=5.7 Hz), 6.54 (d, 1H, J=7.0 Hz), 6.72 (m, 3H), 7.09 (d, 1H, J=8.5), 7.48 (d, 1H, J=5.7). $^{13}$C NMR (CDCl$_3$, 200 MHz) δ 17.5, 23.8, 26.6, 31.7, 35.1, 45.0, 55.1, 76.3, 89.3, 89.5, 95.6, 123.5, 128.5, 134.1, 139.0, 158.8, 167.6, 185.1, 211.0, ESI-MS: 390 (M+23). Elemental analysis calcd. for C$_{22}$H$_{25}$NO$_4$ C=71.91%, H=6.87%, N=3.81%, Found. C=71.63%, H=7.25% and N=4.44%.

REFERENCES

1. Herz, W.; Watanabe, H.; Miyazaki, M.; Kishida. Y, *J. Am. Chem. Loc.* 1962, 84, 2601.
2. Schmidt, T: J., Toxic Activities of Sesquiterpene Lactones—structural and Biochemical Aspects, *Current Org. Chem.* 1999, 3, 577-608.
3. Dirsch, V. M.; Stuppner, Vollmar, A. M. Helenalin triggers a CD95 death receptor-independent apoptosis that is not affected by overexpression of Bcl-x$_L$ or Bcl-2[1], *Cancer Res.* 2001, 61, 5817-5823.
4. Monks, D. Seudiero, Skehan, R. Shoemaker, K. Paull, D. Vistica, C. Hose, J. Langley, P. Cronise, A. Vaigro-WolV, M. Gray-Goodrich, H. Campbell; J. Mayo, M, Boyd, Feasibility of a high-flux anticancer drug screen using a diverse panel of cultured human tumor cell lines, *J. Natl. Cancer Inst.* 1991, 83, 757-766.
5. Skehan, P.; Storeng, R.; ScUdiero, D.; Monks, A.; Mcmahon, J.; Vitica, D.; Warren, J. T.; Bokesch, H.; Kenney, S.; Boyd M. R. New colorimetric cytotoxic assay for anticancer drug screening. *Journal of National Cancer Institute,* 1990, 82, 1107-1112
6. Krishan, A. Rapid flow cytofluorometric analysis of mammalian cell cycle by propidium iodide staining. *Journal of Cell biology,* 1975, 66, 188-193,
7. Garcia-Pineres, A. J.; Castro, V.; Mora, G.; Schmidt, T. J.; Strunck, B.; Pahl, H. L.; Merfort, I. *J. Biol. Chem.* 2001, 276, 39713-39720.
8. Mazor, R. L.; Menendez, I. Y.; Ryan, M. A.; Fiedler, M. A.; Wong, H. R. *Cytokine* 2000, 12, 239-245.

9. Hehner, S. P.; Hofmann, T. G.; Ratter, F.; Dumont, A.; Droge, W.; Schmitz, M. L. *J Biol. Chem.* 1998, 273, 18117-18121.
10. Guido L.; Knorre, A.; Schmidt; T. J.; Pahl, H. L.; Merfort, I. *J. Biol. Chem.* 1998, 273, 33508-33516.
11. Garcia-Pineres, A. J.; Lindenmeyer, M. T.; Merfort, *J. Life Set.* 2004, 75, 841-856.
12. Lee, K. H.; Furukawa, H. *Journal of Medicinal Chemistry,* 1972, 15, 609.
13. Dhillon, R. S.; Nayyar, K.; Singh, S.; Dhaliwal, Z. S. *Indian J. Chem.,* 1994, 33B, 1038.
14. Das, B.; Kashinatham, A.; Madhusudhan, P. *Tetrahedron Lett.,* 1997, 38, 7457.
15. Das, B.; Madhusudhan, P., Kashinatham A. *Tetrahedron Lett,* 1998, 39, 431.
16. Ruesch, H.; Mabry, T. J. *Tetrahedron,* 1969, 25, 805
17. Wagner, S.; Hofmann, A.; Siedle, B.; Terfloth, L.; Merfort, L; Gasteiger, J.; *J. Med, Chem.* 2006, 49, 2241, 2252.
18. Santoro. et al. U.S. Pat. No. 6,391,200, 2004.
19. Huisgen, R. *Angew. Chem. Int. Ed. Engl.* 1963, 2, 565.
20. Padwa, A. *Angew. Chem.* 1976, 88, 131.
21. Hamer, J.; Macaluso, A. Chem. Rev. 1964, 64, 471
22. Kumar, H. M. S.; Anjaneyulu, S.; Yadav, J. S, *Synthetic comm.* 1999, 29, 877.
23. Kumar, H. M. S.; Anjaneyulu, S.; Reddy, B. V. S.; Yadav, J. S. *Synlett,* 1999, 5, 551.

TABLE 1

| Entry | Reactant | Product[a] | Reaction time (h) (yield, %) |
|---|---|---|---|
| 1 | MeO–C6H4–CNO | [structure with OMe aryl] | 2 (68) |
| 2 | Cl–C6H4–CNO | [structure with Cl aryl] | 2.5 (71) |
| 3 | 2-Br–C6H4–CNO | [structure with 2-Br aryl] | 2 (75) |
| 4 | (H3C)2N–C6H4–CNO | [structure with N(CH3)2 aryl] | 3 (67) |

TABLE 1-continued
| Entry | Reactant | Product[a] | Reaction time (h) (yield, %) |
|---|---|---|---|
| 5 |  | 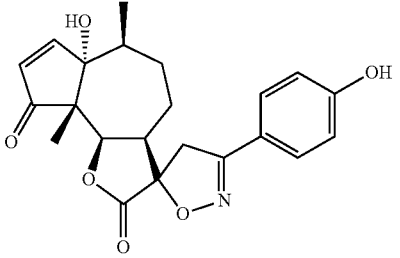 | 2.5 (73) |
| 6 | 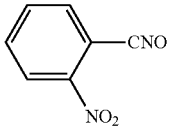 | 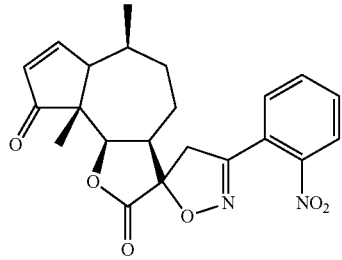 | 3 (77) |
| 7 | 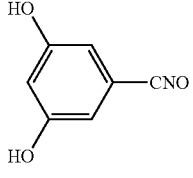 | 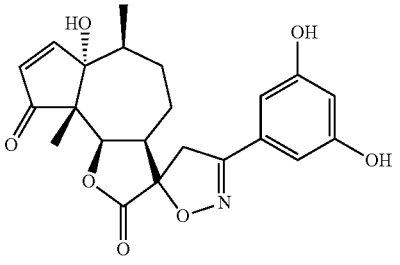 | 1.5 (69) |
| 8 | 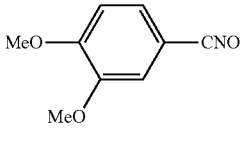 | 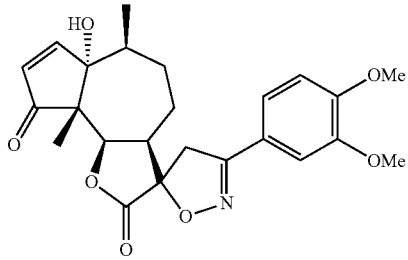 | 2.5 (78) |
| 9 | 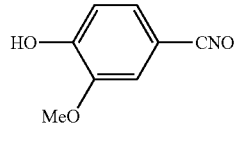 | 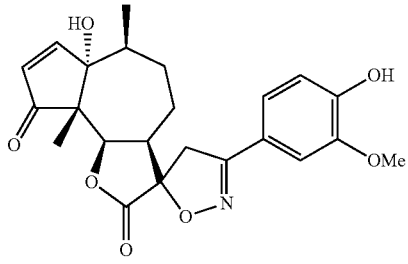 | 3 (74) |

TABLE 1-continued
| Entry | Reactant | Product[a] | Reaction time (h) (yield, %) |
|---|---|---|---|
| 10 | 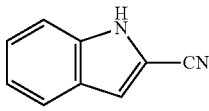 | 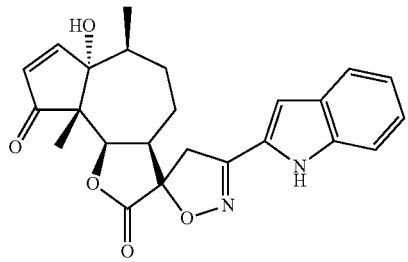 | 1.5 (75) |
| 11 | 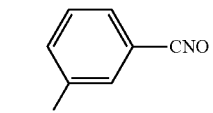 | 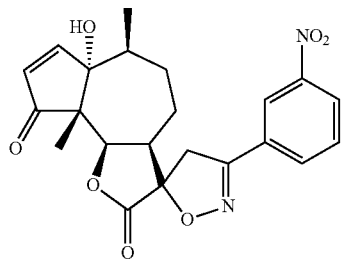 | 2 (70) |
| 12 | 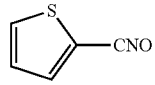 | 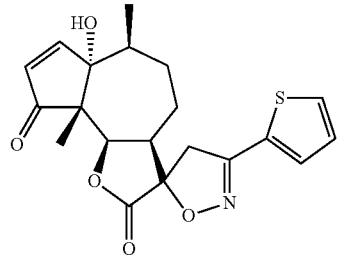 | 2 (74) |
| 13 | 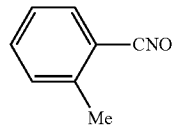 | 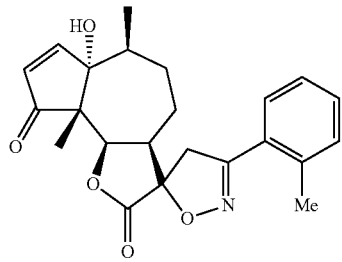 | 2 (71) |
| 14 | 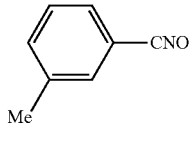 | 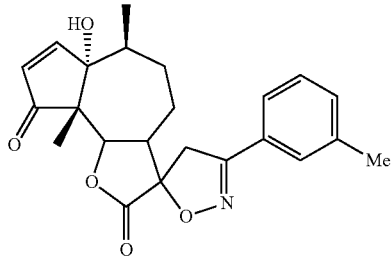 [SMILES: Cc1cccc(C2=NOC3(C2)C(=O)OC2C3CC[C@H](C)[C@]3(O)C=CC(=O)[C@@]23C)c1] | 2 (72) |

TABLE 1-continued
| Entry | Reactant | Product[a] | Reaction time (h) (yield, %) |
|---|---|---|---|
| 15 | 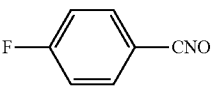 | 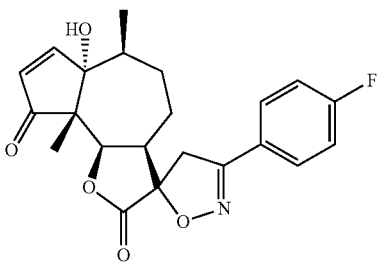 | 2.5 (78) |
| 16 | 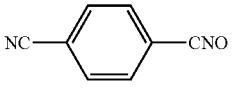 | 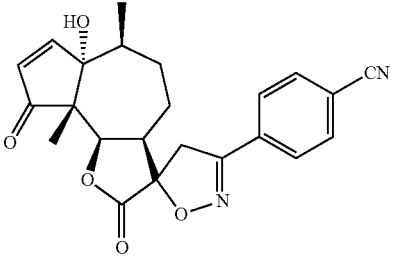 | 2.5 (70) |
| 17 | 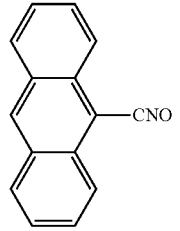 | 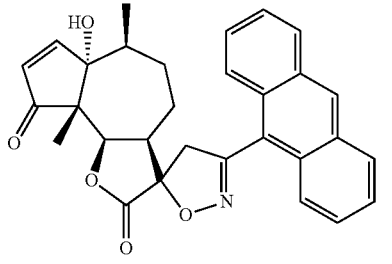 | 2 (76) |
[a]All compounds were characterized by $^1$H NMR, mass spectroscopy.
[b]Yields obtained after column chromatography.
TABLE 2
| Entry | Reactant | Product | Reaction time (h) (yield, %) |
|---|---|---|---|
| 18 | 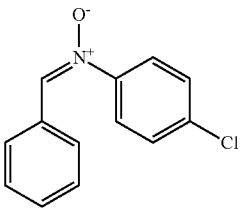 [SMILES: [O-]/[N+](=C/c1ccccc1)c1ccc(Cl)cc1] | 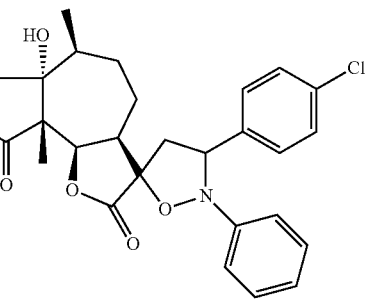 | 8 (82) |

TABLE 2-continued
| Entry | Reactant | Product | Reaction time (h) (yield, %) |
|---|---|---|---|
| 19 | 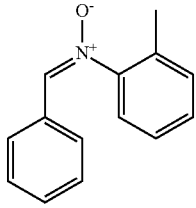 [SMILES: Cc1ccccc1/[N+]([O-])=C\c1ccccc1] | 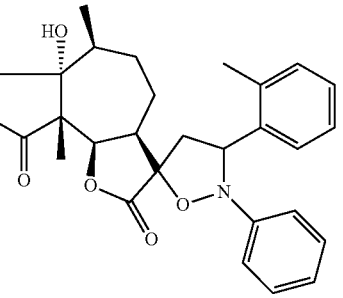 | 6 (75) |
| 20 | 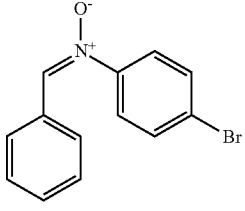 [SMILES: [O-]/[N+](=C/c1ccccc1)c1ccc(Br)cc1] | 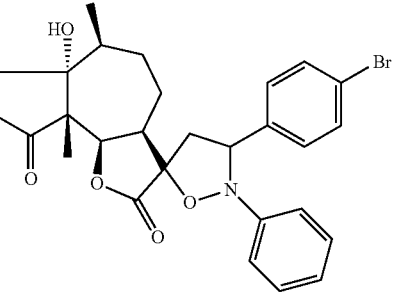 | 8 (72) |
| 21 | 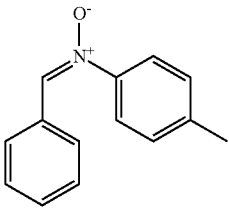 [SMILES: Cc1ccc(/[N+]([O-])=C\c2ccccc2)cc1] | 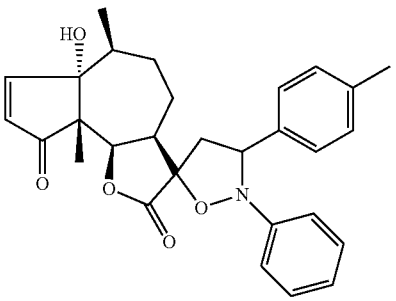 | 6 (80) |
| 22 | 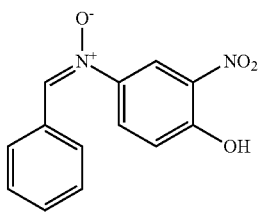 [SMILES: O=[N+]([O-])c1cc(/[N+]([O-])=C\c2ccccc2)ccc1O] | 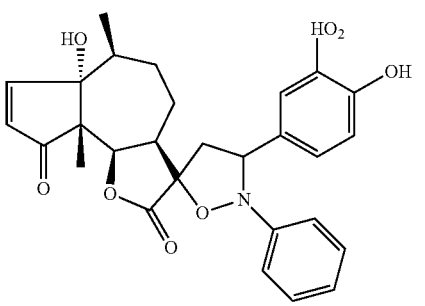 | 7 (76) |
| 23 | 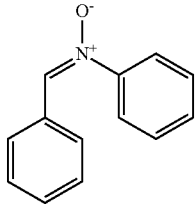 [SMILES: [O-]/[N+](=C/c1ccccc1)c1ccccc1] | 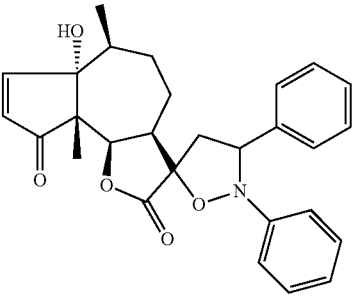 | 8 (75) |

TABLE 2-continued

| Entry | Reactant | Product | Reaction time (h) (yield, %) |
|---|---|---|---|
| 24 | | | 6 (71) |
| 25 | | | 6 (74) |
| 26 | | | 7 (85) |
| 27 | | | 8 (78) |
| 28 | | | 9 (75) |

TABLE 2-continued

| Entry | Reactant | Product | Reaction time (h) (yield, %) |
|---|---|---|---|
| 29 | | | 8 (71) |
| 30 | | | 6 (72) |
| 31 | | | 7 (74) |
| 32 | | | 8 (71) |

TABLE 2-continued
| Entry | Reactant | Product | Reaction time (h) (yield, %) |
|---|---|---|---|
| 33 | 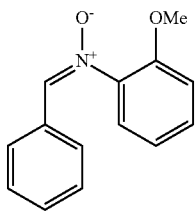 [SMILES: COc1ccccc1/[N+]([O-])=C\c1ccccc1] | 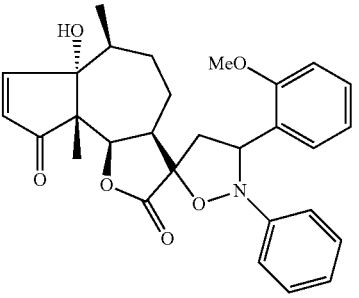 | 8.5 (74) |
a) All compounds were characterized by $^1$H NMR, mass spectroscopy.
b) Yields obtained after column chromatography.
TABLE 3
| Entry | Reactant | Product[a] | Reaction time (h), Yield |
|---|---|---|---|
| 34 | 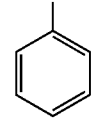 | 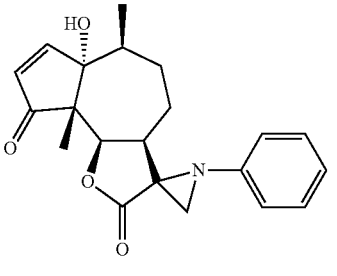 | 15 (62) |
| 35 | 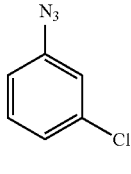 | 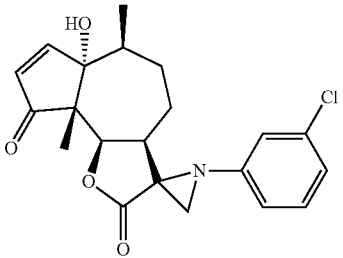 | 16 (62) |
| 36 | 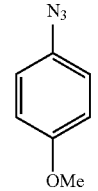 [SMILES: COc1ccc(N=[N+]=[N-])cc1] | 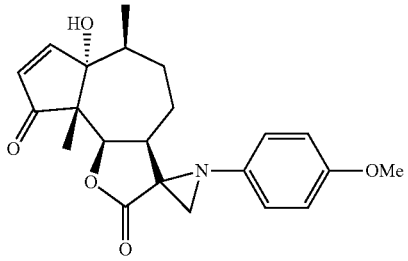 | 12 (62) |

TABLE 3-continued

| Entry | Reactant | Product | Reaction time (h), Yield |
|---|---|---|---|
| 37 | 2-azido anisole | spiro aziridine product with 2-methoxyphenyl | 12 (45) |
| 38 | 3-azido toluene | spiro aziridine product with 3-methylphenyl | 10 (53) |
| 39 | 2-azido nitrobenzene | spiro aziridine product with 2-nitrophenyl | 8 (43) |
| 40 | 3-azido nitrobenzene | spiro aziridine product with 3-nitrophenyl | 15 (53) |
| 41 | methyl 3-azidobenzoate | spiro aziridine product with 3-(methoxycarbonyl)phenyl | 15 (47) |

TABLE 3-continued

| Entry | Reactant | Product[a] | Reaction time (h), Yield |
|---|---|---|---|
| 42 | 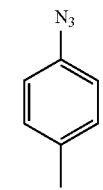 | 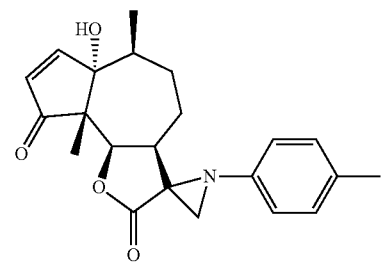 | 16 (49) |
| 43 | 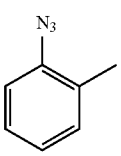 | 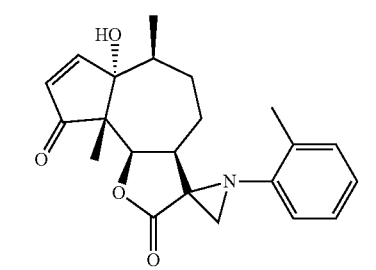 | 22 (48) |

[a] All compounds were characterized by 1H NMR, mass spectroscopy.
[b] Yields obtained after column chromatography.

TABLE 4

$IC_{50}$ (µM) values of various derivatives of parthenin.

| Compound | SW-620 | DU-145 | PC-3 |
|---|---|---|---|
| Compound -1 | 41 | 20 | 35 |
| Compound -2 | 51 | 43 | 49 |
| Compound -3 | — | — | — |
| Compound -4 | — | — | 6.33 |
| Compound -5 | 89 | 93 | — |
| Compound -6 | 40 | 34 | 37 |
| Compound -7 | 69 | 72 | 84 |
| Compound -80 | 86 | 84 | — |
| Compound -9 | — | — | — |
| Compound -10 | — | — | — |
| Compound -11 | 49 | 51 | 55 |
| Compound -12 | 34 | 19 | 29 |
| Compound -13 | 5 | 12 | 10 |
| Compound -14 | — | — | 66.6 |
| Compound -15 | 3.6 | 13 | 27 |
| Compound -16 | 53 | 26 | 32 |
| Compound -17 | 4.3 | 4.6 | 4.9 |
| Compound -18 | 7.5 | 7 | 7.8 |
| Compound -19 | 6 | 5.6 | 6.4 |
| Compound -20 | 6.7 | 6.3 | 5.8 |
| Compound -21 | 8.7 | 8.1 | 8.5 |
| Compound -22 | 9.4 | 9.8 | 8.1 |
| Compound -23 | 5.8 | 5.6 | 5.7 |
| Compound -24 | 7.3 | 6.4 | 5.7 |
| Compound -25 | 6.8 | 6.3 | 5.7 |
| Compound -26 | 4.8 | 5 | 4.8 |
| Compound -27 | 6.1 | 7.8 | 8.2 |
| Compound -28 | 7.5 | 11 | 11 |
| Compound -29 | 5.7 | 5.6 | 8.6 |
| Compound -30 | — | — | — |
| Compound -31 | 6.1 | 7.4 | 8.2 |
| Compound -32 | 13 | 28 | 8.4 |
| Compound -33 | 53 | 91 | 81 |
| Compound -34 | 87.7 | 31.4 | 10.6 |
| Compound -35 | 48.4 | 39.5 | 86.1 |
| Compound -36 | — | — | — |
| Compound -37 | 47.3 | — | 52.0 |
| Compound -38 | 15.0 | 62.5 | 61.5 |
| Compound -39 | 33.0 | 28.0 | 10.0 |
| Compound -40 | 61.0 | — | 10.1 |
| Compound -41 | 30 | 18.5 | 10.1 |
| Compound -42 | — | — | — |
| Compound -43 | 22 | — | 12.5 |
| Parthenin | 38.7 | 31.1 | 40.3 |

TABLE 5

Effect of Parthenin and its derivative Compound-17 on Ehrlich ascitic tumor (EAT) bearing mice.

| Test group | Dose (mg/kg) i.p. | Tumor Weight (mg) Mean ± SE | % Tumor growth inhibition |
|---|---|---|---|
| Control | 0.2 ml | 1708.57 ± 51.07 | — |
| Parthenin | 10 | 1542.86 ± 35.24 | 9.69 |
| Parthenin | 25 | All animals died by 4th day | |
| Parthenin | 50 | All animals died by 2nd day | |
| Compound-17 | 10 | 1547.14 ± 36.63 | 9.44 |
| Compound-17 | 25 | 1445.71 ± 41.52 | 15.38 |
| Compound-17 | 50 | 1332.14 ± 32.59* | 22.03 |
| Compound-17 | 100 | 1108.57 ± 38.02** | 35.11 |
| Compound-17 | 200 | All animals died by 3rd day | |
| 5-FU | 22 | 832.28 ± 35.21** | 51.28 |

Data presented as Mean ± SE and % tumor growth inhibition.
(n = 7)
p > 0.05 = Insignificant
*= p < 0.05 = Significant
**= p < 0.01 = Highly significant.

TABLE 6

Effect of Parthenin and its derivative Compound-17 on Ehrlich ascitic carcinoma (EAC) bearing mice.

| Test group | Dose (mg/kg) i.p. | Ascitic fluid volume (ml) Mean ± SE | Tumor cells in ascitic fluid (×10$^7$) Mean ± SE | % Tumor growth inhibition |
|---|---|---|---|---|
| Control | 0.2 ml | 4.57 ± 0.39 | 85.00 ± 4.75 | — |
| Parthenin | 10 | 3.92 ± 0.38 | 74.71 ± 2.77 | 12.01 |
| Parthenin | 25 | All animals died by 4th day | | |
| Parthenin | 50 | All animals died by 2$^{nd}$ day | | |
| Compound-17 | 10 | 4.07 ± 0.35 | 78.42 ± 2.90 | 7.74 |
| Compound-17 | 25 | 3.62 ± 0.32 | 68.71 ± 3.16 | 19.16 |
| Compound-17 | 50 | 2.85 ± 0.37* | 61.85 ± 4.20* | 27.23 |
| Compound-17 | 100 | 2.07 ± 0.33** | 33.57 ± 2.60** | 60.50 |
| Compound-17 | 200 | All animals died by 3$^{rd}$ day | | |
| 5-FU | 20 | 0 | 0 | 100 |

Data presented as Mean ± SE and % tumor growth inhibition.
(n = 7)
p > 0.05 = Insignificant
* = p < 0.05 = Significant
** = p < 0.01 = Highly significant.

Scheme 1

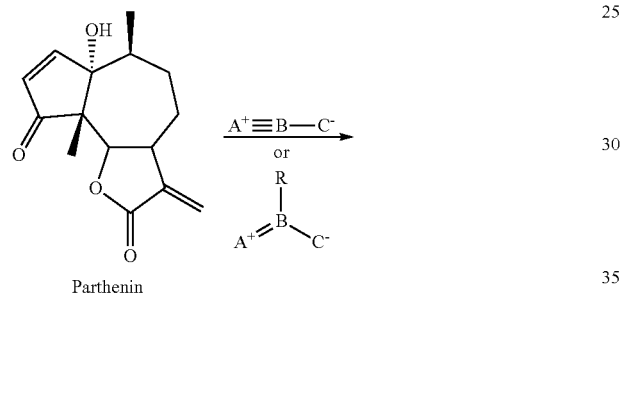

Parthenin

Where A, B, C = C, N, O, P ----

X = —C═N—O—, —C—N—O—, —N— etc.

Spiro derivatives

Scheme 2

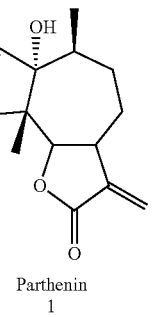

Spiro isoxazoline derivative
2

↑

Parthenin
1

↙        ↘

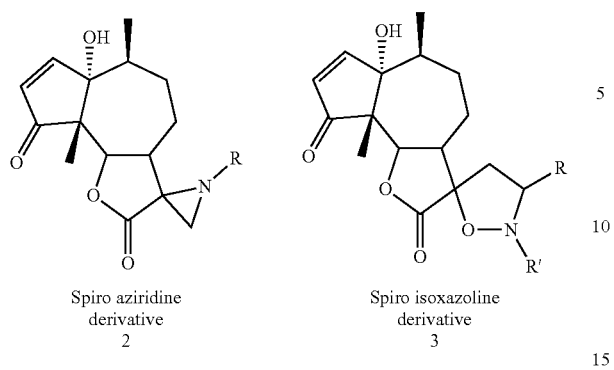
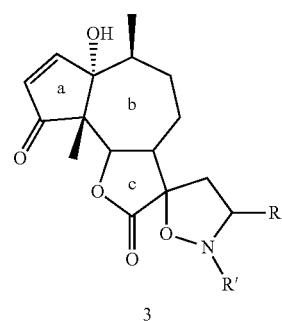
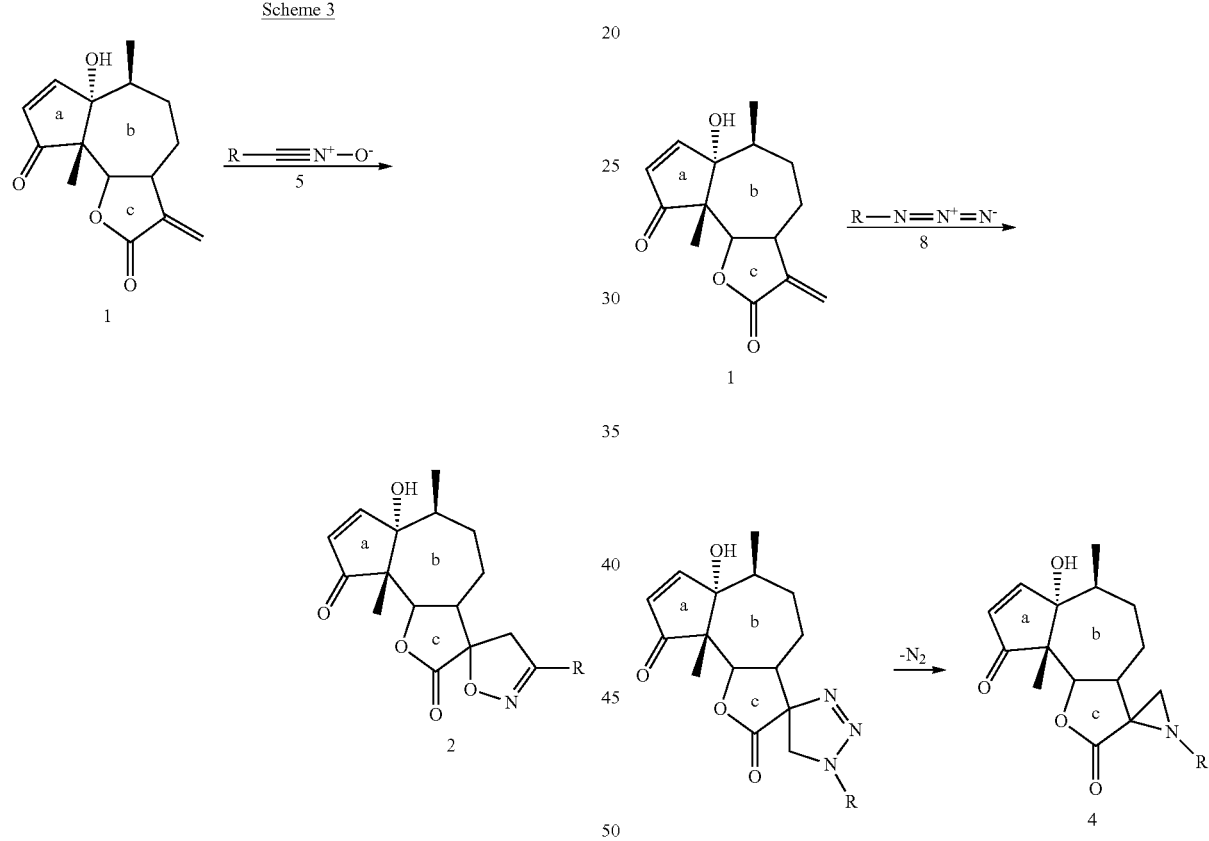
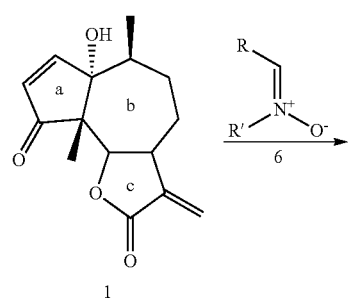
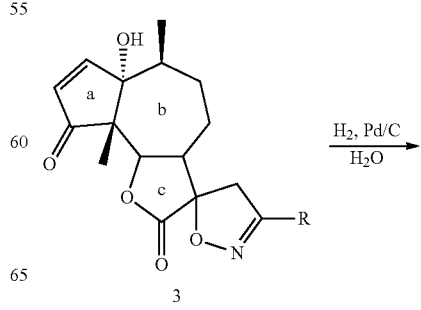

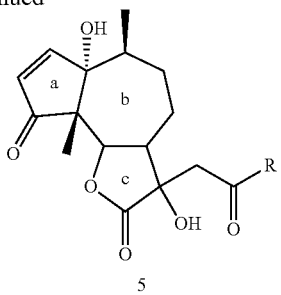

5

We claim:
1. A compound of structure:

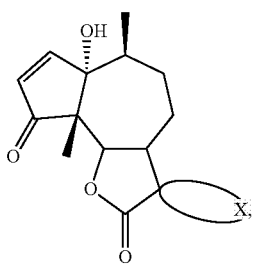

wherein X is defined such that the compound is selected from the group consisting of (4-methoxyphenyl)-spiro-isoxazolinyl parthenin, (2-nitrophenyl)-spiro- isoxazolinyl parthenin, (3-nitrophenyl)-spiro-isoxazolinyl parthenin, (3-hydroxyphenyl)-spiro- isoxazolinyl parthenin, (2-hydroxyphenyl)-spiro-isoxazolinyl parthenin, (4-hydroxyphenyl)-spiro-isoxazolinyl parthenin, (3-hydroxyphenyl)-spiro-isoxazolinyl parthenin, (2,3- dihydroxyphenyl)-spiro-isoxazolinyl parthenin, (2,4-dihydroxyphenyl)-spiro-isoxazolinyl parthenin, (2,5-dihydroxyphenyl)-spiro-isoxazolinyl parthenin, (3,4-dihydroxyphenyl)-spiro-isoxazolinyl parthenin, (3,5-dihydroxyphenyl)-spiro-isoxazolinyl parthenin, (2,3-dimethoxyphenyl)-spiro-isoxazolinyl parthenin, (2,3-dimethoxyphenyl)-spiro-isoxazolinyl parthenin, (2,4-dimethoxyphenyl)-spiro-isoxazolinyl parthenin, (2,5-dimethoxyphenyl)-spiro-isoxazolinyl parthenin, (2,6-diethoxyphenyl)-spiro-isoxazolinyl parthenin, (3,5-dipropoxyphenyl)-spiro-isoxazolinyl parthenin, (2-hydroxy-5-methoxyphenyl)-spiro-isoxazolinyl parthenin, (3-hydroxy-4-methoxyphenyl)-spiro-isoxazolinyl parthenin, (2-hydroxy-4-methoxyphenyl)-spiro-isoxazolinyl parthenin, (2-Thianyl-6-methoxyphenyl)-spiro-isoxazolinyl parthenin, (2-methoxy-4-hydroxyphenyl)-spiro-isoxazolinyl parthenin, (2-,3-dichlorophenyl)-spiro- isoxazolinyl parthenin, (2-,4-dichlorophenyl)-spiro-isoxazolinyl parthenin, (2-,5-dichlorophenyl)-spiro-isoxazolinyl parthenin, (4-N,N'-dimethylphenyl)-spiro-isoxazolinyl parthenin, (4-nitrophenyl)-spiro-isoxazolinyl parthenin, (2-bromophenyl)-spiro- isoxazolinyl parthenin, (3,5-dibromophenyl)-spiro-isoxazolinyl parthenin, (2-chlorophenyl)- spiro-isoxazolinyl parthenin, (2-bromo-3-chlorophenyl)-spiro-isoxazolinyl parthenin, (2-bromo-4-chlorophenyl)-spiro-isoxazolinyl parthenin, (2-bromo-6-chlorophenyl)-spiro-isoxazolinyl parthenin, (2-chloro-4-fluorophenyl)-spiro-isoxazolinyl parthenin, (2-chloro-6-fluorophenyl)-spiro-isoxazolinyl parthenin, (3-chloro-2-fluorophenyl)-spiro-isoxazolinyl parthenin, (3-chloro-4-fluorophenyl)-spiro-isoxazolinyl parthenin, (4-chloro-3-fluorophenyl)-spiro-isoxazolinyl parthenin, (2-chloro-6-hydroxyphenyl)-spiro-isoxazolinyl parthenin, (2-chloro-4-hydroxyphenyl)-spiro-isoxazolinyl parthenin, (2-bromo-5-fluorophenyl)-spiro-isoxazolinyl parthenin, (3-bromo-4-fluorophenyl)-spiro-isoxazolinyl parthenin, (4-bromo-2-fluorophenyl)-spiro-isoxazolinyl parthenin, (5-bromo-5-fluorophenyl)-spiro-isoxazolinyl parthenin,(2,3,5,6-tetrafluorophenyl)-spiro-isoxazolinyl parthenin, (2,3,4,5,6-pentafluorophenyl)-spiro-isoxazolinyl parthenin, (3-bromo-5-chloro-2-hydroxyphenyl)-spiro-isoxazolinyl parthenin, (4-N-acetylphenyl)-spiro-isoxazolinyl parthenin, (3-N-acetylphenyl)-spiro-isoxazolinyl parthenin, (2-N-acetylphenyl)-spiro-isoxazolinyl parthenin, (2,4,6-trihydroxyphenyl)-spiro-isoxazolinyl parthenin, (2,4,6-trimethoxyphenyl)-spiro-isoxazolinyl parthenin, (4-hydroxy-3-methylphenyl)-spiro-isoxazolinyl parthenin, (3-methylphenyl)-spiro-isoxazolinyl parthenin, (2,4-dimethylphenyl)-spiro-isoxazolinyl parthenin, (2,4,6-trimethylphenyl)-spiro-isoxazolinyl parthenin, (2-ethylphenyl)-spiro-isoxazolinyl parthenin, (4-ethylphenyl)-spiro-isoxazolinyl parthenin, (2-ethoxyphenyl)-spiro isoxazolinyl parthenin, (3-ethoxyphenyl)-spiro-isoxazolinyl parthenin, (4-ethoxyphenyl)-spiro isoxazolinyl parthenin, (4-isopropylphenyl)-spiro isoxazolinyl parthenin, (2,4,6-triethoxyphenyl)-spiro-isoxazolinyl parthenin, (4-thianylphenyl)-spiro isoxazolinyl parthenin, (3-thiomethylphenyl)-spiro-isoxazolinyl parthenin, methyl-3-(isoxazolyl-5-parthenyl)-benzoate, methyl-2-(isoxazolyl-5-parthenyl)-benzoate, ethyl-4-(isoxazolyl-5-parthenyl)-benzoate, theinyl-spiro-isoxazolinyl parthenin, furyl-spiro-isoxazolinyl parthenin, indolyl-spiro-isoxazolinyl parthenin, pyridyl-spir-isoxazolinyl parthenin, napthyl-spiro- isoxazolinyl parthenin, anthracenyl-spiro isoxazolinyl parthenin, N-(4-fluorophenyl)-C-(4-methoxyphenyl)-spiro-isoxazolidinyl parthenin, N-(4-fluorophenyl)-C-(2-nitrophenyl)-spiro-isoxazolidinyl parthenin, N-(4-fluorophenyl)-C-(3-nitrophenyl)-spiro-isoxazolidinyl parthenin, N-(4-fluorophenyl)-C-(3-hydroxyphenyl)-spiro-isoxazolidinyl parthenin, N-(2-florophenyl)-C-(2-hydroxyphenyl)-spiro-isoxazolidinyl parthenin, N-(2-florophenyl)-C-(4-hydroxyphenyl)-spiro-isoxazolidinyl parthenin, N-(2-florophenyl)-C-(2,3-hydroxyphenyl)-spiro-isoxazolidinyl parthenin, N-(2-florophenyl)-C-(2,3-hydroxyphenyl)-spiro-isoxazolidinyl parthenin, N-(2-chlorophenyl)-C-(2,5-hydroxyphenyl)-spiro-isoxazolidinyl parthenin, N-(2-florophenyl)-C-(3,4-hydroxyphenyl)-spiro-soxazolidinyl parthenin, N-(2-methylphenyl)-C-(3,5-hydroxyphenyl)-spiro-isoxazolidinyl parthenin, N-(2-methylphenyl)-C-(2,3-dimethoxyphenyl)-spiro-isoxazolidinyl parthenin, N-(2-methylphenyl)-C-(2,5-dimethoxyphenyl)-spiro isoxazolidinyl parthenin, N-(2-methylphenyl)-C-(2,4-dimethoxyphenyl)-spiro-isoxazolidinyl parthenin, N-(2-methoxyphenyl)-C-(2,5-dimethoxyphenyl)-spiro-isoxazolidinyl parthenin, N-(2-methoxyphenyl)-C-(2,6-diethoxyphenyl)-spiro-isoxazolidinyl parthenin, N-(2-nitrophenyl)-C-(3,5-dipropoxyphenyl)-spiro-isoxazolidinyl parthenin, N-(2-nitrophenyl)-C-(2-hydroxy-5-methoxyphenyl)-spiro-isoxazolinyl parthenin, N-(2-nitrophenyl)-C-(3-hydroxy-4-methoxyphenyl)-spiro-isoxazolidinyl parthenin, N-(2-bromophenyl)-C-(2-hydroxy-4-methoxyphenyl)-spiro-isoxazolidinyl parthenin, N-(2-bromophenyl)-C-(2-thianyl-6-methoxyphenyl)-spiro-isoxazolidinyl parthenin, N-(2-chlorophenyl)-C-(2-methoxy-4-hydroxyphenyl)-spiro-isoxazolidinyl parthenin, N-(2-chlorophenyl)-C-(2,3-dichlorophenyl)-spiro-isoxazolidinyl parthenin, N-(2-chlorophenyl)-C-(2,4-dichlorophenyl)-spiro-isoxazolidinyl parthenin, N-(2-chlorophenyl)-C-(2-,5-dichlorophenyl)-spiro-isoxazolidinyl parthenin, N-(4-hydroxyphenyl)-C-(4-N,N'-dimethylphenyl)-spiro-isoxazolidinyl parthenin, N-(4-hydroxyphenyl)-C-(4-nitrophenyl)-spiro-isoxazolidinyl parthenin, N-(4-hydroxyphenyl)-C-(2-bromophenyl)-spiro-isoxazolidinyl parthenin, N-(4-hydroxyphenyl)-C-(3,5-dibromophenyl)-spiro-isoxazolidinyl parthenin, N-(4-hydroxyphenyl)-C-(2-chlorophenyl)-spiro-isoxazolidinyl parthenin, N-(4-hydroxyphenyl)-C-(2-bromo-3-chlorophenyl)-spiro-isoxazolidinyl parthenin, N-(4-chloro-3-hydroxyphenyl)-C-(2-bromo-4-chlorophenyl)-spiro-isoxazolidinyl parthenin, N-(4-chloro-3-hydroxyphenyl)-C-(2-bromo-6-chlorophenyl)-spiro-isoxazolidinyl parthenin, N-(4-chloro-3-hydroxyphenyl)-C-(2-chloro-4-fluorophenyl)-spiro-isoxazolidinyl parthenin, N-(4-chloro-3-bromophenyl)-C-(2-chloro-6-fluorophenyl)-spiro-isoxazolidinyl parthenin, N-(4-chloro-3-hydroxyphenyl)-C-(3-chloro-2-fluorophenyl)-spiro-isoxazolidinyl parthenin, N-(4-chloro-3-hydroxyphenyl)-C-(3-chloro-4-fluorophenyl)-spiro-isoxazolidinyl parthenin, N-(2-nitrophenyl)-C-(4-chloro-3-fluorophenyl)-spiro-isoxazolidinyl parthenin, N-(2-nitrophenyl)-C-(2-chloro-6-hydroxyphenyl)-spiro-isoxazolidinyl parthenin, N-(2-nitrophenyl)-C-(2-chloro-4-hydroxyphenyl)-spiro-isoxazolidinyl parthenin, N-(2-nitrophenyl)-C-(2-bromo-5-fluorophenyl)-spiro-isoxazolidinyl parthenin, N-(2-nitrophenyl)-C-(3-bromo-4-fluorophenyl)-spiro-isoxazolidinyl parthenin, N-(2-methoxyphenyl)-C-(4-bromo-2-fluorophenyl)-spiro-isoxazolidinyl parthenin, N-(2-methoxyphenyl)-C-(5-bromo-5-fluorophenyl)-spiro-isoxazolidinyl parthenin, N-(2-methoxyphenyl)-C-(2,3,5,6-tetrafluorophenyl)-spiro-isoxazolidinyl parthenin, N-(2-methoxyphenyl)-C-(2,3,4,5,6-pentafluorophenyl)-spiro-isoxazolidinyl parthenin, N-(2-methoxyphenyl)-C-(3-bromo-5-chloro-2-hydroxyphenyl)-spiro-isoxazolidinyl parthenin, N-(2-methoxyphenyl)-C-(4-N-acetylphenyl)-spiro-isoxazolidinyl parthenin, N-(2-methoxyphenyl)-C-(3-N-acetylphenyl)-spiro-isoxazolidinyl parthenin, N-(2-methoxyphenyl)-C-(2-N-acetylphenyl)-spiro-isoxazolidinyl parthenin, N-(2-methoxyphenyl)-C-(2,4,6-trihydroxyphenyl)-spiro-isoxazolidinyl parthenin, N-(2-methoxyphenyl)-C-(2,4,6-trimethoxyphenyl)-spiro-isoxazolidinyl parthenin, N-(2-methoxyphenyl)-C-(3,4-methylenedioxyphenyl)-spiro-isoxazolidinyl parthenin, N-(2-methoxyphenyl)-C-(4-hydroxy-3-methylphenyl)-spiro-isoxazolidinyl parthenin, N-(2-nitrophenyl)-C-(3-methylphenyl)-spiro-isoxazolidinyl parthenin, N-(2-nitrophenyl)-C-(2,4-dimethylphenyl)-spiro-isoxazolidinyl parthenin, N-(2-nitrophenyl)-C-(2,4,6-trimethylphenyl)-spiro-isoxazolidinyl parthenin, N-(2-nitrophenyl)-C-(2-ethylphenyl)-spiro-isoxazolidinyl parthenin, N-(2-nitrophenyl)-C-(4-ethylphenyl)-spiro-isoxazolidinyl parthenin, N-(2-ethoxyphenyl)-spiro-isoxazolidinyl parthenin, N-(2-nitrophenyl)-C-(3-ethoxyphenyl)-spiro-isoxazolidinyl parthenin, N-(2-nitrophenyl)-C-(4-ethoxyphenyl)-spiro-isoxazolidinyl parthenin, N-(2-nitrophenyl)-C-(4-isopropylphenyl)-spiro-isoxazolidinyl parthenin, N-(2-nitrophenyl)-C-(2,4,6-triethoxyphenyl)-spiro-isoxazolidinyl parthenin, N-(2-methoxyphenyl)-C-(4-thianylphenyl)-spiro-isoxazolidinyl parthenin, N-(2-methoxyphenyl)-C-(3-thiomethylphenyl)-spiro-isoxazolidinyl parthenin, N-(2-methoxyphenyl)-C-methyl-3-(isoxazolidinyl-5-parthenyl)-benzoate, N-(2-methoxyphenyl)-C-methyl-2-(isoxazolidinyl-5-parthenyl)-benzoate, N-(2-methoxyphenyl)-C-ethyl-4-(isoxazolidinyl-5-parthenyl)-benzoate, N-(4-chloro-3-fluorophenyl)-C-(theiny)l-spiro-isoxazolidinyl parthenin, N-(4-chlorophenyl)-C-(furyl)-spiro-isoxazolidinyl parthenin, N-(4-chloro-3-fluorophenyl)-C-(indolyl)-spiro-isoxazolidinyl parthenin, N-(4-chloro-3-fluorophenyl)-C-(pyridyl)-spiro-isoxazolidinyl parthenin, N-(4-chlorophenyl)-C-(napthyl)-spiro-isoxazolidinyl parthenin, N-(4-chloro-3-fluorophenyl)-C-(anthracenyl)-spiro-isoxazolidinyl parthenin, (4-methoxyphenyl)-spiro-aziridinyl parthenin, (2-nitrophenyl)-spiro-aziridinyl parthenin, (3-nitrophenyl)-spiro-aziridinyl parthenin, (3-hydroxyphenyl)-spiro-aziridinyl parthenin, (2-hydroxyphenyl)-spiro-aziridinyl parthenin, (4-hydroxyphenyl)-spiro-aziridinyl parthenin, (3-hydroxyphenyl)-spiro-aziridinyl parthenin, (2,3-dihydroxyphenyl)-spiro-aziridinyl parthenin, (2,4-dihydroxyphenyl)-spiro-aziridinyl parthenin, (2,5-dihydroxyphenyl)-spiro-aziridinyl parthenin, (3,4-dihydroxyphenyl)-spiro-aziridinyl parthenin, (3,5-dihydroxyphenyl)-spiro-aziridinyl parthenin, (2,3-dimethoxyphenyl)-spiro-aziridinyl parthenin, (2,3-dimethoxyphenyl)- spiro-aziridinyl parthenin, (2,4-dimethoxyphenyl)-spiro-aziridinyl parthenin, (2,5-dimethoxyphenyl)-spiro-aziridinyl parthenin, (2,6-diethoxyphenyl)-spiro-aziridinyl parthenin, (3,5-dipropoxyphenyl)-spiro-aziridinyl parthenin, (2-hydroxy-5-methoxyphenyl)-spiro-aziridinyl parthenin, (3-hydroxy-4-methoxyphenyl)-spiro-aziridinyl parthenin, (2-hydroxy-4-methoxyphenyl)-spiro-aziridinyl parthenin, (2-Thianyl-6-methoxyphenyl)-spiro-aziridinyl parthenin, (2-methoxy-4-hydroxyphenyl)-spiro-aziridinyl parthenin, (2-,3-dichlorophenyl)-spiro-aziridinyl parthenin, (2-,4-dichlorophenyl)-spiro-aziridinyl parthenin, (2-,5-dichlorophenyl)-spiro-aziridinyl parthenin, (4-N,N'-dimethylphenyl)-spiro-aziridinyl parthenin, (4-nitrophenyl)- spiro-aziridinyl parthenin, (2-bromophenyl)-spiro-aziridinyl parthenin, (3,5-dibromophenyl)-spiro-aziridinyl parthenin, (2-chlorophenyl)-spiro-aziridinyl parthenin, (2-bromo-3-chlorophenyl)-spiro-aziridinyl parthenin, (2-bromo-4-chlorophenyl)-spiro-aziridinyl parthenin, (2-bromo-6-chlorophenyl)-spiro-aziridinyl parthenin, (2-chloro-4-fluorophenyl)-spiro-aziridinyl parthenin, (2-chloro-6-fluorophenyl)-spiro-aziridinyl parthenin, (3-chloro-2-fluorophenyl)-spiro-aziridinyl parthenin, (3-chloro-4-fluorophenyl)-spiro-aziridinyl parthenin, (4-chloro-3-fluorophenyl)-spiro-aziridinyl parthenin, (2-chloro-6-hydroxyphenyl)-spiro-aziridinyl parthenin, (2-chloro-4-hydroxyphenyl)-spiro-aziridinyl parthenin, (2-bromo-5-fluorophenyl)-spiro-aziridinyl parthenin, (3-bromo-4-fluorophenyl)-spiro-aziridinyl parthenin, (4-bromo-2-fluorophenyl)-spiro-aziridinyl parthenin, (5-bromo-5-fluorophenyl)-spiro-aziridinyl parthenin, (2,3,5,6-tetrafluorophenyl)-spiro-aziridinyl parthenin, (2,3,4,5,6-pentafluorophenyl)-spiro-aziridinyl parthenin, (3-bromo-5-chloro-2-hydroxyphenyl)-spiro-aziridinyl parthenin, (4-N-acetylphenyl)-spiro-aziridinyl parthenin, (3-N-acetylphenyl)-spiro-aziridinyl parthenin, (2-N-acetylphenyl)-spiro-aziridinyl parthenin, (2,4,6-trihydroxyphenyl)-spiro-aziridinyl parthenin, (2,4,6-trimethoxyphenyl)-spiro-aziridinyl parthenin, (3,4-methylenedioxyphenyl)-spiro-aziridinyl parthenin, (4-hydroxy-3-methylphenyl)-spiro-aziridinyl parthenin, (3-methylphenyl)-spiro-aziridinyl parthenin, (2,4-dimethylphenyl)-spiro-aziridinyl parthenin, (2,4,6-trimethylphenyl)-spiro-aziridinyl parthenin, (2-ethylphenyl)-spiro-aziridinyl parthenin, (4-ethylphenyl)-spiro-aziridinyl parthenin, (2-ethoxyphenyl)-spiro-aziridinyl parthenin, (3-ethoxyphenyl)-spiro-aziridinyl parthenin, (4-ethoxyphenyl)-spiro-aziridinyl parthenin, (4-isopropylphenyl)-spiro-aziridinyl parthenin, (2,4,6-triethoxyphenyl)-spiro-aziridinyl parthenin, (4-thianylphenyl)-spiro-aziridinyl parthenin, (3-thiomethylphenyl)-spiro-aziridinyl parthenin, methyl-3-(aziridinyl-2-parthenyl)-benzoate, methyl-2-(aziridinyl-2-parthenyl)-benzoate, ethyl-4-(aziridinyl-2-parthenyl)-benzoate, theinyl-spiro-aziridinyl parthenin, furyl-spiro-aziridinyl parthenin, indolyl-spiro-aziridinyl parthenin, pyridyl-spiro-aziridinyl parthenin, napthyl-spiro- aziridinyl parthenin, anthracenyl-spiro-aziridinyl parthenin, (4-methoxyphenyl)-spiro-1,2,3-triazolinyl parthenin, (2-nitrophenyl)-spiro-1,2,3-triazolinyl parthenin, (3-nitrophenyl)-spiro-1,2,3-triazolinyl parthenin, (3-hydroxyphenyl)-spiro-1,2,3-triazolinyl parthenin, (2-hydroxyphenyl)-spiro- 1,2,3-triazolinyl parthenin, (4-hydroxyphenyl)-spiro- 1,2,3-triazolinyl parthenin, (3-hydroxyphenyl)-spiro-1,2,3-triazolinyl parthenin, (2,3-dihydroxyphenyl)-spiro-1,2,3-triazolinyl parthenin, (2,4-dihydroxyphenyl)-spiro-1,2,3-triazolinyl parthenin, (2,5-dihydroxyphenyl)-spiro- 1,2,3-triazolinyl parthenin, (3,4-dihydroxyphenyl)-spiro- 1,2,3-triazolinyl parthenin, (3,5-dihydroxyphenyl)-spiro-1,2,3-triazolinyl parthenin, (2,3-dimethoxyphenyl)-spiro-1,2,3-triazolinyl parthenin, (2,3-dimethoxyphenyl)-spiro-1,2,3-triazolinyl parthenin, (2,4-dimethoxyphenyl)-spiro-1,2,3-triazolinyl parthenin, (2,5-dimethoxyphenyl)-spiro- 1,2,3-triazolinyl parthenin, (2,6-diethoxyphenyl)-spiro-1,2,3-triazolinyl parthenin, (3,5-dipropoxyphenyl)-spiro-1,2,3-triazolinyl parthenin, (2-hydroxy-5-methoxyphenyl)-spiro-1,2,3-triazolinyl parthenin, (3-hydroxy-4-methoxyphenyl)-spiro-1,2,3-triazolinyl parthenin, (2-hydroxy-4-methoxyphenyl)-spiro-1,2,3-triazolinyl parthenin, (2-Thianyl-6-methoxyphenyl)-spiro-1,2,3-triazolinyl parthenin, (2-methoxy-4-hydroxyphenyl)-spiro-1,2,3-triazolinyl parthenin, (2-,3-dichlorophenyl)-spiro-1,2,3-triazolinyl parthenin, (2-,4-dichlorophenyl)-spiro-1,2,3-triazolinyl parthenin, (2-,5-dichlorophenyl)-spiro-1,2,3-triazolinyl parthenin, (4-N,N'-dimethylphenyl)-spiro-1,2,3-triazolinyl parthenin, (4-nitrophenyl)-spiro-1,2,3-triazolinyl parthenin, (2-bromophenyl)-spiro-1,2,3-triazolinyl parthenin, (3,5-dibromophenyl)-spiro 1,2,3-triazolinyl parthenin, (2-chlorophenyl)-spiro1,2,3-triazolinyl parthenin, (2-bromo-3-chlorophenyl)-spiro-1,2,3-triazolinyl parthenin, (2-bromo-4-chlorophenyl)-spiro-1,2,3-triazolinyl parthenin, (2-bromo-6-chlorophenyl)-spiro-1,2,3-triazolinyl parthenin, (2-chloro-4-fluorophenyl)-spiro-1,2,3-triazolinyl parthenin, (2-chloro-6-fluorophenyl)-spiro-1,2,3-triazolinyl parthenin, (3-chloro-2-fluorophenyl)-spiro-1,2,3-triazolinyl parthenin, (3-chloro-4-fluorophenyl)-spiro-1,2,3-triazolinyl parthenin, (4-chloro-3-fluorophenyl)-spiro-1,2,3-triazolinyl parthenin, (2-chloro-6-hydroxyphenyl)-spiro-1,2,3-triazolinyl parthenin, (2-chloro-4-hydroxyphenyl)-spiro-1,2,3-triazolinyl parthenin, (2-bromo-5-fluorophenyl)-spiro-triazolinyl parthenin, (3-bromo-4-fluorophenyl)-spiro-triazolinyl parthenin, (4-bromo-2-fluorophenyl)-spiro-1,2,3-triazolinyl parthenin, (5-bromo-5-fluorophenyl)-spiro-1,2,3-triazolinyl parthenin, (2,3,5,6-tetrafluorophenyl)-spiro-1,2,3-triazolinyl parthenin, (2,3,4,5,6-pentafluorophenyl)-spiro-1,2,3-triazolinyl parthenin, (3-bromo-5-chloro-2-hydroxyphenyl)-spiro-1,2,3-triazolinyl parthenin, (4-N-acetylphenyl)-spiro-1,2,3-triazolinyl parthenin, (3-N-acetylphenyl)-spiro-1,2,3-triazolinyl parthenin, (2-N-acetylphenyl)-spiro-1,2,3-triazolinyl parthenin, (2,4,6-trihydroxyphenyl)-spiro-1,2,3-triazolinyl parthenin, (2,4,6-trimethoxyphenyl)-spiro- 1,2,3-triazolinyl parthenin, (3,4-methylenedioxyphenyl)-spiro-1,2,3-triazolinyl parthenin, (4-hydroxy-3-methylphenyl)-spiro-1,2,3-triazolinyl parthenin, (3-methylphenyl)-spiro-1,2,3-triazolinyl parthenin, (2,4-dimethylphenyl)-spiro-1,2,3-triazolinyl parthenin, (2,4,6-trimethylphenyl)-spiro-1,2,3-triazolinyl parthenin, (2-ethylphenyl)-spiro-1,2,3-triazolinyl parthenin, (4-ethylphenyl)- spiro-1,2,3-triazolinyl parthenin, (2-ethoxyphenyl)-spiro-1,2,3-triazolinyl parthenin, (3-ethoxyphenyl)-spiro-1,2,3-triazolinyl parthenin, (4-ethoxyphenyl)-spiro-1,2,3-triazolinyl parthenin, (4-isopropylphenyl)-spiro-1,2,3-triazolinyl parthenin, (2,4,6-triethoxyphenyl)-spiro-1,2,3-triazolinyl parthenin, (4-thianylphenyl)-spiro-1,2,3-triazolinyl parthenin, (3-thiomethylphenyl)-spiro-1,2,3-triazolinyl parthenin, methyl-3-(1,2,3- triazolinyl-5-parthenyl)-benzoate, methyl-2-(1,2,3-triazolinyl-5-parthenyl)-benzoate, ethyl-4-(1,2,3-triazolinyl-5-parthenyl)-benzoate, theinyl-spiro-1,2,3-triazolinyl parthenin, furyl-spiro-1,2,3-triazolinyl parthenin, indolyl-spiro-1,2,3-triazolinyl parthenin, pyridyl-spiro-1,2,3-triazolinyl parthenin, napthyl-spiro-1,2,3-triazolinyl parthenin, and anthracenyl-spiro-1,2,3-triazolinyl parthenin.

2. The compound of claim 1, wherein said compound is anthracenyl-spiro isoxazolinyl parthenin.

* * * * *